US007238713B2

(12) United States Patent
Anderson et al.

(10) Patent No.: US 7,238,713 B2
(45) Date of Patent: Jul. 3, 2007

(54) MUSCARINIC AGONISTS

(75) Inventors: Carl-Magnus A. Anderson, Glostrup (DK); Bo Lennart M. Friberg, Bronshoj (DK); Niels Skjaerbaek, Vedbaek (DK); Tracy A. Spalding, San Diego, CA (US); Allan K. Uldam, Lyngby (DK)

(73) Assignee: Acadia Pharmaceuticals, Inc., San Diego, CA (US)

( * ) Notice: Subject to any disclaimer, the term of this patent is extended or adjusted under 35 U.S.C. 154(b) by 223 days.

(21) Appl. No.: 10/623,119

(22) Filed: Jul. 17, 2003

(65) Prior Publication Data
US 2005/0113357 A1 May 26, 2005

Related U.S. Application Data

(62) Division of application No. 09/844,685, filed on Apr. 27, 2001, now Pat. No. 6,627,645.

(60) Provisional application No. 60/200,791, filed on Apr. 28, 2000.

(51) Int. Cl.
*A61K 31/445* (2006.01)
*C07D 409/12* (2006.01)

(52) U.S. Cl. .................... 514/324; 514/321; 546/198; 546/202

(58) Field of Classification Search ............... 514/321, 514/324; 546/198, 202
See application file for complete search history.

(56) References Cited

U.S. PATENT DOCUMENTS

| 3,412,097 | A | | 11/1968 | Gerardus | |
|---|---|---|---|---|---|
| 3,417,087 | A | * | 12/1968 | Neiss et al. ................. | 544/146 |
| 4,186,136 | A | * | 1/1980 | Robba et al. ................ | 540/596 |
| 4,458,075 | A | | 7/1984 | Davis et al. ................. | 546/198 |
| 4,870,085 | A | | 9/1989 | Glaser et al. ............... | 514/323 |
| 5,494,908 | A | | 2/1996 | O'Malley et al. | |
| 5,580,982 | A | | 12/1996 | O'Malley et al. | |
| 5,654,320 | A | | 8/1997 | Catlow et al. ............. | 514/322 |
| 5,703,070 | A | | 12/1997 | Lavielle et al. ............ | 514/212 |
| 5,707,798 | A | | 1/1998 | Brann | |
| 5,756,754 | A | | 5/1998 | O'Malley et al. | |
| 5,912,132 | A | | 6/1999 | Brann | |
| 5,925,766 | A | | 7/1999 | O'Malley et al. | |
| 5,955,281 | A | | 9/1999 | Brann | |
| 6,046,203 | A | | 4/2000 | O'Malley et al. | |
| 6,566,364 | B2 | | 5/2003 | Peglion et al. | |
| 2001/0034352 | A1 | | 10/2001 | Pelgion et al. | |

FOREIGN PATENT DOCUMENTS

| DE | 4039631 A1 | 6/1992 |
|---|---|---|
| EP | 0091512 | 10/1983 |
| EP | 0511610 | 11/1992 |
| NL | 6511642 | 3/1966 |
| WO | WO 98/04546 | 2/1998 |
| WO | WO 98/20548 | 7/1998 |
| WO | WO 98/57953 | 12/1998 |
| WO | WO 94/12495 | 2/2003 |

OTHER PUBLICATIONS

Vitali et al. "Biological properties . . ." CA 70:37702 (1969).*
Moltzen et al. "The use of 4-phenylpiperidines . . ." CA 119:117118 (1993).*
Nakazato et al. "Preparation of thiazole . . ." CA 126:8111(1996).*
Exhibit A.*
Asahi Chem., 3-aminoindazole derivatives, CA 101:23469 (1983).
Dutta, et al., Highly selective, novel analogs of 4-[2-(diphenylmethoxy)ethyl]-1-benzylpiperidine for the dopamine transporter: effect of different aromatic substitutions on their affinity and selectivity, CA 126:69745 (1997).
Fujimura, et al., Indazole derivatives, CA 87:53273 (1976).
Hanning, et al., Preparation of some derivatives of 5-methyl-indazole-3-carboxylic acid, CA 80:82791 (1973).
Lounasmaa, M., et al., Acid-catalyzed epimerization of indolo[2,3α]quinolizidines. 1-,2- and 3-monosubstituted alkyl derivatives, Tetrahedron, 53(14):5349-5356 (1997).
Lounasmaa, M., et al., Stereochemical course of the modified polonovski reaction and meucuric acetate oxidation in the preparation of 2-substituted 1,2,3,4,6,7,12,12b-octahydroindolo[2,3-α]quinolizines, Tetrahedron, 47(32):6371-6380 (1991).
Lounasmaa, M., et al., Stereoregulation of the c(12b)H-C(2)H relationship in the preparation of 2-substituted 1,2,3,4,6,7,12,12b-octahydroindolo[2,3-α]quinolizines, Tetrahedron, 44(12):3975-3992 (1989).
Minieri, et al., Bactericidal and fungicidal 1-(aminomethyl)indazoles, CA 79:442494 (1973).
Orth, et al., Centrally acting isosteric Mannich bases, CA 70:11473 (1968).
Pavia, et al., "Structure activity . . ." CA 118:6834 (1992).
Rao, et al., Synthesis and radioprotective activity of .beta.-(3-indazolyl)ethylamine derivatives, CA 108:94460 (1987).
Synthelabo, Preparation of 1-[(hetero)aroyl]-4-(4-imidazolyl)piperidines as serotoninergic receptor antagonists, CA 121:9402 (1994).
Zenitz, et al., 1-indolylglyoxalyl)piperidines, CA 64:67726 (1965).
Sample compounds.
Davis, et al. *3-Substituted-1-2-Benzisoxazoles: Novel Antipsychotic Agents*, Drug Design and Discovery, vol. 8, No. 3 1992, Harwood Academic Publishers GmbH, pp. 225-240; XP000608016.
Britton, et al. "Structure-Activity Relationships of a Series of Benzothiophenederived NPY Y1 Anatagonists: Optimization of the C-2 Side Chain" Bioorganic & Medicinal Chemistry Letters 9, (1999) 475-480.
Chevolot, et al. "Indoles, XI Synthesis of DI . . . " CA 84: 31279 (1975).

* cited by examiner

*Primary Examiner*—Celia Chang
(74) *Attorney, Agent, or Firm*—Knobbe, Martens Olson & Bear, LLP

(57) ABSTRACT

Compounds and methods are provided for the treatment of disease conditions in which modification of cholinergic, especially muscarinic m1, m4, or both m1 and m4, receptor activity has a beneficial effect. In the method, an effective amount of a compound is administered to a patient in need of such treatment.

16 Claims, No Drawings

MUSCARINIC AGONISTS

This application is a divisional of U.S. patent application Ser. No. 09/844,685, entitled "MUSCARINIC AGONISTS," filed Apr. 27, 2001, now U.S. Pat. No. 6,627,645, issued Sep. 30, 2003, by Andersson, et al., which in turn claims priority to U.S. Provisional Patent Application Ser. No. 60/200,791, filed Apr. 28, 2000, all of which are incorporated by reference herein in their entirety, including any drawings.

FIELD OF THE INVENTION

The present invention relates to compounds that affect cholinergic receptors, especially muscarinic receptors. The present invention provides compounds that are agonists of cholinergic receptors including muscarinic receptors, especially the m1 and m4 subtype of muscarinic receptors. The invention also provides methods of using the provided compounds for modulating conditions associated with cholinergic receptors, especially for treating or alleviating disease conditions associated with muscarinic receptors, e.g., m1 or m4 subtypes of receptors.

BACKGROUND OF THE INVENTION

Muscarinic cholinergic receptors mediate the actions of the neurotransmitter acetylcholine in the central and peripheral nervous systems, gastrointestinal system, heart, endocrine glands, lungs, and other tissues. Muscarinic receptors play a central role in the central nervous system for higher cognitive functions, as well as in the peripheral parasympathetic nervous system. Five distinct muscarinic receptor subtypes have been identified, m1–m5. The m1 subtype is the predominant subtype found in the cerebral cortex and is believed to be involved in the control of cognitive functions; m2 is the predominant subtype found in heart and is believed to be involved in the control of heart rate; m3 is believed to be involved in gastrointestinal and urinary tract stimulation as well as sweating and salivation; m4 is present in brain and may be involved in locomotion; and m5, present in brain, may be involved in certain functions of the central nervous system associated with the dopaminergic system.

Conditions associated with cognitive impairment, such as Alzheimer's disease, are accompanied by loss of acetylcholine in the brain. This is believed to be the result of degeneration of cholinergic neurons in the basal forebrain, which innervate areas of the association cortex, and hippocampus, which is involved in higher processes.

Efforts to increase acetylcholine levels have focused on increasing levels of choline, the precursor for acetylcholine synthesis, and on blocking acetylcholine esterase (AChE), the enzyme that metabolizes acetylcholine. Administration of choline or phosphatidylcholine has not been very successful. AChE inhibitors have shown some therapeutic efficacy, but may cause cholinergic side effects due to peripheral acetylcholine stimulation, including abdominal cramps, nausea, vomiting, diarrhea, anorexia, weight loss, myopathy and depression. Gastrointestinal side effects have been observed in about a third of the patients treated. In addition, some ACHE inhibitors, such as tacrine, have also been found to cause significant hepatotoxicity, with elevated liver transaminases observed in about 30% of patients. The adverse effects of AChE inhibitors have limited their clinical utility.

Known m1 muscarinic agonists such as arecoline have also been found to be weak agonists of m2 as well as m3 subtype and are not very effective in treating cognitive impairment, most likely because of dose-limiting side effects.

There is a need for compounds that increase acetylcholine signaling or effect in the brain. Specifically there is a need for muscarinic agonists that are active at various muscarinic receptor subtypes in the central and peripheral nervous system. Furthermore, there is a need for more highly selective muscarinic agonists, such as m1- or m4-selective agents, both as pharmacological tools and as therapeutic agents.

SUMMARY OF THE INVENTION

The present invention provides compounds that affect cholinergic, especially muscarinic, receptors that have agonist activity at the m1 or m4 subtype of muscarinic receptors, or both. The compounds of the invention are of the general formula (I):

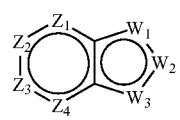

wherein:
$Z_1$ is $CR_1$ or N, $Z_2$ is $CR_2$ or N, $Z_3$ is $CR_3$ or N, and $Z_4$ is $CR_4$ or N, where no more than two of $Z_1$, $Z_2$, $Z_3$ and $Z_4$ are N;

$W_1$ is O, S, or $NR_5$, one of $W_2$ and $W_3$ is N or $CR_6$, and the other of $W_2$ and $W_3$ is CG; $W_1$ is NG, $W_2$ is $CR_5$ or N, and $W_3$ is $CR_6$ or N; or $W_1$ and $W_3$ are N, and $W_2$ is NG;

G is of formula (II):

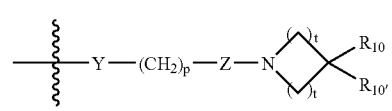

Y is O, S, CHOH, —NHC(O)—, —C(O)NH—, —C(O)—, —OC(O)—, —(O)CO—, —$NR_7$—, —CH=N—, or absent;
p is 1, 2, 3, 4 or 5;
Z is $CR_8R_9$ or absent;
each t is 1, 2, or 3;
each $R_1$, $R_2$, $R_3$, and $R_4$, independently, is H, amino, hydroxyl, halo, or straight- or branched-chain $C_{1-6}$ alkyl, $C_{2-6}$ alkenyl, $C_{2-6}$ alkynyl, $C_{1-6}$ heteroalkyl, $C_{1-6}$ haloalkyl, —CN, —$CF_3$, —$OR_{11}$, —$COR_{11}$, —$NO_2$, —$SR_{11}$, —$NHC(O)R_{11}$, —$C(O)NR_{12}R_{13}$, —$NR_{12}R_{13}$, —$NR_{11}C(O)NR_{12}R_{13}$, —$SO_2NR_{12}R_{13}$, —$OC(O)R_{11}$, —$O(CH_2)_qNR_{12}R_{13}$, or —$(CH_2)_qNR_{12}R_{13}$, where q is an integer from 2 to 6, or $R_1$ and $R_2$ together form —NH—N=N— or $R_3$ and $R_4$ together form —NH—N=N—;
each $R_5$, $R_6$, and $R_7$, independently, is H, $C_{1-6}$ alkyl; formyl; $C_{3-6}$ cycloalkyl; $C_{5-6}$ aryl, optionally substituted with halo or $C_{1-6}$ alkyl; or $C_{5-6}$ heteroaryl, optionally substituted with halo or $C_{1-6}$ alkyl;
each $R_8$ and $R_9$, independently, is H or straight- or branched-chain $C_{1-8}$ alkyl;

$R_{10}$ is straight- or branched-chain $C_{1-8}$ alkyl, $C_{2-8}$ alkenyl, $C_{2-8}$ alkynyl, $C_{1-8}$ alkylidene, $C_{1-8}$ alkoxy, $C_{1-8}$ heteroalkyl, $C_{1-8}$ aminoalkyl, $C_{1-8}$ haloalkyl, $C_{1-8}$ alkoxycarbonyl, $C_{1-8}$ hydroxyalkoxy, $C_{1-8}$ hydroxyalkyl, —SH, $C_{1-8}$ alkylthio, —O—CH$_2$—$C_{5-6}$ aryl, —C(O)—$C_{5-6}$ aryl substituted with $C_{1-3}$ alkyl or halo, $C_{5-6}$ aryl, $C_{5-6}$ cycloalkyl, $C_{5-6}$ heteroaryl, $C_{5-6}$ heterocycloalkyl, —NR$_{12}$R$_{13}$, —C(O)NR$_{12}$R$_{13}$, —NR$_{11}$C(O)NR$_{12}$R$_{13}$, —CR$_{11}$R$_{12}$R$_{13}$, —OC(O)R$_{11}$, —(O)(CH$_2$)$_S$NR$_{12}$R$_{13}$ or —(CH$_2$)$_S$NR$_{12}$R$_{13}$, s being an integer from 2 to 8;

$R_{10}'$ is H, straight- or branched-chain $C_{1-8}$ alkyl, $C_{2-8}$ alkenyl, $C_{2-8}$ alkynyl, $C_{1-8}$ alkylidene, $C_{1-8}$ alkoxy, $C_{1-8}$ heteroalkyl, $C_{1-8}$ aminoalkyl, $C_{1-8}$ haloalkyl, $C_{1-8}$ alkoxycarbonyl, $C_{1-8}$ hydroxyalkoxy, $C_{1-8}$ hydroxyalkyl, or $C_{1-8}$ alkylthio;

each $R_{11}$, independently, is H, straight- or branched-chain $C_{1-8}$ alkyl, $C_{2-8}$ alkenyl, $C_{2-8}$ alkynyl, $C_{2-8}$ heteroalkyl, $C_{2-8}$ aminoalkyl, $C_{2-8}$ haloalkyl, $C_{1-8}$ alkoxycarbonyl, $C_{2-8}$ hydroxyalkyl, —C(O)—$C_{5-6}$ aryl substituted with $C_{1-3}$ alkyl or halo, $C_{5-6}$ aryl, $C_{5-6}$ heteroaryl, $C_{5-6}$ Cycloalkyl, $C_{5-6}$ heterocycloalkyl, —C(O)NR$_{12}$R$_{13}$, —CR$_5$R$_{12}$R$_{13}$, —(CH$_2$)$_t$NR$_{12}$R$_{13}$, t is an integer from 2 to 8; and each $R_{12}$ and $R_{13}$, independently, is H, $C_{1-6}$ alkyl; $C_{3-6}$ cycloalkyl; $C_{5-6}$ aryl, optionally substituted with halo or $C_{1-6}$ alkyl; or $C_{5-6}$ heteroaryl, optionally substituted with halo or $C_{1-6}$ alkyl; or $R_{12}$ and $R_{13}$ together form a cyclic structure;

or a pharmaceutically acceptable salt, ester or prodrug thereof.

The present invention further provides pharmaceutical compositions including an effective amount of a compound of formula (I) or pharmaceutically acceptable salts, esters, or prodrugs thereof.

Also provided are methods of increasing an activity of a cholinergic receptor comprising contacting the cholinergic receptor or a system containing the cholinergic receptor with an effective amount of a compound of formula (I), as well as kits for performing the same. Preferably, the receptor is a muscarinic receptor of the m1 or m4 subtype. The receptor may be located in the central nervous system, peripheral nervous system, gastrointestinal system, heart, endocrine glands, or lungs; and the receptor may be a truncated, mutated, or modified cholinergic receptor.

Furthermore, the present invention relates to a method of activating a cholinergic receptor comprising contacting the cholinergic receptor or a system containing the cholinergic receptor with an effective amount of at least one compound of formula (I), as well as kits for performing the method. In a preferred embodiment, the compound is selective for the m1 or m4 muscarinic receptor subtype, or both. In another preferred embodiment, the compound has little or substantially no effect on m2 or m3 activity.

Another aspect of the present invention relates to a method of treating a disease condition associated with a cholinergic receptor comprising administering to a subject in need of such treatment an effective amount of at least one of the compounds of the invention. Kits for performing the method are also provided. The disease conditions that are treated include, but are not limited to conditions of cognitive dysfunction, forgetfulness, confusion, memory loss, attention deficits, deficits in visual perception, depression, pain, sleep disorders, and psychosis. The disease conditions also include, but are not limited to diseases of Alzheimer's disease, Parkinson's disease, Huntington's chorea, Friederich's ataxia, Gilles de la Tourette's Syndrome, Down Syndrome, Pick disease, dementia pugilistica, clinical depression, age-related cognitive decline, attention-deficit disorder, and sudden infant death syndrome.

Further provided are methods of treating the symptoms of a disease or condition associated with reduced levels of acetylcholine comprising administering an effective amount of at least one compound of the invention.

In yet another embodiment, the present invention provides a method of treating Alzheimer's disease. The method comprises administering to a subject in need of such treatment an effective amount of at least one compound of the invention.

In still another embodiment, the present invention provides a method of treating glaucoma. The method comprises administering an effective amount of at least one compound of the invention.

Another aspect of the present invention is a method for identifying a genetic polymorphism predisposing a subject to being responsive to a compound of the invention. The method comprises administering to a subject a therapeutically effective amount of the compound; measuring the response of said subject to the compound, thereby identifying a responsive subject having an ameliorated disease condition associated with a cholinergic receptor; and identifying a genetic polymorphism in the responsive subject, wherein the genetic polymorphism predisposes a subject to being responsive to the compound.

The present invention also features a method for identifying a subject suitable for treatment with a compound of the invention, and kits for identifying the same. The method comprises detecting the presence of a polymorphism in a subject wherein the polymorphism predisposes the subject to being responsive to the compound, and wherein the presence of the polymorphism indicates that the subject is suitable for treatment with the compound.

DETAILED DESCRIPTION OF THE INVENTION

Definitions

For the purpose of the current disclosure, the following definitions shall in their entireties be used to define technical terms and to define the scope of the composition of matter for which protection is sought in the claims.

A "receptor" is intended to include any molecule present inside or on the surface of a cell that may affect cellular physiology when it is inhibited or stimulated by a ligand. Typically, a receptor comprises an extracellular domain with ligand-binding properties, a transmembrane domain that anchors the receptor in the cell membrane, and a cytoplasmic domain that generates a cellular signal in response to ligand binding ("signal transduction"). A receptor also includes any molecule having the characteristic structure of a receptor, but with no identifiable ligand. In addition, a receptor includes a truncated, modified, mutated receptor, or any molecule comprising partial or all of the sequences of a receptor.

"Ligand" is intended to include any substance that interacts with a receptor.

"Agonist" is defined as a compound that increases the activity of a receptor when it interacts with the receptor.

The "m1 receptor" is defined as a receptor having an activity corresponding to the activity of the m1 muscarinic receptor subtype characterized through molecular cloning and pharmacology.

"Selective" or "selectivity" is defined as a compound's ability to generate a desired response from a particular receptor type, subtype, class or subclass while generating less or little response from other receptor types. "Selective" or "selectivity" of an m1 or m4 muscarinic agonist compound means a compound's ability to increase the activity of the m1 or m4 muscarinic receptor, respectively, while causing little or no increase in the activity of other subtypes including m3 and m5 subtypes, and preferably the m2 subtype. Compounds of the presents invention may also show selectivity toward both m1 and m4 receptors, i.e. increase the activity of both the m1 and m4 muscarinic receptors, while causing little or no increase in the activity of other subtypes including the m3 and m5 subtypes, and preferably the m2 subtype.

The term "subject" refers to an animal, preferably a mammal or a human, who is the object of treatment, observation or experiment.

As used herein, "coadministration" of pharmacologically active compounds refers to the delivery of two or more separate chemical entities, whether in vitro or in vivo. Coadministration means the simultaneous delivery of separate agents; the simultaneous delivery of a mixture of agents; as well as the delivery of one agent followed by delivery of a second agent or additional agents. Agents that are coadministered are typically intended to work in conjunction with each other.

The term "an effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

"Alkyl" means a straight or branched-chain alkane group with 1–6 carbon atoms in the chain, for instance methyl, ethyl, propyl, isopropyl, n-butyl, sec-butyl, tert-butyl, etc. The term "heteroalkyl" is intended to indicate an alkane group containing 1 or 2 heteroatoms selected from O, S or N.

"Alkenyl" means a straight or branched-chain alkene group with 2–6 carbon atoms in the chain; the term "alkynyl" is intended to indicate a straight or branched-chain alkyne group with 2–6 carbon atoms in the chain.

The terms "aryl" and "cycloalkyl" preferably refer to mono- and bicyclic ring structures comprising 5 to 12 carbon atoms, more preferably monocyclic rings comprising 5 to 6 carbon atoms. Where such rings comprise one or more heteroatoms, selected from N, S and O, (i.e., heterocyclic, or heteroaryl rings) such rings comprise a total of 5 to 12 atoms, more preferably 5 to 6 atoms. Heterocyclic rings include, but are not limited to, furyl, pyrrolyl, pyrazolyl, thienyl, imidazolyl, indolyl, benzofuranyl, benzothiophenyl, indazolyl, benzoimidazolyl, benzothiazolyl, isoxazolyl, oxazolyl, thiazolyl, isothiazolyl, pyridyl, piperidinyl, piperazinyl, pyridazinyl, pyrimidinyl, pyrazinyl, morpholinyl, oxadiazolyl, thiadiazolyl, imidazolinyl, imidazolidinyl and the like. The ring may be substituted by one or more of the groups included in the definition of $R_2$ above. It is understood that the substituents $C_{1-6}$ alkyl, $C_{2-6}$ alkenyl, $C_{2-6}$ alkynyl, $C_{1-6}$ alkoxy, $C_{1-6}$ heteroalkyl, $C_{1-6}$ aminoalkyl, $C_{1-6}$ haloalkyl or $C_{1-6}$ alkoxycarbonyl may, if present, be substituted by one or more of hydroxyl, $C_{1-4}$ alkoxy, halogen, cyano, amino or nitro.

As used herein, the term "halogen" or "halo" includes chlorine, fluorine, which are preferred, and iodine and bromine.

The present invention provides compounds that are agonists of cholinergic receptors including muscarinic receptors. Especially, the present invention provides compounds that are selective for the m1 or m4 muscarinic receptor subtype, or both. The compounds provided by the present invention have therapeutic effect and can be used to treat disease conditions associated with cholinergic receptors, e.g., cognitive impairment in Alzheimer's disease, glaucoma, pain, or schizophrenia.

According to one embodiment, the present invention provides compounds of formula (I)

(I)

wherein:

$Z_1$ is $CR_1$ or N, $Z_2$ is $CR_2$ or N, $Z_3$ is $CR_3$ or N, and $Z_4$ is $CR_4$ or N, no more than two of $Z_1$, $Z_2$, $Z_3$ and $Z_4$ being N;

$W_1$ is O, S, or $NR_5$, one of $W_2$ and $W_3$ is N or $CR_6$ and the other of $W_2$ and $W_3$ is CG; $W_1$ is NG, $W_2$ is $CR_5$ or N, and $W_3$ is $CR_6$ or N; or $W_1$ is N, $W_2$ is NG and $W_3$ is N;

G is of formula (II):

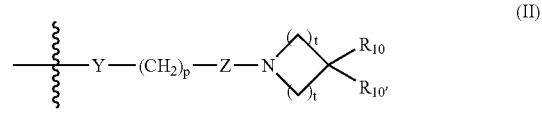

(II)

Y is O, S, CHOH, —NHC(O)—, —C(O)NH—, —C(O)—, —OC(O)—, —(O)CO—, —$NR_7$—, —CH=N—, or absent;

p is 1, 2, 3, 4 or 5;

Z is $CR_8R_9$ or absent;

each t is 1, 2, or 3;

each $R_1$, $R_2$, $R_3$, and $R_4$, independently, is H, amino, hydroxyl, halo, or straight- or branched-chain $C_1$alkyl, $C_{2-6}$ alkenyl, $C_{2-6}$ alkynyl, $C_{1-6}$ heteroalkyl, $C_{1-6}$ haloalkyl, —CN, —$CF_3$, —$OR_{11}$, —$COR_{11}$, —$NO_2$, —$SR_{11}$, —$NHC(O)R_{11}$, —$C(O)NR_{12}R_{13}$, —$NR_{12}R_{13}$, —$NR_{11}C(O)NR_{12}R_{13}$, —$SO_2NR_{12}R_{13}$, —$OC(O)R_{11}$, —$O(CH_2)_qNR_{12}R_{13}$, or —$(CH_2)_qNR_{12}R_{13}$, where q is an integer from 2 to 6, or $R_1$ and $R_2$ together form —NH—N=N— or $R_3$ and $R_4$ together form —NH—N=N—;

each $R_5$, $R_6$, and $R_7$, independently, is H, $C_{1-6}$ alkyl; formyl; $C_{3-6}$ cycloalkyl; $C_{5-6}$ aryl, optionally substituted with halo or $C_{1-6}$ alkyl; or $C_{5-6}$ heteroaryl, optionally substituted with halo or $C_{1-6}$ alkyl;

each $R_8$ and $R_9$, independently, is H or straight- or branched-chain $C_{1-8}$ alkyl;

$R_{10}$ is straight- or branched-chain $C_{1-8}$ alkyl, $C_{2-8}$ alkenyl, $C_{2-8}$ alkynyl, $C_{1-8}$ alkylidene, $C_{1-8}$ alkoxy, $C_{1-8}$ heteroalkyl, $C_{1-8}$ aminoalkyl, $C_{1-8}$ haloalkyl, $C_{1-8}$ alkoxycarbonyl, $C_{1-8}$ hydroxyalkoxy, $C_{1-8}$ hydroxyalkyl, —SH, $C_{1-8}$ alkylthio, —O—$CH_2$—$C_{5-6}$ aryl, —C(O)—$C_{5-6}$ aryl substituted with $C_{1-3}$ alkyl or halo, $C_{5-6}$ aryl, $C_{5-6}$ cycloalkyl, $C_{5-6}$ heteroaryl, $C_{5-6}$ heterocycloalkyl, —$NR_{12}R_{13}$, —$C(O)NR_{12}R_{13}$, —$NR_{11}C(O)$ NR$_{12}$R$_{13}$, —CR$_{11}$R$_{12}$R$_{13}$, —OC(O)R$_{11}$, —(O)(CH$_2$)$_s$NR$_{12}$R$_{13}$ or —(CH$_2$)$_s$NR$_{12}$R$_{13}$, s being an integer from 2 to 8;

R$_{10}$' is H, straight- or branched-chain C$_{1-8}$ alkyl, C$_{2-8}$ alkenyl, C$_{2-8}$ alkynyl, C$_{1-8}$ alkylidene, C$_{1-8}$ alkoxy, C$_{1-8}$ heteroalkyl, C$_{1-8}$ aminoalkyl, C$_{1-8}$ haloalkyl, C$_{1-8}$ alkoxycarbonyl, C$_{1-8}$ hydroxyalkoxy, C$_{1-8}$ hydroxyalkyl, or C$_{1-8}$ alkylthio;

each R$_{11}$, independently, is H, straight- or branched-chain C$_{1-8}$ alkyl, C$_{2-8}$ alkenyl, C$_{2-8}$ alkynyl, C$_{2-8}$ heteroalkyl, C$_{2-8}$ aminoalkyl, C$_{2-8}$ haloalkyl, C$_{1-8}$ alkoxycarbonyl, C$_{2-8}$ hydroxyalkyl, —C(O)—C$_{5-6}$ aryl substituted with C$_{1-3}$ alkyl or halo, C$_{5-6}$ aryl, C$_{5-6}$ heteroaryl, C$_{5-6}$ cycloalkyl, C$_{5-6}$ heterocycloalkyl, —C(O)NR$_{12}$R$_{13}$, —CR$_5$R$_{12}$R$_{13}$, —(CH$_2$)$_t$NR$_{12}$R$_{13}$, t is an integer from 2 to 8; and each R$_{12}$ and R$_{13}$, independently, is H, C$_{1-6}$ alkyl; C$_{3-6}$ cycloalkyl; C$_{5-6}$ aryl, optionally substituted with halo or C$_{1-6}$ alkyl; or C$_{5-6}$ heteroaryl, optionally substituted with halo or C$_{1-6}$ alkyl; or R$_{12}$ and R$_{13}$ together form a cyclic structure;

or a pharmaceutically acceptable salt, ester or prodrug thereof.

According to a preferred series of embodiments, t is 2 and R$_{10}$' is H.

According to one preferred series of embodiments Y is —C(O)—, —NHC(O)—, S, O, —OC(O)— or absent. In another, R$_{10}$ is alkyl, and where Z$_1$ is CR$_1$ or N, Z$_2$ is CR$_2$, Z$_3$ is CR$_3$ or N, and Z$_4$ is CR$_4$. In one embodiment, p is 2. In another, R$_5$ is H or C$_{1-6}$ alkyl.

In one embodiment each R$_1$, R$_2$, R$_3$, and R$_4$, independently, is H, halo, —NO$_2$, or straight- or branched-chain C$_{1-6}$ alkyl, or R$_1$ and R$_2$ together form —NH—N=N— or R$_3$ and R$_4$ together form —NH—N=N—.

Particular embodiments of the invention include:
3-[3-(4-methoxypiperidine)-1-yl-propyl]-1H-indole;
3-[3-(4-ethoxypiperidine)-1-yl-propyl]-1H-indole;
3-[3-(4-propoxypiperidine)-1-yl-propyl]-1H-indole;
3-[3-(4-butoxypiperidine)-1-yl-propyl]-1H-indole;
3-[3-(4-methoxymethylpiperidine)-1-yl-propyl]-1H-indole;
3-[3-(4-ethoxymethylpiperidine)-1-yl-propyl]-1H-indole;
3-[3-(4-propoxymethylpiperidine)-1-yl-propyl]-1H-indole;
3-[3-(4-methylpiperidine)-1-yl-propyl]-1H-indole;
3-[3-(4-ethylpiperidine)-1-yl-propyl]-1H-indole;
3-[3-(4-n-propylpiperidine)-1-yl-propyl]-1H-indole;
3-[3-(4-n-butylpiperidine)-1-yl-propyl]-1H-indole;
3-[2-(4-methoxypiperidine)-1-yl-ethyl]-1H-indole;
3-[2-(4-ethoxypiperidine)-1-yl-ethyl]-1H-indole;
3-[2-(4-propoxypiperidine)-1-yl-ethyl]-1H-indole;
3-[2-(4-butoxypiperidine)-1-yl-ethyl]-1H-indole;
3-[2-(4-methoxymethylpiperidine)-1-yl-ethyl]-1H-indole;
3-[2-(4-ethoxymethylpiperidine)-1-yl-ethyl]-1H-indole;
3-[2-(4-propoxymethylpiperidine)-1-yl-ethyl]-1H-indole;
3-[2-(4-methylpiperidine)-1-yl-ethyl]-1H-indole;
3-[2-(4-ethylpiperidine)-1-yl-ethyl]-1H-indole;
3-[2-(4-n-propylpiperidine)-1-yl-ethyl]-1H-indole;
3-[2-(4-n-butylpiperidine)-1-yl-ethyl]-1H-indole;
3-[2-(4-methoxypiperidine)-1-yl-ethyl]-benzo[d]isoxazole;
3-[2-(4-butoxypiperidine)-1-yl-ethyl]-benzo[d]isoxazole;
3-[3-(4-methoxypiperidine)-1-yl-propyl]-benzo[d]isoxazole;
3-[3-(4-butoxypiperidine)-1-yl-propyl]-benzo[d]isoxazole;
3-[4-(4-methoxypiperidine)-1-yl-butyl]-benzo[d]isoxazole;
3-[4-(4-butoxypiperidine)-1-yl-butyl]-benzo[d]isoxazole;
1-[3-(4-methoxypiperidine)-1-yl-propyl]-1H-indole;
1-[3-(4-ethoxypiperidine)-1-yl-propyl]-1H-indole;
1-[3-(4-propoxypiperidine)-1-yl-propyl]-1H-indole;
1-[3-(4-butoxypiperidine)-1-yl-propyl]-1H-indole;
1-[3-(4-methoxymethylpiperidine)-1-yl-propyl]-1H-indole;
1-[3-(4-ethoxymethylpiperidine)-1-yl-propyl]-1H-indole;
1-[3-(4-propoxymethylpiperidine)-1-yl-propyl]-1H-indole;
1-[3-(4-methylpiperidine)-1-yl-propyl]-1H-indole;
1-[3-(4-ethylpiperidine)-1-yl-propyl]-1H-indole;
1-[3-(4-n-propylpiperidine)-1-yl-propyl]-1H-indole;
1-[3-(4-n-butylpiperidine)-1-yl-propyl]-1H-indole;
1-[2-(4-methoxypiperidine)-1-yl-ethyl]-1H-indole;
1-[2-(4-ethoxypiperidine)-1-yl-ethyl]-1H-indole;
1-[2-(4-propoxypiperidine)-1-yl-ethyl]-1H-indole;
1-[2-(4-butoxypiperidine)-1-yl-ethyl]-1H-indole;
1-[2-(4-methoxymethylpiperidine)-1-yl-ethyl]-1H-indole;
1-[2-(4-ethoxymethylpiperidine)-1-yl-ethyl]-1H-indole;
1-[2-(4-propoxymethylpiperidine)-1-yl-ethyl]-1H-indole;
1-[2-(4-methylpiperidine)-1-yl-ethyl]-1H-indole;
1-[2-(4-ethylpiperidine)-1-yl-ethyl]-1H-indole;
1-[2-(4-n-propylpiperidine)-1-yl-ethyl]-1H-indole;
1-[2-(4-n-butylpiperidine)-1-yl-ethyl]-1H-indole;
1-[3-(4-methoxypiperidine)-1-yl-propyl]-1H-benzotriazole;
1-[3-(4-ethoxypiperidine)-1-yl-propyl]-1H-benzotriazole;
1-[3-(4-propoxypiperidine)-1-yl-propyl]-1H-benzotriazole;
1-[3-(4-butoxypiperidine)-1-yl-propyl]-1H-benzotriazole;
1-[3-(4-methoxymethylpiperidine)-1-yl-propyl]-1H-benzotriazole;
1-[3-(4-ethoxymethylpiperidine)-1-yl-propyl]-1H-benzotriazole;
1-[3-(4-propoxymethylpiperidine)-1-yl-propyl]-1H-benzotriazole;
1-[3-(4-methylpiperidine)-1-yl-propyl]-1H-benzotriazole;
1-[3-(4-ethylpiperidine)-1-yl-propyl]-1H-benzotriazole;
1-[3-(4-n-propylpiperidine)-1-yl-propyl]-1H-benzotriazole;
1-[3-(4-n-butylpiperidine)-1-yl-propyl]-1H-benzotriazole;
1-[2-(4-methoxypiperidine)-1-yl-ethyl]-1H-benzotriazole;
1-[2-(4-ethoxypiperidine)-1-yl-ethyl]-1H-benzotriazole;
1-[2-(4-propoxypiperidine)-1-yl-ethyl]-1H-benzotriazole;
1-[2-(4-butoxypiperidine)-1-yl-ethyl]-1H-benzotriazole;
1-[2-(4-methoxymethylpiperidine)-1-yl-ethyl]-1H-benzotriazole;
1-[2-(4-ethoxymethylpiperidine)-1-yl-ethyl]-1H-benzotriazole;
1-[2-(4-propoxymethylpiperidine)-1-yl-ethyl]-1H-benzotriazole;
1-[2-(4-methylpiperidine)-1-yl-ethyl]-1H-benzotriazole;
1-[2-(4-ethylpiperidine)-1-yl-ethyl]-1H-benzotriazole;
1-[2-(4-n-propylpiperidine)-1-yl-ethyl]-1H-benzotriazole;
1-[2-(4-n-butylpiperidine)-1-yl-ethyl]-1H-benzotriazole;

1-[4-(4-methoxypiperidine)-1-yl-butyl]-1H-benzotriazole;
1-[4-(4-ethoxypiperidine)-1-yl-butyl]-1H-benzotriazole;
1-[4-(4-propoxypiperidine)-1-yl-butyl]-1H-benzotriazole;
1-[4-(4-butoxypiperidine)-1-yl-butyl]-1H-benzotriazole;
1-[4-(4-methoxymethylpiperidine)-1-yl-butyl]-1H-benzotriazole;
1-[4-(4-ethoxymethylpiperidine)-1-yl-butyl]-1H-benzotriazole;
1-[4-(4-propoxymethylpiperidine)-1-yl-butyl]-1H-benzotriazole;
1-[4-(4-methylpiperidine)-1-yl-butyl]-1H-benzotriazole;
1-[4-(4-ethylpiperidine)-1-yl-butyl]-1H-benzotriazole;
1-[4-(4-n-propylpiperidine)-1-yl-butyl]-1H-benzotriazole;
1-[4-(4-n-butylpiperidine)-1-yl-butyl]-1H-benzotriazole;
2-[4-(4-methylpiperidine)-1-yl-butyl]-1H-benzotriazole;
2-[4-(4-ethylpiperidine)-1-yl-butyl]-1H-benzotriazole;
2-[4-(4-n-propylpiperidine)-1-yl-butyl]-1H-benzotriazole;
2-[4-(4-n-butylpiperidine)-1-yl-butyl]-1H-benzotriazole;
2-[3-(4-methylpiperidine)-1-yl-propyl]-1H-benzoimidazole;
2-[3-(4-ethylpiperidine)-1-yl-propyl]-1H-benzoimidazole;
2-[3-(4-n-propylpiperidine)-1-yl-propyl]-1H-benzoimidazole;
2-[3-(4-n-butylpiperidine)-1-yl-propyl]-1H-benzoimidazole;
2-[2-(4-methylpiperidine)-1-yl-ethyl]-1H-benzoimidazole;
2-[2-(4-ethylpiperidine)-1-yl-ethyl]1H-benzoimidazole;
2-[2-(4-n-propylpiperidine)-1-yl-ethyl]-1H-benzoimidazole;
2-[2-(4-n-butylpiperidine)-1-yl-ethyl]-1H-benzoimidazole;
1-(1H-benzoimidazol-2-yl)-4-(4-ethylpiperidine)-butanone;
1-(1H-benzoimidazol-2-yl)-4-(4-ethylpiperidine)-butanone;
1-(1H-benzoimidazol-2-yl)-4-(4-n-propylpiperidine)-butanone;
1-(1H-benzoimidazol-2-yl)-4-(4-n-butylpiperidine)-butanone;
1-(1H-benzoimidazol-2-yl)-3-(4-methylpiperidine)-propanone;
1-(1H-benzoimidazol-2-yl)-3-(4-ethylpiperidine)-propanone;
1-(1H-benzoimidazol-2-yl)-3-(4-n-propylpiperidine)-propanone;
1-(1H-benzoimidazol-2-yl)-3-(4-n-butylpiperidine)-propanone;
3-[3-(4-methylpiperidine)-1-yl-propyl]-1H-indazole;
3-[3-(4-ethylpiperidine)-1-yl-propyl]-1H-indazole;
3-[3-(4-n-propylpiperidine)-1-yl-propyl]-1H-indazole;
3-[3-(4-n-butylpiperidine)-1-yl-propyl]-1H-indazole;
1-(3-benzofuran-3-yl-propyl)-4-methyl-piperidine;
1-(3-benzofuran-3-yl-propyl)-4-ethyl-piperidine;
1-(3-benzofuran-3-yl-propyl)-4-n-propyl-piperidine;
1-(3-benzofuran-3-yl-propyl)-4-n-butyl-piperidine;
3-(3-(4-methylpiperidine)-1-yl-propyl)-benzo[d]isothiazole;
3-(3-(4-ethylpiperidine)-1-yl-propyl)-benzo[d]isothiazole;
3-(3-(4-n-propylpiperidine)-1-yl-propyl)-benzo[d]isothiazole;
3-(3-(4-n-butylpiperidine)-1-yl-propyl)-benzo[d]isothiazole;
1-[3-(4-methylpiperidine)-1-yl-propyl]-1H-benzoimidazole;
1-[3-(4-ethylpiperidine)-1-yl-propyl]-1H-benzoimidazole;
1-[3-(4-n-propylpiperidine)-1-yl-propyl]-1H-benzoimidazole;
1-[3-(4-n-butylpiperidine)-1-yl-propyl]-1H-benzoimidazole;
1-[2-(4-methylpiperidine)-1-yl-ethyl]-1H-benzoimidazole;
1-[2-(4-ethylpiperidine)-1-yl-ethyl]-1H-benzoimidazole;
1-[2-(4-n-propylpiperidine)-1-yl-ethyl]-1H-benzoimidazole;
1-[2-(4-n-butylpiperidine)-1-yl-ethyl]-1H-benzoimidazole;
1-[3-(4-methylpiperidine)-1-yl-propyl]-1H-indazole;
1-[3-(4-ethylpiperidine)-1-yl-propyl]-1H-indazole;
1-[3-(4-n-propylpiperidine)-1-yl-propyl]-1H-indazole;
1-[3-(4-n-butylpiperidine)-1-yl-propyl]-1H-indazole;
2-[4-(4-methylpiperidine)-1-yl-butyl]-1H-benzothiazole;
2-[4-(4-ethylpiperidine)-1-yl-butyl]-1H-benzothiazole;
2-[4-(4-n-propylpiperidine)-1-yl-butyl]-1H-benzothiazole;
2-[4-(4-n-butylpiperidine)-1-yl-butyl]-1H-benzothiazole;
2-[3-(4-methylpiperidine)-1-yl-propyl]-1H-benzothiazole;
2-[3-(4-ethylpiperidine)-1-yl-propyl]-1H-benzothiazole;
2-[3-(4-n-propylpiperidine)-1-yl-propyl]-1H-benzothiazole;
2-[3-(4-n-butylpiperidine)-1-yl-propyl]-1H-benzothiazole;
2-[2-(4-methylpiperidine)-1-yl-ethyl]-1H-benzothiazole;
2-[2-(4-ethylpiperidine)-1-yl-ethyl]-1H-benzothiazole;
2-[2-(4-n-propylpiperidine)-1-yl-ethyl]-1H-benzothiazole;
2-[2-(4-n-butylpiperidine)-1-yl-ethyl]-1H-benzothiazole;
2-[3-(4-methylpiperidine)-1-yl-propyl]-benzooxazole;
2-[3-(4-ethylpiperidine)-1-yl-propyl]-benzooxazole;
2-[3-(4-n-propylpiperidine)-1-yl-propyl]-benzooxazole;
2-[3-(4-n-butylpiperidine)-1-yl-propyl]-benzooxazole;
2-[2-(4-methylpiperidine)-1-yl-ethyl]-benzooxazole;
2-[2-(4-ethylpiperidine)-1-yl-ethyl]-benzooxazole;
2-[2-(4-n-propylpiperidine)-1-yl-ethyl]-benzooxazole;
2-[2-(4-n-butylpiperidine)-1-yl-ethyl]-benzooxazole;
2-[4-(4-methylpiperidine)-1-yl-butyl]-benzooxazole;
2-[4-(4-ethylpiperidine)-1-yl-butyl]-benzooxazole;
2-[4-(4-n-propylpiperidine)-1-yl-butyl]-benzooxazole;
2-[4-(4-n-butylpiperidine)-1-yl-butyl]-benzooxazole;
4,5-difluoro-2-(3-(4-n-butylpiperidine-1-yl)-propyl)-1H-benzoimidazole;
6-fluoro-5-nitro-2-(3-(4-n-butylpiperidine-1-yl)-propyl)-1H-benzoimidazole;
5-tert-butyl-2-(3-(4-n-butylpiperidine-1-yl)-propyl)-1H-benzoimidazole;
5-chloro-6-methyl-2-(3-(4-n-butylpiperidine-1-yl)-propyl)-1H-benzoimidazole;
4,6-difluoro-2-(3-(4-n-butylpiperidine-1-yl)-propyl)-1H-benzoimidazole;
2-3-(4-n-butylpiperidine)-1-yl-propyl)-1H-imidazo[4,5-c]pyridine;
8-(3-(4-n-butylpiperidine)-1-yl-propyl)-9H-purine;
7-(3-(4-n-butylpiperidine)-1-yl-propyl)-3,8-dihydro-imidazo[4',5':3,4]benzo[1,2-d][1,2,3]triazole;
2-(3-(4-n-butylpiperidine)-1-yl-propyl)-3a,4,5,6,7,7a-hexahydro-1H-benzoimidazole;

3-methyl-1-(3-(4-n-butylpiperidine)-1-yl-propyl)-1H-indole;
5-bromo-1-(3-(4-n-butylpiperidine)-1-yl-propyl)-1H-indole;
3-formyl-1-(3-(4-n-butylpiperidine)-1-yl-propyl)-1H-indole;
7-bromo-1-(3-(4-n-butylpiperidine)-1-yl-propyl)-1H-indole;
3-(3-(4-n-butylpiperidine)-1-yl-propyl)-benzo[d]isoxazole;
4-nitro-2-(3-(4-n-butylpiperidine)-1-yl-propyl)-1H-benzoimidazole;
5-nitro-2-(3-(4-n-butylpiperidine)-1-yl-propyl)-1H-benzoimidazole
4-hydroxy-2-(3-(4-n-butylpiperidine)-1-yl-propyl)-1H-benzoimidazole;
4-methyl-2-(3-(4-n-butylpiperidine)-1-yl-propyl)-1H-benzoimidazole;
3-(2-(4-n-Butylpiperidine)-ethoxy)-7-methyl-benzo[d]isoxazole;
1-(3-(4-Methylpiperidine)-1-yl-propyl)-1H-indazole;
1-(3-(4-Pentylpiperidine)-1-yl-propyl)-1H-indazole;
1-(3-(4-Propylpiperidine)-1-yl-propyl)-1H—;
1-(3-(4-(3-Methyl-butyl)-piperidine)-1-yl-propyl)-1H-indazole
1-(3-(4-Pentylidene-piperidine)-1-yl-propyl)-1H-indazole;
1-(3-(4-Propylidene-piperidine)-1-yl-propyl)-1H-indazole 1-Benzo[b]thiophen-2-yl-4-(4-butylpiperidin-1-yl)-butan-1-one
4-(4-Butylpiperidin-1-yl)-1-(3-methyl-benzofuran-2-yl)-butan-1-one;
4-(4-Butylpiperidin-1-yl)-1-(5-fluoro-3-methyl-benzo[b]thiophen-2-yl)-butan-1-one;
1-Benzofuran-2-yl-4-(4-butylpiperidin-1-yl)-butan-1-one;
1-(3-Bromo-benzo[b]thiophen-2-yl)-4-(4-butylpiperidin-1-yl)-butan-1-one
1-(3-Benzo[b]thiophen-2-yl-propyl)-4-butylpiperidine;
1-(3-Benzofuran-2-yl-propyl)-4-butylpiperidine;
4-Butyl-1-[3-(3-methyl-benzofuran-2-yl)-propyl]-piperidine;
4-Butyl-1-[3-(5-fluoro-3-methyl-benzo[b]thiophen-2-yl)-propyl]-piperidine;
2-(3-Iodo-propyl)-benzo[b]thiophene;
1-(3-Benzo[b]thiophen-2-yl-propyl)-4-methylpiperidine
1-(3-Benzo[b]thiophen-2-yl-propyl)-4-benzylpiperidine;
1-(3-Benzo[b]thiophen-2-yl-propyl)-4-(2-methoxy-phenyl)-piperidine;
2-(3-Bromopropyl)-2H-benzotriazole;
2-[3-(4-Butylpiperidin-1-yl)-propyl]-2H-benzotriazole;
1-(3-Bromopropyl)-1H-benzotriazole;
1-[3-(4-Butylpiperidin-1-yl)-propyl]-1H-benzotriazole;
1-[3-(4-Butylpiperidin-1-yl)-propyl]-1H-indole-3-carbaldehyde;
{1-[3-(4-Butylpiperidin-1-yl)-propyl]-1H-indol-3-yl}-methanol;
1-[3-(4-Butylpiperidin-1-yl)-propyl]-2-phenyl-1H-benzoimidazole;
1-[3-(4-Butylpiperidin-1-yl)-propyl]-3-chloro-1H-indazole;
1-[3-(4-Butylpiperidin-1-yl)-propyl]-6-nitro-1H-indazole;
Benzo[d]isoxazol-3-ol;
3-(2-Chloroethoxy)-benzo[d]isoxazole;
3-[2-(4-Butylpiperidin-1-yl)-ethoxy]-benzo[d]isoxazol;
3-(1H-Indol-3-yl)-propan-1-ol;
3-[3-(4-Butyl-piperidin-1-yl)-propyl]-1H-indole hydrochloride;
4-(4-Butylpiperidine-1-yl)-butyric acid methyl ester;
2-[3-(4-Butylpiperidin-1-yl)-propyl]-1-methyl-1H-benzimidazole;
1H-Indazole-3-carboxylic acid (2-(4-butylpiperidin)-1-yl-ethyl)-amide;
1-[3-(4-Butylpiperidin-1-yl)-propyl]-5-nitro-1H-indazole;
2-[3-(4-butylpiperidin-1-yl)-propyl]-5-nitro-2H-indazole;
1-[3-(4-Butylpiperidin-1-yl)-propyl]-2-methyl-1H-indole;
1-{1-[3-(4-Butyl-piperidin-1-yl)-propyl]-1H-indol-3-yl}-ethanone;
{1-[3-(4-Butyl-piperidin-1-yl)-propyl]-1H-indol-3-yl}-acetonitrile;
1-[3-(4-Butyl-piperidin-1-yl)-propyl]-1H-indole-3-carbonitrile;
1-[3-(4-Butyl-piperidin-1-yl)-propyl]-5,6-dimethyl-1H-benzoimidazole;
1-[3-(4-Butyl-piperidin-1-yl)-propyl]-5(6)-dimethyl-1H-benzoimidazole;
1-[3-(4-Butyl-piperidin-1-yl)-propyl]-5-methoxy-1H-benzoimidazole;
{1-[3-(4-Butyl-piperidin-1-yl)-propyl]-1H-benzoimidazol-2-yl}-methanol;
1-[3-(4-Butyl-piperidin-1-yl)-propyl]-2-trifluoromethyl-1H-benzoimidazole;
(2-Trimethylstannanyl-phenyl)-carbamic acid tert-butyl ester;
[2-(4-Chloro-butyryl)-phenyl]-carbamic acid tert-butyl ester;
{2-[4-(4-Butyl-piperidine-1-yl)-butyryl]-phenyl}-carbamic acid tert-butyl ester;
3-[3-(4-Butyl-piperidine-1-yl)-propyl]-1H-indazole, HCl;
3-[3-(4-Butyl-piperidine-1-yl)-propyl]-5-nitro-1H-indazole;
3-[3-(4-Butyl-piperidine-1-yl)-propyl]-5,7-dinitro-1H-indazole;
4-(4-Butyl-piperidin-1-yl)-1-(2-metylsulfanyl-phenyl)-butan-1-one;
3-[3-(4-Butyl-piperidin-1-yl)-propyl]-benzo[d]isothiazole;
3-[3-(4-Butyl-piperidin-1-yl)-propyl]-5-methoxy-1H-indazole;
3-[3-(4-Butyl-piperidin-1-yl)-propyl]-4-methoxy-1H-indazole
3-[3-(4-Butyl-piperidin-1-yl)-propyl]-6-methoxy-1H-indazole;
3-[3-(4-Butyl-piperidin-1-yl)-propyl]-1H-indazole-4-ol (53MF51);
3-[3-(4-Butyl-piperidin-1-yl)-propyl]-1H-indazole-6-ol (53MF52); and
3-[3-(4-Butyl-piperidin-1-yl)-propyl]-1H-indazole-5-ol The present invention further provides pharmaceutical compositions comprising an effective amount of at least one compound of the invention, inclusive of all compounds within the scope of formula (I).

In general, compounds of the present invention are active at cholinergic, specifically muscarinic receptors. Preferred compounds share the common property of acting as agonists at the m1 or m4 muscarinic receptor subtypes, or both. In a preferred embodiment, the compounds of the present invention are selective towards the m1, m4, or both the m1 and m4 subtypes of muscarinic receptors, i.e., the compounds have less or substantially no effect on other subtypes of the muscarinic receptors. Typically, the m1 and/or m4 selective compounds of the invention have no effect on other related receptors, including G-protein coupled receptors, e.g., serotonin, histamine, dopamine or adrenergic receptors. The invention provides compounds that are selective as agonists at either the m1 or the m4 subtype as well as compounds that are agonists at both the m1 and m4 receptor subtypes. In one embodiment, the compounds of the present invention have less or substantially no effect on m2 and m3 subtypes of muscarinic receptors. In another embodiment, the compounds of the present invention have less or substantially no effect on m2, m3, m4, and m5 subtypes of muscarinic receptors.

The compounds of present invention typically have therapeutic effects and can be used to treat or alleviate symptoms of disease conditions associated with cholinergic receptors such as cognitive impairment, forgetfulness, confusion, memory loss, attentional deficits, deficits in visual perception, depression, pain, sleep disorders, psychosis, hallucinations, aggressiveness, paranoia, and increased intraocular pressure. The disease condition may result from dysfunction, decreased activity, modification, mutation, truncation, or loss of cholinergic receptors, especially muscarinic receptors, as well as from reduced levels of acetylcholine.

The compounds of present invention can also be used to treat diseases, e.g., age-related cognitive decline, Alzheimer's disease, Parkinson's disease, Huntington's chorea, Friederich's ataxia, Gilles de la Tourette's Syndrome, Down Syndrome, Pick disease, dementia, clinical depression, age-related cognitive decline, attention-deficit disorder, sudden infant death syndrome, and glaucoma.

The compounds of the present invention have the ability to increase cholinergic receptor activity or activate cholinergic receptors. Cholinergic receptor activity includes signaling activity or any other activity that is directly or indirectly related to cholinergic signaling or activation. The cholinergic receptors include muscarinic receptors, especially the m1 or m4 subtype of muscarinic receptors. The muscarinic receptor can be, for example, in the central nervous system, peripheral nervous system, gastrointestinal system, heart, endocrine glands, or lungs. The muscarinic receptor can be a wild-type, truncated, mutated, or modified cholinergic receptor. Kits comprising the compounds of the present invention for increasing cholinergic receptor activity or activating cholinergic receptors are also contemplated by the present invention.

The system containing the cholinergic receptor may, for example, be a subject such as a mammal, non-human primate or a human. The system may also be an in vivo or in vitro experimental model, such as a cell culture model system that expresses a cholinergic receptor, a cell-free extract thereof that contains a cholinergic receptor, or a purified receptor. Non-limiting examples of such systems are tissue culture cells expressing the receptor, or extracts or lysates thereof. Cells that may be used in the present method include any cells capable of mediating signal transduction via cholinergic receptors, especially the m1 muscarinic receptor, either via endogenous expression of this receptor (certain types of neuronal cells lines, for example, natively express the m1 receptor), or such as following introduction of the an exogenous gene into the cell, for example, by transfection of cells with plasmids containing the receptor gene. Such cells are typically mammalian cells (or other eukaryotic cells, such as insect cells or Xenopus oocytes), because cells of lower life forms generally lack the appropriate signal transduction pathways for the present purpose. Examples of suitable cells include: the mouse fibroblast cell line NIH 3T3 (ATCC CRL 1658), which responds to transfected m1 receptors by increased growth; RAT 1 cells (Pace et al., Proc. Natl. Acad. Sci. USA 88:7031–35 (1991)); and pituitary cells (Vallar et al., Nature 330:556–58 (1987)). Other useful mammalian cells for the present method include but are not limited to HEK 293 cells, CHO cells and COS cells.

The compounds of the present invention also have the ability to reduce intraocular pressure and therefore can be used in the treatment of such diseases as glaucoma. Glaucoma is a disease in which an abnormality is observed in the circulation-control mechanism of the aqueous humor filling up the anterior chamber, i.e., the space formed between the cornea and the lens. This leads to an increase in the volume of the aqueous humor and an increase in intraocular pressure, consequently leading to visual field defects and even to loss of eyesight due to the compulsion and contraction of the papillae of the optic nerve.

The present invention also pertains to the field of predictive medicine in which pharmacogenomics is used for prognostic (predictive) purposes. Pharmacogenomics deals with clinically significant hereditary variations in the response to drugs due to altered drug disposition and abnormal action in affected persons (see e.g., Eichelbaum, *Clin Exp Pharmacol. Physiol.*, 23:983–985 (1996) and Linder, *Clin. Chem.* 43:254–66 (1997)). In general, two types of pharmacogenetic conditions can be differentiated: genetic conditions transmitted as a single factor altering the way drugs act on the body (altered drug action) or genetic conditions transmitted as single factors altering the way the body acts on drugs (altered drug metabolism). These pharmacogenetic conditions can occur as naturally-occurring polymorphisms.

One pharmacogenomics approach to identifying genes that predict drug response, known as "a genome-wide association", relies primarily on a high-resolution map of the human genome consisting of known gene-related markers (e.g., a "bi-allelic" gene marker map that consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1,000 bases of DNA. A SNP may be involved in a disease process although the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach" can be utilized to identify genes that predict drug response. According to this method, if a gene that encodes a drug's target is known (e.g., a protein or a receptor of the present invention), all common variants of that gene can be identified in the population. It can be readily determined by standard techniques a particular version of the gene is associated with a particular drug response.

Alternatively, a method termed "gene expression profiling" can be utilized to identify genes that predict drug response. For example, the gene expression of an animal dosed with a drug (e.g., a compound or composition of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a compound or composition of the invention, such as a modulator identified by one of the exemplary screening assays described herein. These approaches can also be used to identify novel candidate receptor or other genes suitable for further pharmacological characterization in vitro and in vivo.

Accordingly, another aspect of the present invention features methods and kits for identifying a genetic polymorphism predisposing a subject to being responsive to a compound described herein. The method comprises administering to a subject an effective amount of a compound; identifying a responsive subject having an ameliorated disease condition associated with a cholinergic receptor; and identifying a genetic polymorphism in the responsive subject, wherein the genetic polymorphism predisposes a subject to being responsive to the compound. Identifying a genetic polymorphism in the responsive subject can be performed by any means known in the art including the methods discussed above. In addition, a kit to be used for identifying a genetic polymorphism predisposing a subject to being responsive to a compound provided in the present invention comprises the compound of the present invention, and preferably reagents and instructions for performing a genetic polymorphism test.

In one embodiment, a subject can be tested for a known polymorphism that predisposes the subject to being responsive to the compound of the present invention. The presence of the polymorphism indicates that the subject is suitable for treatment.

In preferred embodiments, the compounds of the present invention can be represented as shown in formulae (IIIa–e):

(IIIa)

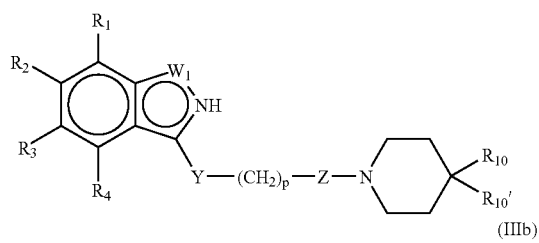

(IIIb)

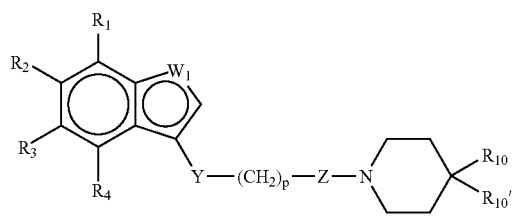

(IIIc)

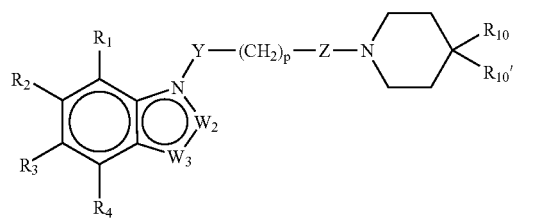

(IIId)

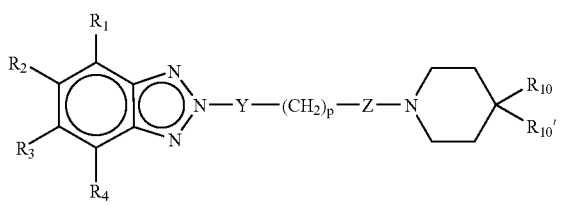

(IIIe)

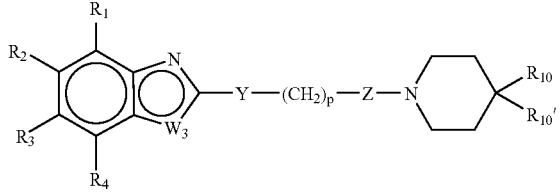

where $W_1$ is O, S, or $NR_5$, $W_2$ is $CR_5$ or N, and $W_3$ is $CR_5$ or N, or wherein $W_3$ is $NR_5$, S or O, or a pharmaceutically acceptable salt, ester or prodrug thereof.

Compounds of the present invention may be prepared by methods analogous to the methods disclosed in G.B. Patent No. 1,142,143 and U.S. Pat. No. 3,816,433, each of which are incorporated herein by reference. Ways of modifying those methods to include other reagents etc. will be apparent to those skilled in the art. Thus, for instance, compounds of formula (III, e.g., IIIb where $W_1$ is $NR_5$) may be prepared as shown in the following reaction scheme.

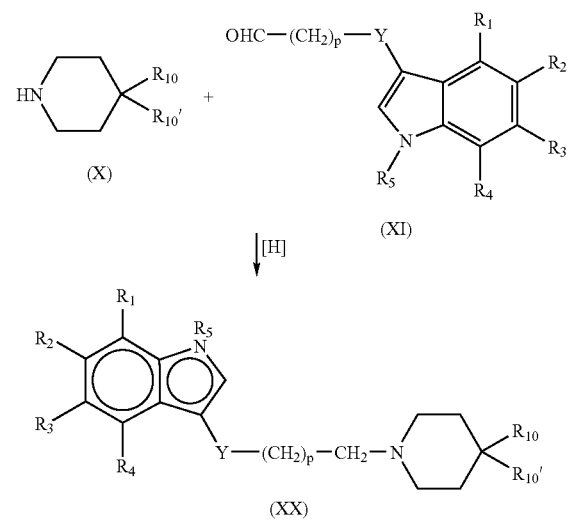

The starting compound having formula (X) may be prepared by general methods of organic synthesis. For general methods of preparing compounds of formula (X), reference is made to Fuller, et al., *J. Med. Chem.* 14:322–325 (1971);

Foye, et al., *J. Pharm. Sci.* 68:591–595 (1979); Bossier, et al., *Chem. Abstr.* 66:46195h and 67:21527a (1967); Aldous, *J. Med. Chem.* 17:1100–1111 (1974); Fuller, et al., *J. Pharm. Pharmacol.* 25:828–829 (1973); Fuller, et al., *Neuropharmacology* 14:739–746 (1975); Conde, et al., *J. Med. Chem.* 21:978–981 (1978); Lukovits, et al., *Int. J. Quantum Chem.* 20:429–438 (1981); and Law, *Cromatog.* 407:1–18 (1987), the disclosures of which are incorporated by reference herein in their entirety. Compounds of formula XI are prepared, for example, as described in Darbre, et al., *Helv. Chim. Acta*, 67:1040–1052 (1984) or Ihara, et al., *Heterocycles*, 20:421–424 (1983), also incorporated herein by reference. The radiolabelled derivatives having formula (XX) may be prepared by, for example, using a tritiated reducing agent to form the reductive amination or by utilizing a $^{14}C$-labelled starting material.

Compounds of formula (XXII) can be used to prepare the compounds of formula (I). Compounds of formula (XXII) are prepared, for example, as described in Ishii, et al., *J. Org. Chem.* 61:3088–3092 (1996) or Britton, et al. *Bioorg. Med. Chem. Lett.* 9:475–480 (1999), also incorporated herein by reference. Where the starting compound includes a carbonyl group, the compound having the formula (XXII) may be reduced with, for example, $AlH_3$, diborane:methyl sulfide or other standard carbonyl reducing reagents to produce the ligand having the formula (XXX).

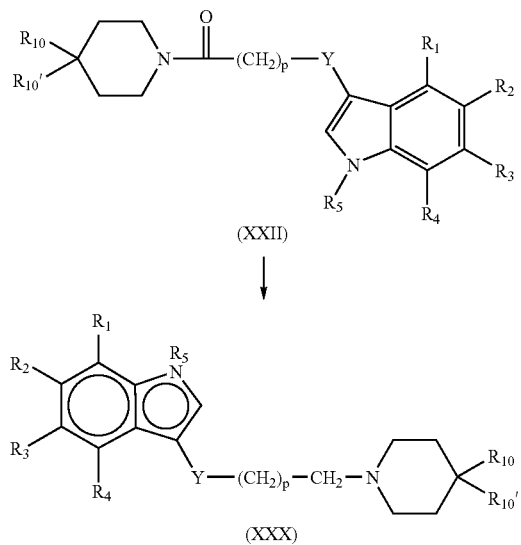

The receptor ligands having formula (XXXII) may be prepared by nucleophilic displacement of a suitable nucleophuge (E) by the amino derivative (XXXI). Examples of nucleophuges, which may be used for this purpose, include halides such as I, Cl, Br, or tosylate or mesylate.

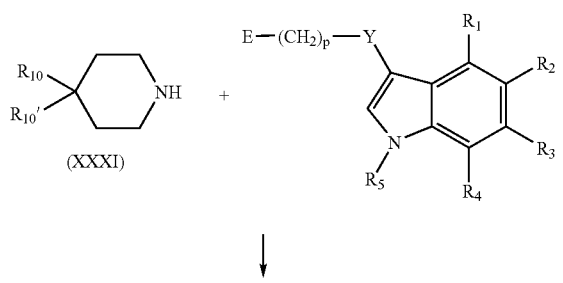

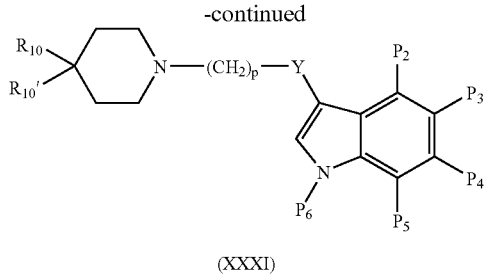

When Y in formula (XXX) is —C(O)—, this compound may be prepared from oxidation of a secondary alcohol with, for example, pyridinium chlorochromate, N-chlorosuccinimide, $CrO_3$—$H_2SO_4$, or via the Swern or Dess-Martin procedures—nickel.

When Y in formula (XXX) is —O—, this compound may be prepared by arylation of an alcohol with arylhalides under, for example, Cu catalysis.

When Y in formula (XXX) is —S—, this compound may be prepared by arylation of a thiol with arylhalides under, for example, Cu catalysis.

When Y in formula (XXX) is —CHOH—, this compound may be prepared by reduction of the corresponding ketone by catalytic hydrogenation or by the use of $NaBH_4$ or by the use of $LiAlH_4$.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Examples of pharmaceutically acceptable salts include the acetate, benzenesulfonate, benzoate, bicarbonate, bisulfate, bitartrate, borate, bromide, calcium, carbonate, chloride, clavulanate, citrate, dihydrochloride, fumarate, gluconate, glutamate, hydrobromide, hydrochloride, hydroxynaphthoate, iodide, isothionate, lactate, lactobionate, laurate, maleate, mandelate, mesylate, methylbromide, methylnitrate, methylsulfate, nitrate, N-methylglucamine ammonium sal, oleate, oxalate, phosphate/diphosphate, salicylate, stearate, sulfate, succinate, tannate, tartrate, tosylate, triethiodide and valerate salt.

The present invention includes within its scope prodrugs of the compounds of this invention. In general, such prodrugs are derivatives of the compounds of this invention, which are readily convertible in vivo into the required compound. Conventional procedures for the selection and preparation of suitable prodrug derivatives are described, for example, in *Design of Prodrugs*, (Bundgaard, ed. Elsevier, 1985). Metabolites of these compounds include active species produced upon introduction of compounds of this invention into the biological milieu.

Where the compounds according to the invention have at least one chiral center, they may exist as a racemate or as enantiomers. It should be noted that all such isomers and mixtures thereof are included in the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also included in the scope of this invention.

Where the processes for the preparation of the compounds according to the invention give rise to mixtures of stereoisomers, such isomers may be separated by conventional techniques such as preparative chiral chromatography. The compounds may be prepared in racemic form, or individual enantiomers may be prepared either by stereoselective synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry* (McOmie ed., Plenum Press, 1973); and Greene & Wuts, *Protective Groups in Organic Synthesis* (John Wiley & Sons, 1991) The protecting groups may be removed at a convenient subsequent stage using methods known from the art.

Compounds of the present invention may be administered in any of the foregoing compositions and according to dosage regimens established in the art whenever specific pharmacological modification of the activity of muscarinic receptors is required.

The present invention also provides pharmaceutical compositions comprising one or more compounds of the invention together with a pharmaceutically acceptable diluent or excipient. Preferably such compositions are in unit dosage forms such as tablets, pills, capsules (including sustained-release or delayed-release formulations), powders, granules, elixirs, tinctures, syrups and emulsions, sterile parenteral solutions or suspensions, aerosol or liquid sprays, drops, ampoules, auto-injector devices or suppositories; for oral, parenteral (e.g., intravenous, intramuscular or subcutaneous), intranasal, sublingual or rectal administration, or for administration by inhalation or insufflation, and may be formulated in an appropriate manner and in accordance with accepted practices such as those disclosed in *Remington's Pharmaceutical Sciences* (Gennaro, ed., Mack Publishing Co., Easton Pa., 1990). Alternatively, the compositions may be in sustained-release form suitable for once-weekly or once-monthly administration; for example, an insoluble salt of the active compound, such as the decanoate salt, may be adapted to provide a depot preparation for intramuscular injection. The present invention also contemplates providing suitable topical formulations for administration to, e.g., eye, skin or mucosa.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents, flavoring agents and coloring agents can also be incorporated into the mixture. Suitable binders include, without limitation, starch, gelatin, natural sugars such as glucose or beta-lactose, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For preparing solid compositions such as tablets, the active ingredient is mixed with a suitable pharmaceutical excipient, e.g., such as the ones described above, and other pharmaceutical diluents, e.g., water, to form a solid preformulation composition containing a homogeneous mixture of a compound of the present invention, or a pharmaceutically acceptable salt thereof. By the term "homogeneous" is meant that the active ingredient is dispersed evenly throughout the composition so that the composition may be readily subdivided into equally effective unit dosage forms such as tablets, pills and capsules. The solid preformulation composition may then be subdivided into unit dosage forms of the type described above containing from about 0.01 to about 50 mg of the active ingredient of the present invention. The tablets or pills of the present composition may be coated or otherwise compounded to provide a dosage form affording the advantage of prolonged action. For example, the tablet or pill can comprise an inner core containing the active compound and an outer layer as a coating surrounding the core. The outer coating may be an enteric layer, which serves to resist disintegration in the stomach and permits the inner core to pass intact into the duodenum or to be delayed in release. A variety of materials can be used for such enteric layers or coatings, such materials including a number of polymeric acids and mixtures of polymeric acids with conventional materials such as shellac, cetyl alcohol and cellulose acetate.

The liquid forms in which the present compositions may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical carriers. Suitable dispersing or suspending agents for aqueous suspensions include synthetic and natural gums such as tragacanth, acacia, alginate, dextran, sodium carboxymethylcellulose, gelatin, methylcellulose or polyvinyl-pyrrolidone. Other dispersing agents, which may be employed, include glycerin and the like. For parenteral administration, sterile suspensions and solutions are desired. Isotonic preparations, which generally contain suitable preservatives, are employed when intravenous administration is desired. The compositions can also be formulated as an ophthalmic solution or suspension formation, i.e., eye drops, for ocular administration Compounds of the present invention may be administered in a single daily dose, or the total daily dosage may be administered in divided doses two, three or four times daily. Furthermore, compounds of the present invention may be administered in intranasal form via topical use of suitable intranasal vehicles or via transdermal routes, using e.g., forms of transdermal skin patches that are well known to persons skilled in the art. To be administered in the form of a transdermal delivery system, the dosage administration will be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound employed. A physician or veterinarian of ordinary skill can readily determine and prescribe the effective amount of the drug required to prevent, counter or arrest the progress of the disease or disorder, which is being treated.

The daily dosage of the products may be varied over a wide range from 0.01 to 100 mg per adult human per day. For oral administration, the compositions are preferably provided in the form of tablets containing 0.01, 0.05, 0.1, 0.5, 1.0, 2.5, 5.0, 10.0, 15.0, 25.0 or 50.0 mg of the active ingredient for the symptomatic adjustment of the dosage to the patient to be treated. A unit dose typically contains from about 0.001 mg to about 50 mg of the active ingredient, preferably from about 1 mg to about 10 mg of active ingredient. An effective amount of the drug is ordinarily supplied at a dosage level of from about 0.0001 mg/kg to about 25 mg/kg of body weight per day. Preferably, the range is from about 0.001 to 10 mg/kg of body weight per day, and especially from about 0.001 mg/kg to 1 mg/kg of body weight per day. The compounds may be administered, for example, on a regimen of 1 to 4 times per day.

Compounds according to the present invention may be used alone at appropriate dosages defined by routine testing in order to obtain optimal pharmacological effect on a muscarinic receptor, in particular the muscarinic m1 or m4 receptor subtype, while minimizing any potential toxic or otherwise unwanted effects. In addition, co-administration or sequential administration of other agents that improve the effect of the compound may, in some cases, be desirable.

The pharmacological properties and the selectivity of the compounds of this invention for specific muscarinic receptor subtypes may be demonstrated by a number of different assay methods using, for example, recombinant receptor subtypes, preferably of the human receptors as available, e.g., conventional second messenger or binding assays. A particularly convenient functional assay system is the receptor selection and amplification assay disclosed in U.S. Pat. No. 5,707,798, which describes a method of screening for bioactive compounds by utilizing the ability of cells transfected with receptor DNA, e.g., coding for the different muscarinic subtypes, to amplify in the presence of a ligand of the receptor. Cell amplification is detected as increased levels of a marker also expressed by the cells.

The invention is disclosed in further detail in the following examples, which are not in any way intended to limit the scope of the invention as claimed.

EXAMPLES

Methods of Preparation

The compounds in accordance with the present invention may be synthesized by methods described below, or by modification of these methods. Ways of modifying the methodology include, for example, temperature, solvent, reagents etc, will be apparent to those skilled in the art.

General LC-MS procedure: All spectra were obtained using an HP1100 LC/MSD-instrument. A setup with a binary pump, autosampler, column oven, diode array detecter, and electrospray ionization interface was used. A reversed-phase column (C18 Luna 3 mm particle size, 7.5 cm×4.6 mm ID) with a guard cartridge system was used. The column was maintained at a temperature of 30° C. The mobile phase was acetonitrile/8 mM aqueous ammonium acetate. A 15 minute gradient program was used, starting at 70% acetonitrile over 12 minutes to 95% acetonitrile over 1 minute back to 70% acetonitrile, where it stayed for 2 minutes. The flow rate was 0.6 ml/min. The $t_r$ values reported in the specific examples below were obtained using this procedure.

2-(3-(4-n-Butylpiperidine-1-yl)-propyl)-benzothiazole (5). 1-Benzyl-4-n-butylidenepiperidine (2). A 500 mL 3-necked flask fitted with a stirrer was charged with sodium hydride (1.61 g, 67 mmol) and DMSO (40 mL). The resulting suspension was heated to 90° C. for 30 minutes, until the evolution of hydrogen ceased. The suspension was cooled on an ice-bath for 20 minutes followed by addition of a slurry of butyltriphenylphosphonium bromide (26.6 g, 67 mmol) in DMSO (70 mL). The red mixture was stirred for 15 min at room temperature. 1-Benzyl-4-piperidone 1 (14.0 g, 74 mmol) was slowly added over 30 min, and the mixture was stirred at room temperature over night. $H_2O$ (200 mL) was added to the reaction mixture followed by extraction with heptane (4×100 mL) and ethyl acetate (2×100 mL). The combined organic phases were dried and evaporated to dryness, producing 38.1 g of a yellow oil. The oil was distilled to give 14.9 g (88%) of 2, bp 101–105° C. (0.1 mm Hg). $^1H$ NMR ($CDCl_3$) δ 0.90–0.95 (t, 3H), 1.25–1.41 (m, 2H), 1.90–2.20 (m, 2H), 2.1–2.30 (m, 4H), 2.40–2.45 (m, 4H), 2.50 (s, 2H), 5.17 (t, 1H), 7.20–7.42 (m, 5H).

4-n-Butylpiperidine (3). In a 500 mL flask fitted with a stirrer was added a slurry of 2 (13.2 g, 58 mmol) and 10% palladium on charcoal (1.2 g) in ethanol (70 mL), followed by addition of concentrated hydrochloric acid (1.5 mL). The reaction flask was evacuated and hydrogen was added via a reaction flask. A total of 2.5 $dm^3$ of hydrogen was consumed. The reaction mixture was filtered and evaporated and the residue was dissolved in $H_2O$ (40 mL) and NaOH (20 mL, 2 M) followed by extraction with ethyl acetate (3×100 mL). The combined organic phases were washed with brine (30 mL) and evaporated to dryness to produce 7.1 g of crude 3. The crude product was subjected to column chromatography (eluent:heptane:EtOAc (4:1)) to give pure 3 (2.7 g, 33%). $^1H$ NMR ($CDCl_3$) δ 0.85 (t, 3H), 1.0–1.38 (m, 9H), 1.65 (dd, 2H), 2.38 (s, 1H), 2.55 (dt, 2H), 3.04 (dt, 2H).

4-(4-n-Butylpiperidin-1-yl)butyric acid methyl ester (4). A 50 mL flask was charged with a mixture of 3 (2.7 g, 15 mmol), 4-bromo butyric acid methyl ester (9.9 g, 55 mmol) and potassium carbonate (8.6 g, 62 mmol) in acetonitrile (25 mL). The mixture was stirred at room temperature for 72 hours followed by evaporation to dryness. The crude product was subjected to column chromatography (eluent:$CH_2Cl_2$:$CH_3OH$ (96:4)) to produce pure 4 (3.4 g, 94%). $^1H$ NMR ($CDCl_3$) δ 0.89 (t, 3H), 1.20–1.39 (m, 9H), 1.69 (d, 2H), 1.89 (qv, 2H), 1.98 (t, 2H), 2.36 (t, 2H), 2.43 (t, 2H), 3.99 (d, 2H), 3.67 (s, 3H).

General Procedure for the Preparation of 2-(3-(4-n-butylpiperidine-1-yl)-propyl) heteroaromatics (5, 6, 7, 8, 9, 10, 11, 12, 13).

A small sealed vial equipped with a magnetic stirrer, charged with 4 (121 mg, 0.50 mmol), the appropriate benzdiamines (listed under each compound) (0.55 mmol) and polyphosphoric acid (2.1 g) was heated to 150° C. for 2 hours. The reaction mixture was poured into ice water and neutralized with sodium bicarbonate and filtered. Further treatment of the filtrate with 2 M NaOH produced additional crystals, which were filtered and combined with the earlier crop followed by washing, dried, and recrystallized from ether.

Example 1

2-(3-(4-n-Butylpiperidine-1-yl)-propyl)benzothiazole (5) (34JJ15)

2-Amino-benzenethiol was used as starting material and the general procedure was followed to produce pure 5 (70 mg, 43%). $^1H$ NMR ($CDCl_3$) δ 0.88 (t, 3H), 1.08–1.20 (m, 2H), 1.50 (m, 2H), 1.55–1.70 (m, 7H), 1.72 (qv, 2H), 1.73–1.75 (m, 2H), 2.35–2,39 (m, 2H), 2.41 (t, 2H), 2.61 (t, 2H), 7.39(dt, 2H), 7.89(dd, 2H).

Example 2

2-(3-(4-n-Butylpiperidine-1-yl)-propyl)-benzooxazole (6) (34JJ17)

2-Amino-phenol was used as starting material and the general procedure was followed to produce pure 6 (137 mg, 83%). $^1$H NMR (CDCl$_3$) δ 0.88 (t, 3H), 1.18–1.32 (m, 10H), 1.65 (d, 2H), 1.95 (t, 2H), 2.12 (qv, 2H), 2.49 (t, 2H), 2.92–3.00 (m, 3H), 7.28–7.32 (m, 2H), 7.45–7.50 (m, 1H), 7.64–7.68 (m, 1H).

Example 3

4,5-Difluoro-2-(3-(4-n-butylpiperidine-1-yl)-propyl)-1H-benzoimidazole (7) (34JJ21)

3,4-Difluoro-1,2-diaminobenzene was used as starting material and the general procedure was followed to produce pure 7 (55 mg, 30%). $^1$H NMR (CDCl$_3$) δ 0.93 (t, 3H), 1.30–1.44 (m, 9H), 1.82 (d, 2H), 1.98 (qv, 2H), 2.09 (t, 2H), 2.63 (dt, 2H), 3.07 (d, 2H), 3.14 (dt, 2H), 6.95–7.03 (m, 1H), 7.16–7.21 (m, 1H).

Example 4

6-Fluoro-5-nitro-2-(3-(4-n-butylpiperidine-1-yl)-propyl)-1N-benzoimidazole (8) (34JJ13)

4-Fluoro-5-nitro-1,2-diaminobenzene was used as starting material and the general procedure was followed to produce pure 8 (12 mg, 6%). $^1$H NMR (CDCl$_3$) δ 0.93 (t, 3H), 1.30–1.54 (m, 7H), 1.60 (q, 2H), 1.93 (d, 2H), 2.22 (qv, 2H), 2.42 (t, 2H), 2.82 (t, 2H), 3.24 (t, 2H), 3.31 (d, 2H), 7.34 (d, 1H), 8.29 (d, 1H).

Example 5

5-tert-Butyl-2-(3-(4-n-butylpiperidine-1-yl)-propyl)-1H-benzoimidazole (9) (23JJ83)

4-tert-Butyl-1,2-diaminobenzene was used as starting material and the general procedure was followed to produce pure 9 (74 mg, 38%). $^1$H NMR (CDCl$_3$) δ 0.93 (t, 3H), 1.30–1.42 (m, 18H), 1.81 (d, 2H), 1.96 (qv, 2H), 2.04 (t, 2H), 2.55 (t, 2H), 3.02 (d, 2H), 3.07 (t, 2H), 7.26 (dd, 1H), 7.45 (d, 1H), 7.53 (d, 1H).

Example 6

5-Chloro-6-methyl-2-(3-(4-n-butylpiperidine-1-yl)-propyl)-1H-benzoimidazole (10) (23JJ93)

4-Chloro-5-methyl-1,2-diaminobenzene was used as starting material and the general procedure was followed to produce pure 10 (7 mg, 3%). $^1$H NMR (CDCl$_3$) δ 0.94 (t, 3H), 1.30–1.41 (m, 9H), 1.83 (d, 2H), 1.95 (qv, 2H), 2.08 (t, 2H), 2.46 (s, 3H), 2.57 (t, 2H), 3.04 (d, 2H), 3.09 (t, 2H), 7.32 (s, 1H), 7.50 (s, 1H).

Example 7

4,6-Difluoro-2-(3-(4-n-butylpiperidine-1-yl)-propyl)-1H-benzoimidazole (11) (23JJ77)

3,5-Difluoro-1,2-diaminobenzene was used as starting material and the general procedure was followed to produce pure 11 (50 mg, 27%). $^1$H NMR (CDCl$_3$) δ 0.92 (t, 3H), 1.22–1.43 (m, 7H), 1.56 (q, 2H), 1.87 (d, 2H), 2.13 (qv, 2H), 2.38 (t, 2H), 2.87 (t, 2H), 3.19 (t, 2H), 2.29 (d, 2H), 6.69 (dt, 1H), 7.02 (dd, 1H).

Example 8

2-(3-(4-n-Butylpiperidine)-1-yl-propyl)-1H-imidazo[4,5-c]pyridine (12) (23JJ81)

Pyridine-3,4-diamine was used as starting material and the general procedure was followed to produce pure 12 (18 mg, 11%). $^1$H NMR (CDCl$_3$) δ 0.94 (t, 3H), 1.30–1.42 (m, 9H), 1.87 (d, 2H), 2.01 (qv, 2H), 2.13 (t, 2H), 2.64 (t, 2H), 3.08 (d, 2H), 3.17 (t, 2H), 7.41 (d, 1H), 8.35 (d, 1H), 8.90 (s, 1H).

Example 9

8-(3-(4-n-Butylpiperidine)-1-yl-propyl)-9H-purine (13) (34JJ27)

Pyrimidine-4,5-diamine was used as starting material and the general procedure was followed to produce pure 12 (94 mg, 57%). $^1$H NMR (MeOD) δ 0.92 (t, 3H), 1.29–1.39 (m, 6H), 1.43–1.60 (m, 3H), 2.00 (d, 2H), 2.43 (qv, 2H), 3.00 (t, 2H), 3.21–3.35 (m, 4H), 3.64 (d, 2H), 9.25 (s, 1H), 9.38 (s, 1H).

Example 10

7-(3-(4-n-Butylpiperidine)-1-yl-propyl)-3,8-dihydro-imidazo[4',5':3,4]benzo[1,2-d][1,2,3]triazole (14) (34JJ39)

1H-Benzotriazole-4,5-diamine was used as starting material and the general procedure was followed to produce pure 14 (24 mg, 13%). $^1$H NMR (DMSO) δ 0.83 (t, 3H), 1.00–1.28 (m, 9H), 1.57 (d, 2H), 1.80 (t, 2H), 1.94 (qv, 2H), 2.32 (t, 2H), 2.82 (d, 2H), 2.88 (t, 2H), 7.49 (d, 1H), 7.62 (d, 1H).

Example 11

2-(3-(4-n-Butylpiperidine)-1-yl-propyl)-3a,4,5,6,7,7a-hexahydro-1H-benzoimidazole (15)

Cyclohexane-1,2-diamine was used as starting material and the general procedure was followed to produce pure 15 (79 mg, 47%). 1H NMR (CDCl3) δ 0.80–1.05 (m, 11H), 1.27–1.75 (m, 17H), 2.57 (t, 2H), 2.66 (t, 2H), 3.57 (q, 1H), 4.48 (q, 1H).

General Procedure for the Preparation of Substituted Indole Derivatives (16, 17, 18, 19, 20 and 21). 1,3-Dibromopropane (205 μl, 2.0 mmol) in 5 mL DMF was placed in a 50 mL flask. The appropriate indole (2.0 mmol) and KOH (280 mg, 5.0 mmol) was partly dissolved in 5 mL DMF and added during stirring. Resulting suspension was stirred overnight at room temperature. 4-Butylpiperidine (3) (178 mg, 1.0 mmol) in 5 mL DMF was added and the mixture was stirred overnight at room temperature. Ethyl acetate (20 mL) and water (20 mL) were added. The phases were separated and the aqueous phase was re-extracted with ethyl acetate (20 mL). The combined organic phases were washed with brine, dried over magnesium sulphate and evaporated to dryness to produce crude product. Crude product was purified by column chromatography (0–5% methanol:dichloromethane) to produce pure products.

Example 12

1-(3-(4-n-Butylpiperidine)-1-yl-propyl)-1H-indole (16) (35AKU-15)

1H-Indole was used as starting material and the general procedure was followed to produce pure 16 (69 mg, 23%).

¹H NMR (CDCl₃) δ 0.9 (t, 3H), 1.2–1.3 (m, 7H), 1.5 (q, 2H), 1.75 (d, 2H), 2.1–2.3 (m, 4H), 2.5 (t, 2H), 3.1 (d, 2H), 4.25 (t, 2H), 6.5 (d, 1H), 7.1 (m, 2H), 7.2 (t, 1H), 7.35 (d, 1H), 7.6 (d, 1H).

Example 13

1-(3-(4-n-Butylpiperidine)-1-yl-propyl)-1H-benzoimidazole (17) (35AKU-16)

1H-Benzoimidazole was used as starting material and the general procedure was followed to produce pure 17 (69 mg, 23%). ¹H NMR (CDCl₃) δ 0.9 (t, 3H), 1.2–1.3 (m, 7H), 1.5 (q, 2H), 1.75 (d, 2H), 2.25 (m, 4H), 2.6 (t, 2H), 3.1 (d, 2H), 4.3 (t, 2H), 7.2–7.3 (m, 2H), 7.45 (d, 1H), 7.75 (d, 1H), 8.0 (s, 1H).

Example 14

3-Methyl-1-(3-(4-n-butylpiperidine)-1-yl-propyl)-1H-indole (18) (35AKU-22)

3-Methyl-1H-indole was used as starting material and the general procedure was followed to produce pure 18. ¹H NMR (CDCl₃) δ 0.9 (t, 3H), 1.2–1.3 (m, 9H), 1.65 (d, 2H), 1.9 (t, 2H), 2.0 (m, 2H), 2.25 (m, 2H), 2.3 (s, 3H), 2.85 (d, 2H), 4.1 (t, 2H), 6.85 (s, 1H), 7.1 (t, 1H), 7.2 (t, 1H), 7.55 (d, 1H).

Example 15

5-Bromo-1-(3-(4-n-butylpiperidine)-1-yl-propyl)-1H-indole (19) (35AKU-23)

5-Bromo-1H-indole was used as starting material and the general procedure was followed to produce pure 19. ¹H NMR (CDCl₃) δ 0.9 (t, 3H), 1.2–1.3 (m, 9H), 1.65 (d, 2H), 1.85 (t, 2H), 2.0 (t, 2H), 2.2 (t, 2H), 2.8 (d, 2H), 4.15 (t, 2H), 6.4 (d, 1H), 7.1 (d, 1H), 7.25 (m, 2H), 7.75 (s, 1H).

Example 16

3-Formyl-1-(3-(4-n-butylpiperidine)-1-yl-propyl)-1H-indole (20) (35AKU-24)

3-Formyl-1H-Indole was used as starting material and the general procedure was followed to produce pure 20. ¹H NMR (CDCl₃) δ 0.9 (t, 3H), 1.2–1.3 (m, 9H), 1.7 (d, 2H), 1.95 (t, 2H), 2.1 (m, 2H), 2.3 (t, 2H), 2.9 (d, 2H), 4.3 (t, 2H), 7.3–7.5 (m, 3H), 8.3 (m, 1H), 10.0 (s, 1H).

Example 17

7-Bromo-1-(3-(4-n-butylpiperidine)-1-yl-propyl)-1H-indole (21) 35AKU-25)

7-Bromo-1H-indole was used as starting material and the general procedure was followed to produce pure 21. ¹H NMR (CDCl₃) δ 0.9 (t, 3H), 1.2–1.3 (m, 9H), 1.65 (d, 2H), 1.9 (t, 2H), 2.05 (m, 2H), 2.3 (t, 2H), 2.9 (d, 2H), 4.55 (t, 2H), 6.45 (d, 1H), 6.9 (t, 1H), 7.1 (d, 1H), 7.35 (d, 1H), 7.55 (d, 1H).

Example 18

1-(3-Bromo-propyl)-1H-indazole (22)

1,3-Dibromopropane (508 µl, 5.0 mmol)) was dissolved in 10 mL DMF and placed in a 100 mL flask. Indazole (592 mg, 5.0 mmol) and KOH (282 mg, 5.0 mmol) were added and the suspension was stirred overnight at room temperature. Ethyl acetate (50 mL) and water (50 mL) were added. Phases were separated and the aqueous phase was re-extracted with ethyl acetate (50 mL). The combined organic phases were washed with brine, dried over magnesium sulphate and evaporated to dryness to produce 751 mg of a yellow oil. Crude product was further purified by column chromatography (0–10% methanol:dichloromethane) to produce pure 22 (169 mg, 14%).

Example 19

1-(3-(4-n-Butylpiperidine)-1-yl-propyl)-1H-indazole (23) (35AKU-21)

To a 50 mL flask was added 22 (169 mg, 0.7 mmol) and 10 mL DMF. 4-Butylpiperidine (3) (142 mg, 1.0 mmol) and KOH (113 mg, 2.0 mmol) were partly dissolved in DMF (5 mL) and added. The suspension was stirred overnight at room temperature. Ethyl acetate (20 mL) and water (20 mL) were added. The phases were separated and the aqueous phase was re-extracted with ethyl acetate (20 mL). The combined organic phases were washed with brine, dried over magnesium sulphate and evaporated to dryness to give 192 mg of light brown oil. Crude product was purified by column chromatography (0–10% methanol:dichloromethane) to produce pure product 23 (61 mg, 29%). Oxalate-salt was prepared from oxalic acid (1.1 eq.) in methanol/diethylether. ¹H NMR (CDCl₃) δ 0.9 (t, 3H), 1.2–1.3 (m, 9H), 1.65 (d, 2H) 1.9 (t, 2H), 2.15 (m, 2H), 2.3 (t, 2H), 2.85 (d, 2H), 4.45 (t, 2H), 7.1 (t, 1H), 7.35 (t, 1H), 7.5 (d, 1H), 7.7 (d, 1H), 8.0 (s, 1H).

Example 20

1-(2-Hydroxy-phenyl)-ethanone oxime (24)

Hydroxylammoniumchloride (6.96 g, 100 mmol) and sodium acetate. 3H₂O (13.6 g, 100 mmol) were dissolved in 150 mL ethanol:water (7:3) and added to a solution of 2-hydroxyacetophenone (6.81 g, 50 mmol) in 50 mL ethanol:water (7:3). The pH was adjusted to 4–5 with 4N HCl (~10 mL) and the reaction mixture was then heated to reflux (100° C.) for 1 hour. The oil bath was removed and the mixture was left overnight with stirring. Ethanol was partly removed by evaporation and the aqueous phase was extracted with ethyl acetate two times. The combined organic phases were dried over magnesium sulphate and evaporated to dryness to produce 7.55 g of pure 24.

Example 21

3-Methyl-benzo[d]isoxazole (25)

Acetic anhydride (7.1 mL, 75 mmol) was added to 24 (7.55 g, 50 mmol) in a 100 mL flask. The mixture was heated to 60° C. for 3 hours followed by evaporation to dryness. Potassium carbonate (8.7 g, 63 mmol) was partly dissolved in 40 mL DMF and added to the mixture. The mixture was stirred at room temperature overnight and finally heated to 100° C. for 30 minutes. Ethyl acetate and water were added. The phases were separated and the aqueous phase was extracted with ethyl acetate and dichloromethane. The combined organic phases were dried over magnesium sulphate and evaporated to dryness to give 5.6 g of a yellow oil. Crude product was purified by column chromatography (100% dichloromethane), producing pure 25 (4.6 g). ¹H NMR (CDCl₃) δ 2.6 (s, 3H), 7.3 (m, 1H), 7.55 (m, 2H), 7.65 (m, 1H).

Example 22

3-But-3-enyl-benzo[d]isoxazole (26)

3.0 mL dry THF was added to an oven-dried 25 mL flask and cooled to −78° C. on a dry ice/isopropanol bath. Diisopropylamine (840 µl, 6.0 mmol) was added followed by n-BuLi (3.8 mL, 1.6 M, 6.0 mmol). The LDA-solution that was obtained was left at room temperature. Compound 25 (666 mg, 5.0 mmol) was dissolved in 10 mL dry THF and added to an oven-dried 50 mL flask followed by allylbromide (476 µl, 5.5 mmol). The freshly prepared LDA-solution was slowly added at −78° C. and the mixture was left at room temperature for 30 min. Ethyl acetate and water were added. The phases were separated and the aqueous phase was extracted with ethyl acetate. The combined organic phases were dried over magnesium sulphate and evaporated to dryness to produce 893 mg of a light brown oil. Crude product was purified by column chromatography (heptane:ethyl acetate; 9:1; isocratic) to produce pure 26 (355 mg, 41%).

Example 23

3-(Benzo[d]isoxazol-3-yl)-propionaldehyde (27)

Compound 26 (549 mg, 3.2 mmol), water (5 mL), 1,4-dioxane (15 mL) and osmium tetroxide (15 mg, 0.06 mmol) were stirred for 5 min. in a small flask. Sodium metaperiodate (1.56 g, 7.3 mmol) was added over 30 min. and the suspension was then stirred for 1 hour. Ethyl acetate and water were added. The phases were separated and the aqueous phase was extracted with ethyl acetate and dichloromethane. The combined organic phases were dried over magnesium sulphate and evaporated to dryness to produce 784 mg of crude 27, which was used directly without further purification in the synthesis compound 28.

Example 24

3-(3-(4-n-Butylpiperidine)-1-yl-propyl)-benzo[d]isoxazole (28) (35AKU-2)

Compound 27 (~500 mg, 2–3 mmol) was dissolved in 5 mL methanol. 4-Butylpiperidine. HCl 3 (260 mg, 1.5 mmol) was dissolved in 10 mL methanol and added. Sodium cyanoborohydride (188 mg, 3.0 mmol) in 10 mL methanol was added, giving a dark brown solution which was stirred overnight. Water was added and methanol was partly removed by evaporation. The aqueous phase was extracted with ethyl acetate and dichloromethane. The combined organic phases were dried over magnesium sulphate and evaporated to dryness. The crude product was further purified by preparative HPLC (mobile phase 0–80% acetonitrile in water (0.1% TFA)) giving 28 (244 mg, 54%). HCl-salt was prepared from 2M HCl in diethylether. The crystals were filtered and washed by diethylether. $^1$H-NMR (CDCl$_3$) δ 0.9 (t, 3H), 1.2–1.3 (m, 9H), 1.65 (d, 2H), 1.9 (t, 2H), 2.05 (m, 2H), 2.45 (t, 2H), 2.9 (d, 2H), 3.0 (t, 2H), 7.3 (m, 1H), 7.55 (m, 2H), 7.7 (d, 1H).

Example 25

3-(1H-Indol-3-yl)-propan-1-ol (29)

A suspension of lithium aluminum hydride (4.68 g, 126 mmol) in 230 mL anhydrous diethylether was stirred heavily. 3-Indole propionic acid (10.0 g, 53 mmol) dissolved in 460 mL anhydrous diethylether was transferred to a dropping funnel and added at such a rate that gentle reflux was maintained. The reaction mixture was left with stirring at reflux temperature for 2 h, then at room temperature overnight. Then reflux was continued for 2 h before cooling to room temperature. 25 mL H$_2$O was slowly added followed by 70 mL H$_2$O/H$_2$SO$_4$ (1:3 H$_2$O/H$_2$SO$_4$). The resulting clear mixture was extracted with 110 mL diethylether three times. The combined organic phases were washed with brine, dried with Na$_2$SO$_4$, filtrated and concentrated to bright oil, which was used without further purification.

Example 26

Methanesulfonic acid 3-(1H-indole-3-yl)-propyl ester (30)

Compound 29 (1.8 g, 5.44 mmol) was transferred to a flame-dried flask filled with argon and dissolved in anhydrous THF then cooled to −40° C. Triethylamine (0.72 g, 7.07 mmol) was added by syringe followed by MeSO$_2$Cl (0.75 g, 6.53 mmol). The temperature of the reaction mixture was allowed to rise to room temperature (10–15 minutes) before it was quickly filtrated and concentrated. The crude oil was dissolved in CH$_2$Cl$_2$ and washed with H$_2$O. The organic phase was dried with MgSO$_4$, filtrated and concentrated in vacuo to a dark, brown oil. The crude product was used immediately in the next step.

Example 27

3-(3-(4-n-Butylpiperidine)-1-yl-propyl)-1H-indole (31) (39MF34)

Na$_2$CO$_3$ (1.28 g, 11.97 mmol) was added to a solution of 4-butylpiperidine hydrochloride 3 (967 mg, 5.44 mmol) in anhydrous DME. The resulting suspension was stirred for 30 min. Compound 30 was dissolved in anhydrous DME and added to the suspension. The resulting mixture was stirred under argon at 82° C. over night. The mixture was cooled, EtOAc and H$_2$O was added, the two phases were separated, and the water was extracted with EtOAc three times. The combined organic phases were washed with brine, dried with Na$_2$SO$_4$, filtrated and concentrated in vacuo. The crude oil was dissolved in anhydrous CH$_2$Cl$_2$ and HCl in dioxane (4M, 2 mL) was added. The product (31) was isolated as white crystals by recrystallization from MeOH/diethylether. $^1$H-NMR (CDCl$_3$) δ 0.93 (t, 3H), 1.32–1.58 (m, 7H), 1.60 (q, 2H), 1.93 (d, 2H), 2.22 (qv, 2H), 2.42 (t, 2H), 2.82 (t, 2H), 3.24 (t, 2H), 3.31 (d, 2H), 6.91–7.10 (m, 2H), 7.34 (d, 1H), 7.53 (d, 1H).

Example 28

4-Nitro-2-(3-(4-n-butylpiperidine)-1-yl-propyl)-1H-benzoimidazole (32) (29MF03)

A 25 mL flask fitted with a condenser and a magnetic stirrer was charged with 1,2-diamino-3-nitrobenzene (0.251 g, 1.64 mmol) and 4-(4-n-butylpiperidin-1-yl)-butyric acid methyl ester (4) (0.395 g, 1.64 mmol) in 5 mL 4 M HCl. The reaction was refluxed for 24 h followed by addition of 2.0 M NaOH to produce basic conditions, stirred at room temperature for 1 h and extracted with ethyl acetate (5×50 mL). The combined organic phases were washed with 15 mL brine, then dried over MgSO4 and evaporated to dryness to produce 0.45 g of crude product. The crude material was subjected to column chromatography (eluent:$CH_2Cl_2$:MeOH (20:1)) to give the pure title compound (32) (0.03 g, 5%). $^1$H NMR (CDCl$_3$) 0.92 (t, 3H), 1.25–1.42 (m, 9H), 1.55–1.64 (m, 2H), 1.75–1.82 (m, 2H), 2.10–2.23 (m, 2H), 2.24–2.31 (m, 2H), 2.67–2.77 (m, 2H), 3.17–3.22 (m, 4H), 7.25–7.35 (m, 1H), 7.97–8.04 (m, 1H), 8.08–8.13 (m, 1H).

Example 29

5-Nitro-2-(3-(4-n-butylpiperidine)-1-yl-propyl)-1H-benzoimidazole (33) (29MF04)

A 25 mL flask fitted with a condenser and a magnetic stirrer was charged with 1,2-diamino-4-nitrobenzen (0.259 g, 1.69 mmol) and 4-(4-n-butylpiperidin-1-yl)-butyric acid methyl ester (4) (0.408 g, 1.69 mmol) in 5 mL 4 M HCl. The reaction was refluxed for 24 h followed by addition of 2.0 M NaOH to produce basic conditions, then stirred in room temperature for 1 h and extracted with ethyl acetate (5×50 mL). The combined organic phases were washed with 15 mL brine then dried over MgSO4 and evaporated to dryness to produce 0.27 g of a crude material. The crude material was subjected to column chromatography (eluent: $CH_2Cl_2$:MeOH (20:1)) to produce the final compound (122 mg). This material was isolated and dissolved in a 2.0 M HCl in ether solution followed by evaporation to dryness to give the pure title compound (33) (80 mg, 10%). $^1$H NMR (CD$_3$OD) 0.92(t, 3H), 1.34 (m, 6H), 1.55 (m, 3H), 2.00 (d, 2H), 2.45 (m, 2H), 3.01 (t, 2H), 3.29–3.37 (dt, 4H), 3.64 (d, 2H), 7.94 (d, 1H), 8.43 (dd, 1H), 8.65 (d, 1H).

Example 30

4-Hydroxy-2-(3-(4-n-butylpiperidine)-1-yl-propyl)-1H-benzoimidazole (34) (29MF07)

A 25 mL flask fitted with a condenser and magnetic stirrer was charged with 1,2-diamino-4-hydroxybenzene (0.177 g, 1.43 mmol) and 4-(4-n-butylpiperidin-1-yl)-butyric acid methyl ester (4) (0.345 g, 1.43 mmol) in 5 mL 4 M HCl. The reaction was refluxed for 20 h followed by addition of 2.0 M NaOH to to produce basic conditions. The mixture was evaporated to dryness on 10 mL silica and subjected to column chromatography (eluent: $CH_2Cl_2$:MeOH (20:1)) to produce crude product (0.145 g). The crude was subjected to preparative HPLC (eluent: buffer A: 0.1% TFA; buffer B: 80% $CH_3CN$+0.1% TFA) and product isolated was evaporated with 1.0 M TFA in ether to give the pure title compound 34 (74 mg, 16%) as a trifluoroacetic acid salt. $^1$H NMR(CD$_3$OD) 0.98(t, 3H), 1.32–1.45 (m, 6H), 1.51–1.69 (m, 3H), 1.97–2.08 (d, 2H), 2.37–2.47 (m, 2H), 2.95–3.12 (m, 2H), 3.26–3.41 (m, 4H), 3.58–3.3.72 (m, 2H), 6.91–6.97 (d, 1H), 7.19–7.25 (d, 1H), 7.35–7.43 (t, 1H).

Example 31

2-(3-(4-n-Butylpiperidine)-1-yl-propyl)-1H-benzoimidazole (35) (21MF25)

A 25 mL flask fitted with a condenser and a magnetic stirrer was charged with 1,2-diaminobenzene (0.201 g, 18.6 mmol) and 4-(4-n-butylpiperidin-1-yl)-butyric acid methyl ester (4) (0.50 g, 2.1 mmol) in 6 mL 4 M HCl. The reaction was refluxed for 20 hours followed by addition of 2.0 M NaOH to to produce basic conditions. The precipitate was filtrated and dried under vacuum followed by column chromatography (eluent: $CH_2Cl_2$:MeOH (10:1)) to produce the pure title compound 35 (0.40 g, 73%). mp 78–79° C., $^1$H NMR(CDCl$_3$) 0.92 (t, 3H), 1.33 (m, 6H), 1.50 (m, 3H), 1.80–1.95 (m, 2H), 2.0–2.15 (m, 2H), 2.16–2.24 (m, 2H), 2.62–2.75 (m, 2H), 3.17–3.21 (m, 4H), 7.20–7.23 (m, 2H), 7.52–7.59 (m, 2H).

Example 32

4-Methyl-2-(3-(4-n-butylpiperidine)-1-yl-propyl)-1H-benzoimidazole (36) (29MF08)

A 25 mL flask fitted with a condenser and a magnetic stirrer was charged with 1,2-diamino-3-methylbenzene (0.168 g, 1.37 mmol) and 4-(4-n-butylpiperidin-1-yl)-butyric acid methyl ester (4) (0.331 g, 1.37 mmol) in 5 mL 4 M HCl. The reaction was refluxed for 48 h followed by addition of 4.0 M NaOH. The reaction mixture was extracted with dichloromethane (4×25 mL). The combined organic phases were dried over MgSO4 and evaporated to give 0.40 g of crude product. The crude material was subjected to column chromatography (eluent: $CH_2Cl_2$:MeOH (20:1)) and the isolated product was evaporated to dryness with 1.0 M HCl in ether to give the pure title compound 36 (0.210 g, 44%). $^1$H NMR(CD$_3$OD) 0.92 (t, 3H), 1.33 (m, 6H), 1.54 (m, 3H), 1.99 (d, 2H), 2.43 (m, 2H), 2.65 (m, 2H), 3.00 (m, 2H), 3.28 (m, 2H), 3.63 (m, 2H), 7.38 (d, 1H), 7.47 (t, 1H), 7.59 (d, 1H).

Example 33

3-(2-(4-n-butylpiperidine)-1-yl-ethyl)-1H-indole (37)

A 25 mL flask fitted with a magnetic stirrer was charged 4-n-butylpiperidine hydrochloride 3 (0.256 g, 1.4 mmol) and potassium carbonate (0.5 g, 3.6 mmol) in dioxane (5 mL). The mixture was stirred at room temperature for 2 h followed by addition of 3-(2-bromoethyl)indole (0.30 g, 1.3 mmol) dissolved in dioxane (5 mL). The mixture was then stirred at 50° C. for 24 h. Addition of water (15 mL) was followed by extraction with ethyl acetate (3×50 mL). The combined organic phases were dried over MgSO4 and evaporated to give 1.02 g of crude product. The crude product was subjected to column chromatography (Eluent: $CH_2Cl_2$:MeOH (20:1)) to give pure title compound 37 (0.08 g, 21%). $^1$H NMR(CDCl$_3$) 0.90(t, 3H), 1.25–1.49 (m, 9H), 1.72–1.79 (m, 2H), 2.77 (t, 2H), 3.06 (t, 2H), 3.16 (d, 2H), 7.03 (s, 1H), 7.11 (t, 1H), 7.19 (t, 1H), 7.36 (d, 1H), 7.61 (d, 1H), 8.09–8.16 (s, 1H).

Example 34

(2-(4-Chloro-butan-1-one)-phenyl)-carbamic acid tert-butyl ester (38)

To a dry 100 mL one-necked flask fitted with condenser, a magnetic stirrer and argon inlet was added 4-chlorobutanoyl chloride (624 mg, 44 mmol) and bis(acetonitrile)dichloropalladium (34 mg) in 10 mL dry toluene. To the mixture was added (2-trimethylstannyl-phenyl)-carbamic acid tert-butyl ester (1.5 g, 42 mmol) (*Bioorg. Med. Chem.*, 6:811 (1998)) dissolved in 15 mL dry toluene. The mixture was then refluxed for 1 h and then stirred in room temperature for 17 h. The reaction was evaporated to dryness which produced a crude product (1.6 g) and this was subjected to column chromatography (eluent:heptane:EtOAc 10:1) to give the pure title compound 38 (1.15 g, 92%). $^1$H NMR (CDCl$_3$) 1.52 (t, 9H), 2.22 (m, 2H), 3.22 (t, 2H), 3.68 (t, 2H), 7.03 (t, 1H), 7.51 (t, 1H), 7.91 (d, 1H), 8.48 (d, 1H), 10.90 (s, 1H).

Example 35

(2-(3-(4-n-butylpiperidine)-1-yl-propyl)-phenyl)-carbamic acid tert-butyl ester (39)

To a dry 5 mL flask fitted with a magnetic stirrer and argon inlet was added 38 (0.5 g, 1.7 mmol) and 4-n-butulpiperidine 3 (1.5 g, 10.6 mmol) and left stirring at 60° C. for 70 h. The crude reaction mixture was subjected to column chromatography (eluent CH$_2$Cl$_2$:MeOH 20:1) to produce the pure compound 39 (0.49 g, 72%). $^1$H NMR(CDCl$_3$) 0.87 (t, 3H), 1.18–1.27 (m, 9H), 1.52 (s, 9H), 1.64 (m, 2H), 1.94 (m, 4H), 2.41 (t, 2H), 2.91 (d, 2H), 3.03 (t, 2H), 7.00 (t, 1H), 7.49 (t, 1H), 7.91 (d, 1H), 8.46 (d, 1H), 10.97 (s, 1H).

Example 36

3-(3-(4-n-Butylpiperidine)-1-yl-propyl)-1H-indazole (40) (39MF34)

Compound 39 (0.06 g, 0.15 mmol) dissolved 2 mL 4.0 M HCl in dioxane was added to a 5 mL flask and stirred at room temperature for 1 h. The mixture was evaporated to dryness and then redissolved in 1 mL concentrated HCl and the temperature was adjusted to 0° C. with an ice/water bath. To the cooled mixture was added sodium nitrite (0.010 g, 0.15 mmol) dissolved in 2 mL water, and the reaction mixture was maintained at 0° C. for 1.5 h. followed by addition of tin dichloride (0.08 g, 0.36 mmol) dissolved in 2 mL concentrated HCl. After 1.5 h at 0° C., crystals were formed. The crystals were filtered and washed with water to produce the crude product (0.07 g). The crude product was subjected to column chromatography (eluent:CH$_2$Cl$_2$:MeOH 20:1) to give the pure compound 40 (9.0 mg, 20%) $^1$H NMR (CDCl$_3$) 0.88 (t, 3H), 1.19–1.33 (m, 9H), 1.67 (d, 2H), 1.95 (t, 2H), 2.08 (m, 2H), 2.50 (t, 2H), 2.93–3.20 (m, 4H), 7.12 (t, 1H), 7.36 (t, 1H), 7.43 (d, 1H), 7.71 (d, 1H), 9.87–10.05 (s, 1H).

Example 37

3-(2-Chloro-ethoxy)-7-methyl-benzo[d]isoxazole (41)

1-Bromo-2-chloroethane (168 µl, 2.0 mmol) was added to 5 ml DMF in a 50 ml flask. 7-Methyl-benzo[d]isoxazol-3-ol (298 mg, 2.0 mmol), potassium carbonate (276 mg, 2.0 mmol) and additional DMF (5 ml) were added and the mixture was stirred for 12 h. Ethylacetate (50 ml) and H$_2$O (50 ml) were added. The two phases were separated and the aqueous phase was extracted with ethylacetate. The combined organic phases were washed with brine, dried over MgSO4 and evaporated to dryness to give 420 mg of the crude product. The crude product was subjected to column chromatography (0–5% methanol in dichloromethane) to give the pure title compound 41 (290 mg, 70%). $^1$H NMR (CDCl$_3$) 2.5 (s, 3H), 3.9 (t, 2H), 4.7 (t, 2H), 7.2 (t, 1H), 7.3 (d, 1H), 7.5 (d, 2H).

Example 38

3-(2-(4-n-Butylpiperidine)-ethoxy)-7-methyl-benzo[d]isoxazole (42) (35AKU-41)

Compound 41 (294 mg, 1.4 mmol) was dissolved in DMF (5 ml) in a 50 ml flask followed by addition of a mixture of 4-n-butyl-piperidine (284 mg; 1.6 mmol) and potassium carbonate (442 mg; 3.2 mmol) dissolved in DMF (15 ml). The mixture was stirred for 2 days at 80° C. Ethylacetate (50 ml) and H$_2$O (50 ml) were added, the phases were separated, and the aqueous phase was extracted with ethylacetate (3×50 ml). The combined organic phases were washed with brine, dried over MgSO4 and evaporated to dryness to produce the crude product (454 mg). The crude product was subjected to column chromatography (0–5% methanol in dichloromethane) to produce the pure title compound 42 (131 mg, 30%). The oxalate salt was prepared from oxalic acid (1.1 eq.) in methanol/diethylether. $^1$H NMR (CDCl$_3$) 0.9 (t, 3H), 1.2–1.3 (m, 9H), 1.7 (d, 2H), 2.1 (t, 2H), 2.5 (s, 3H), 2.9 (t, 2H), 3.0 (d, 2H), 4.6 (t, 2H), 7.15 (t, 1H), 7.3 (d, 1H), 7.45 (d, 1H).

Example 39

1-(3-(4-Methylpiperidine)-1-yl-propyl)-1H-indazole (43) (46RO13.48)

Solid K$_2$CO$_3$ (70 mg, 0.5 mmol) was added to a mixture of 7-bromo-1-(3-(4-n-butylpiperidine)-1-yl-propyl)-1H-indole (96 mg, 0.4 mmol) and 4-methylpiperidine (30 mg, 0.3 mmol) in CH$_3$CN (2 ml). The resulting slurry was stirred at 50° C. for 48 h and then cooled to ambient temperature. The slurry was then poured into water (10 ml) and worked up as follows: extraction with ethyl acetate (3×10 ml), washing of the collected organic phases sequentially with water (3×5 mL) and brine, followed by drying over MgSO4 and removal of the solvent by rotary evaporation. The residue was purified on ISOLUTE SCX to give compound 43 (25 mg, 24%). Oxalate-salt was prepared from oxalic acid (1.1 eq.) in methanol/diethylether. $^1$H NMR (CD$_3$OD) δ 0.9 (t, 3H), 1.2 (m, 2H), 1.6 (m, 1H), 1.8 (d, 2H), 2.15 (m, 2H), 2.8 (m, 2H), 3.0 (m, 2H), 3.4 (m, 2H), 4.45 (t, 2H), 7.1 (t, 1H), 7.35 (t, 1H), 7.5 (d, 1H), 7.7 (d, 1H), 8.0 (s, 1H).

Example 40

1-(3-(4-Pentylpiperidine)-1-yl-propyl)-1H-indazole (44) (46RO13.57)

Solid K$_2$CO$_3$ (35 mg, 0.25 mmol) was added to a mixture of 7-bromo-1-(3-(4-n-butylpiperidine)-1-yl-propyl)-1H-indole 48 mg, 0.4 mmol) and 4-pentylpiperidine (23 mg, 0.15 mmol) in CH$_3$CN (2 ml). The resulting slurry was stirred at 50° C. for 48 h and then cooled to ambient temperature. The slurry was then poured into water (10 ml) and worked up as follows: extraction with ethyl acetate (3×10 ml), washing of the collected organic phases sequentially with water (3×5 ml) and brine, followed by drying over MgSO4 and removal of the solvent by rotary evaporation. The residue was purified on ISOLUTE SCX to give compound 44 (25 mg, 40%). Oxalate-salt was prepared from oxalic acid (1.1 eq.) in methanol/diethylether. $^1$H NMR (CD$_3$OD) δ 0.9 (t, 3H), 1.2 (m, 12H), 1.6 (m, 1H), 1.8 (d, 2H), 2.15 (m, 2H), 2.8 (m, 2H), 3.0 (m, 2H), 3.4 (m, 2H), 4.45 (t, 2H), 7.1 (t, 1H), 7.35 (t, 1H), 7.5 (d, 1H), 7.7 (d, 1H), 8.0 (s, 1H).

Example 41

1-(3-(4-Propylpiperidine)-1-yl-propyl)-1H-indazole (45) (46RO13.55LH)

Solid K$_2$CO$_3$ (35 mg, 0.25 mmol) was added to a mixture of 7-bromo-1-(3-(4-n-butylpiperidine)-1-yl-propyl)-1H-indole (48 mg, 0.2 mmol) and 4-propylpiperidine (19 mg, 0.15 mmol) in CH$_3$CN (2 ml). The resulting slurry was stirred at 50° C. for 48 h and then cooled to ambient temperature. The slurry was then poured into water (10 ml) and worked up as follows: extraction with ethyl acetate (3×10 ml), washing of the collected organic phases sequentially with water (3×5 ml) and brine, followed by drying over MgSO4 and removal of the solvent by rotary evaporation. The residue was purified on ISOLUTE SCX to give title compound 45 (16 mg, 28%). Oxalate-salt was prepared from oxalic acid (1.1 eq.) in methanol/diethylether. $^1$H NMR (CD$_3$OD) δ 0.9 (t, 3H), 1.2 (m, 6H), 1.6 (m, 1H), 1.8 (d, 2H), 2.15 (m, 2H), 2.8 (m, 2H), 3.0 (m, 2H), 3.4 (m, 2H), 4.45 (t, 2H), 7.1 (t, 1H), 7.35 (t, 1H), 7.5 (d, 1H), 7.7 (d, 1H), 8.0 (s, 1H).

Example 42

1-(3-(4-(3-Methyl-butyl)-piperidine)-1-yl-propyl)-1H-indazole (46) (46RO13.58)

Solid K$_2$CO$_3$ (35 mg, 0.25 mmol) was added to a mixture of 7-bromo-1-(3-(4-n-butylpiperidine)-1-yl-propyl)-1H-indole (48 mg, 0.2 mmol) and 4-(3-methyl-butyl)-piperidine (23 mg, 0.15 mmol) in CH$_3$CN (2 ml). The resulting slurry was stirred at 50° C. for 48 h and then cooled to ambient temperature. The slurry was then poured into water (10 ml) and worked up as follows: extraction with ethyl acetate (3×10 ml), washing of the collected organic phases sequentially with water (3×5 ml) and brine, followed by drying over MgSO4 and removal of the solvent by rotary evaporation. The residue was purified on ISOLUTE SCX to give title compound 46 (18 mg, 30%). Oxalate-salt was prepared from oxalic acid (1.1 eq.) in methanol/diethylether. $^1$H NMR (CD$_3$OD) δ 0.9 (t, 6H), 1.2–1.5 (m, 8H), 1.8 (d, 2H), 2.15 (m, 2H), 2.8 (m, 2H), 3.0 (m, 2H), 3.4 (m, 2H), 4.45 (t, 2H), 7.1 (t, 1H), 7.35 (t, 1H), 7.5 (d, 1H), 7.7 (d, 1H), 8.0 (s, 1H).

Example 43

1-(3-(4-Pentylidene-piperidine)-1-yl-propyl)-1H-indazole (47) (46RO13.46)

Solid K$_2$CO$_3$ (35 mg, 0.25 mmol) was added to a mixture of 7-bromo-1-(3-(4-n-butylpiperidine)-1-yl-propyl)-1H-indole (48 mg, 0.2 mmol) and 4-Pentylidene-piperidine (23 mg, 0.15 mmol) in CH$_3$CN (2 ml). The resulting slurry was stirred at 50° C. for 48 h and then cooled to ambient temperature. The slurry was poured into water (10 ml) and worked up as follows: extraction with ethyl acetate (3×10 ml), washing of the collected organic phases sequentially with water (3×5 ml) and brine, followed by drying over MgSO4 and removal of the solvent by rotary evaporation. The residue was purified on ISOLUTE SCX to give the title compound 47 (3 mg, 5%). Oxalate-salt was prepared from oxalic acid (1.1 eq.) in methanol/diethylether. $^1$H NMR (CD$_3$OD) δ 0.9 (t, 3H), 1.3 (m, 4H), 2.0 (m, 2H), 2.3 (m, 3H), 2.35 (d, 2H), 2.7 (m, 2H), 3.1 (m, 3H), 3.4 (m, 2H), 4.45 (t, 2H), 5.3 (m, 1H) 7.1 (t, 1H), 7.35 (t, 1H), 7.5 (d, 1H), 7.7 (d, 1H), 8.0 (s, 1H).

Example 44

1-(3-(4-Propylidene-piperidine)-1-yl-propyl)-1H-indazole (48) (46RO13.45)

Solid K$_2$CO$_3$ (35 mg, 0.25 mmol) was added to a mixture of 7-bromo-1-(3-(4-n-butylpiperidine)-1-yl-propyl)-1H-indole (48 mg, 0.2 mmol) and 4-Propylidene-piperidine (18 mg, 0.15 mmol) in CH$_3$CN (2 ml). The resulting slurry was stirred at 50° C. for 48 h and then cooled to ambient temperature. The slurry was poured into water (10 ml) and worked up as follows: extraction with ethyl acetate (3×10 ml), washing of the collected organic phases sequentially with water (3×5 ml) and brine, followed by drying over MgSO4 and removal of the solvent by rotary evaporation. The residue was purified on ISOLUTE SCX to give the title compound 48 (10 mg, 25%). Oxalate-salt was prepared from oxalic acid (1.1 eq.) in methanol/diethylether. $^1$H NMR (CD$_3$OD) δ 0.9 (t, 3H), 2.0 (t, 2H), 2.4 (m, 6H), 3.1 (m, 4H), 3.4 (m, 2H), 4.45 (t, 2H), 5.35 (t, 1H), 7.1 (t, 1H), 7.35 (t, 1H), 7.5 (d, 1H), 7.7 (d, 1H), 8.0 (s, 1H).

Example 45

1-Benzo[b]thiophen-2-yl-4-(4-butylpiperidin-1-yl)-butan-1-one (49) (45NK99/oxalate)

n-BuLi in heptanes (0.77 ml, 1.0 mmol, 1.3M) was added dropwise to benzo[b]thiophene (134 mg, 1.0 mmol) in THF (4 ml) at −78° C. under argon. The reaction mixture was stirred at −78° C. for 15 min, then 4-(4-butyl-piperidin-1-yl)-N-methoxy-N-methyl-butyramide (135 mg, 0.5 mmol) in THF (1 ml) was added. The reaction was stirred at −78° C. for 30 min, then NH$_4$Cl (sat. aq., 1 ml) was added and the reaction warmed to room temperature. The product was extracted with ethyl acetate (2×20 ml) and the organic layer was washed with water (10 ml), dried (K$_2$CO$_3$), filtered and concentrated in vacuo. The product was purified by column chromatography (0–25% ethyl acetate in heptanes+0.1% Et$_3$N). Yield 94 mg (55%). The oxalate salt was formed by addition of oxalic acid in diethyl ether:methanol (10:1) to give a white precipitate that was filtered and dried. $^1$H NMR (DMSO): δ 0.91 (t, 3H), 1.24–1.56 (m, 9H), 1.87 (br. d, 2H), 2.08 (m, 2H), 2.93 (m, 2H), 3.14 (m, 2H), 3.24 (m, 2H), 3.47 (m, 2H), 7.46–7.59 (m, 2H), 8.05 (m, 2H), 8.36 (s, 1H).

Example 46

4-(4-Butylpiperidin-1-yl)-1-(3-methyl-benzofuran-2-yl)-butan-1-one (50) (45NK100/oxalate)

n-BuLi in heptanes (0.85 ml, 1.1 mmol, 1.3M) was added drop wise to 3-methylbenzofuran (132 mg, 1.0 mmol) in THF (4 ml) at −78° C. under argon. The reaction mixture was stirred at −78° C. for 20 min, then 4-(4-butyl-piperidin-1-yl)-N-methoxy-N-methyl-butyramide (135 mg, 0.5 mmol) in THF (1 ml) was added. The reaction was stirred at −78° C. for 45 min, then NH$_4$Cl (sat. aq., 1 ml) was added and the reaction warmed to room temperature. The product was extracted with ethyl acetate (2×20 ml) and the organic layer was washed with water (10 ml), dried (K$_2$CO$_3$), filtered and concentrated in vacuo. The product was purified by column chromatography (0–20% ethyl acetate in heptanes+0.1% Et$_3$N). Yield 38 mg (22%). The oxalate salt was formed by addition of oxalic acid in diethyl ether:methanol (10:1) to give a white precipitate that was filtered and dried. $^1$H NMR (CD$_3$OD): δ 0.91 (t, 3H), 1.32 (m, 6H), 1.42–1.64 (m, 3H), 1.89 (br. d, 2H), 2.15 (tt, 2H), 2.58 (s, 3H) 2.96 (m, 2H), 3.17 (m, 4H), 3.60 (m, 2H), 7.33 (m, 1H), 7.52 (m, 2H), 7.71 (m, 1H).

Example 47

4-(4-Butylpiperidin-1-yl)-4-(5-fluoro-3-methyl-benzo[b]thiophen-2-yl)-butan-1-one (51) (45NK105)

n-BuLi in heptanes (0.50 ml, 0.8 mmol, 1.6M) was added drop wise to 5-fluoro-3-methyl-benzo[b]thiophene (166 mg, 1.0 mmol) in THF (4 ml) at −40° C. under argon. The reaction mixture was stirred at −40° C. for 40 min then 4-(4-butyl-piperidin-1-yl)-N-methoxy-N-methyl-butyramide (135 mg, 0.5 mmol) in THF (1 ml) was added. The reaction was stirred at −40° C. for 30 min, then NH$_4$Cl (sat. aq., 1 ml) was added and the reaction warmed to room temperature. The product was extracted with ethyl acetate (2×20 ml) and the organic layer was washed with water (10 ml), dried (K$_2$CO$_3$), filtered and concentrated in vacuo. The product was purified on a Isco CombiFlash Sq 16× (4.1 g silica column, eluting heptanes (5 min), 0–15% ethyl acetate in heptanes (20 min), 15% ethyl acetate in heptanes (15 min), all solvents+0.1% Et$_3$N). Yield 39 mg (21%). The hydrochloride salt was formed by addition of HCl (4M in dioxane) and recrystallised from methanol-diethyl ether to give a white precipitate that was filtered and dried. $^1$H NMR (free base, CDCl$_3$): δ 0.87 (t, 3H), 1.10–1.35 (m, 9H), 1.62 (br. d, 2H), 1.96 (m, 4H), 2.42 (t, 2H), 2.71 (s, 3H), 2.93 (m, 4H), 7.34 (dt, 1H), 7.49 (dd, 1H), 7.76 (dd, 1H).

Example 48

1-Benzofuran-2-yl-4-(4-butylpiperidin-1-yl)-butan-1-one (52) (45NK106)

n-BuLi in heptanes (0.50 ml, 0.8 mmol, 1.6M) was added drop wise to benzofuran (118 mg, 1.0 mmol) in THF (4 ml) at −40° C. under argon. The reaction mixture was stirred at −40° C. for 40 min, then 4-(4-butylpiperidin-1-yl)-N-methoxy-N-methyl-butyramide (135 mg, 0.5 mmol) in THF (1 ml) was added. The reaction was stirred at −40° C. for 30 min, then NH$_4$Cl (sat. aq., 1 ml) was added and the reaction warmed to room temperature. The product was extracted with ethyl acetate (2×20 ml) and the organic layer was washed with water (10 ml), dried (K$_2$CO$_3$), filtered and concentrated in vacuo. The product was purified on a Isco CombiFlash Sq 16× (4.1 g silica column, eluting heptanes (5 min), 0–15% ethyl acetate in heptanes (20 min), 15% ethyl acetate in heptanes (15 min), all solvents+0.1% Et$_3$N). Yield 61 mg (50%). The hydrochloride salt was formed by addition of HCl (4M in dioxane) and recrystallised from methanol-diethyl ether to give a white precipitate that was filtered and dried. $^1$H NMR (free base, CDCl$_3$): δ 0.87 (t, 3H), 1.10–1.30 (m, 9H), 1.59 (br. d, 2H), 1.93 (m, 2H), 1.99 (tt, 2H), 2.40 (t, 2H), 2.87 (m, 2H), 2.96 (t, 2H), 7.30 (m, 1H), 7.45 (m, 1H), 7.48 (m, 1H), 7.57 (m, 1H), 7.69 (m, 1H).

Example 49

1-(3-Bromo-benzo[b]thiophen-2-yl)-4-(4-butylpiperidin-1-yl)-butan-1-one (53) (45NK108)

t-BuLi in pentanes (0.48 ml, 0.8 mmol, 1.7M) was added drop wise to 3-bromo-benzo[b]thiophene (213 mg, 1.0 mmol) in THF (4 ml) at −78° C. under argon. The reaction mixture was stirred at −78° C. for 40 min, then 4-(4-butylpiperidin-1-yl)-N-methoxy-N-methyl-butyramide (135 mg, 0.5 mmol) in THF (1 ml) was added. The reaction was stirred at −78° C. for 30 min, then NH$_4$Cl (sat. aq., 1 ml) was added and the reaction warmed to room temperature. The product was extracted with ethyl acetate (2×20 ml) and the organic layer was washed with water (10 ml), dried (K$_2$CO$_3$), filtered and concentrated in vacuo. The product was purified on a Isco CombiFlash Sq 16× (4.1 g silica column, eluting heptanes (5 min), 0–15% ethyl acetate in heptanes (20 min), 15% ethyl acetate in heptanes (15 min), all solvents+0.1% Et$_3$N). Yield 18 mg (4%). The hydrochloride salt was formed by addition of HCl (4M in dioxane) and recrystallised from methanol-diethyl ether to give a white precipitate that was filtered and dried. $^1$H NMR (free base, CDCl$_3$): δ 0.88 (t, 3H), 1.12–1.28 (m, 9H), 1.62 (br. d, 2H), 1.94 (m, 2H), 2.02 (tt, 2H), 2.45 (t, 2H), 2.92 (br. d, 2H), 31.8 (t, 2H), 7.51 (m, 2H), 7.83 (m, 1H), 7.98 (m, 1H).

Example 50

1-(3-Benzo[b]thiophen-2-yl-propyl)-4-butylpiperidine (54) (45NK124)

n-BuLi in heptanes (0.75 ml, 1.2 mmol, 1.6M) was added drop wise to benzo[b]thiophene (134 mg, 1.0 mmol) in THF (4 ml) at −5° C. under argon. The reaction mixture was stirred at −5° C. for 15 min, then 1-chloro-3-iodopropane (151 μl, 1.2 mmol) and copper (I) iodide (19 mg, 0.1 mmol) were added. The reaction was stirred at −5° C. for 1 h, then at room temperature for 0.5 h. Water (5 ml) was added, the product was extracted with diethyl ether (2×10 ml) and the organic layer was dried (K$_2$CO$_3$), filtered and concentrated in vacuo. The product was purified by column chromatography (0–2% ethyl acetate in heptanes) to give 2-(3-chloro-propyl)-benzo[b]thiophene (93 mg, 44%). $^1$H NMR (CDCl$_3$): δ 2.22 (tt, 2H), 3.10 (dt, 2H), 3.61 (t, 2H), 7.06 (m, 1H), 7.30 (m, 2H), 7.69 (m, 1H), 7.78 (m, 1H). 2-(3-Chloropropyl)-benzo[b]thiophene (53 mg, 0.25 mmol), 4-butylpiperidine (36 mg, 0.25 mmol), sodium iodide (75 mg, 0.5 mmol) and sodium carbonate (53 mg, 0.5 mmol) in acetonitrile (2 ml) were shaken at 80° C. for 18 h, then the reaction was cooled to room temperature. Water (5 ml) was added and the product was extracted with ethyl acetate (2×10 ml), dried (K$_2$CO$_3$), filtered and concentrated in vacuo. The product was purified by column chromatography (0–15% ethyl acetate in heptanes+0.1% Et$_3$N) to yield the title compound 54. Yield 29 mg (37%). The hydrochloride salt was formed by addition of HCl (4M in dioxane) and recrystallised from methanol-diethyl ether to give a white precipitate that was filtered and dried. $^1$H NMR (CD$_3$OD): δ 0.91 (t, 3H), 1.32 (m, 6H), 1.39 (m, 2H), 1.55 (m, 1H), 1.96 (br. d, 2H), 2.19 (tt, 2H), 2.93 (m, 2H), 3.04 (t, 2H), 3.14 (m, 2H), 3.53 (m, 2H), 7.14 (br. s, 1H), 7.26 (m, 1H), 7.31 (m, 1H), 7.68 (m, 1H), 7.77 (m, 1H).

Example 51

1-(3-Benzofuran-2-yl-propyl)-4-butylpiperidine (55) (56NK03)

n-BuLi in heptanes (1.5 ml, 2.4 mmol, 1.6M) was added drop wise to benzofuran (236 mg, 2.0 mmol) in THF (5 ml) at −20° C. under argon. The reaction mixture was stirred at −15° C. for 30 min, then 1-chloro-3-iodopropane (322 μl, 3.0 mmol) and copper (I) iodide (38 mg, 0.2 mmol) were added. The reaction was stirred at −15° C. for 1 h, then NH$_4$Cl (sat. aq., 5 ml) was added. The product was extracted with diethyl ether (2×30 ml) and the organic layer was washed with brine (10 ml), dried (K$_2$CO$_3$), filtered and concentrated in vacuo. The product was purified by column chromatography (0–1% diethyl ether in heptanes) to give 2-(3-chloro-propyl)-benzofuran (101 mg, 26%). $^1$H NMR (CDCl$_3$): δ 2.23 (tt, 2H), 2.97 (dt, 2H), 3.62 (t, 2H), 6.45 (q, 1H), 7.21 (m, 2H), 7.42 (m, 1H), 7.50 (m, 1H).

2-(3-Chloro-propyl)-benzofuran (101 mg, 0.52 mmol), 4-butylpiperidine (74 mg, 0.52 mmol), sodium iodide (156 mg, 1.04 mmol) and sodium carbonate (110 mg, 1.04 mmol) in acetonitrile (2 ml) were shaken at 80° C. for 18 h, then the reaction was cooled to room temperature. Water (1 ml) was added, the product was extracted with ethyl acetate (2×2 ml), and the organic layer loaded onto a Varian SCX ion exchange column. The column was washed with methanol (2 column volumes) and the product was eluted from the column using 10% ammonium hydroxide in methanol (2 column volumes). The solute was concentrated in vacuo, dissolved up in acetone, dried ($K_2CO_3$) and concentrated in vacuo. The product was purified by column chromatography (0–12% ethyl acetate in heptanes+0.1% $Et_3N$) to yield the title compound 55. Yield 86 mg (55%). The hydrochloride salt was formed by addition of HCl (4M in dioxane) and recrystallised from methanol-diethyl ether to give a white flaky solid that was filtered and dried. $^1$H NMR ($CD_3OD$): δ 0.90 (t, 3H), 1.30 (m, 6H), 1.48 (m, 3H), 1.95 (br. d, 2H), 2.21 (m, 4H), 2.91 (m, 4H), 3.16 (m, 2H), 3.55 (br. d, 2H), 6.57 (s, 1H), 7.17 (m, 2H), 7.38 (m, 2H), 7.48 (m, 1H).

Example 52

4-Butyl-1-[3-(3-methyl-benzofuran-2-yl)-propyl]-piperidine (56) (56NK04)

n-BuLi in heptanes (1.5 ml, 2.4 mmol, 1.6M) was added drop wise to 3-methylbenzofuran (264 mg, 2.0 mmol) in THF (5 ml) at −20° C. under argon. The reaction mixture was stirred at −15° C. for 30 min, then 1-chloro-3-iodopropane (322 μl, 3.0 mmol) and copper (I) iodide (38 mg, 0.2 mmol) were added. The reaction was stirred at −15° C. for 1 h, then $NH_4Cl$ (sat'd aq., 5 ml) was added. The product was extracted with diethyl ether (2×30 ml) and the organic layer was washed with brine, (10 ml) dried ($K_2CO_3$), filtered and concentrated in vacuo. The product was purified by column chromatography (0–1% diethyl ether in heptanes) to give 2-(3-chloro-propyl)-3-methylbenzofuran (25 mg, 6%). $^1$H NMR ($CDCl_3$): δ 2.19 (tt, 2H), 2.22 (s, 3H), 2.94 (t, 2H), 3.57 (t, 2H), 7.22 (m, 2H), 7.38 (m, 1H), 7.44 (m, 1H).

2-(3-Chloro-propyl)-3-methylbenzofuran (25 mg, 0.12 mmol), 4-butylpiperidine (17 mg, 0.12 mmol), sodium iodide (35 mg, 0.24 mmol) and sodium carbonate (25 mg, 0.24 mmol) in acetonitrile (2 ml) were shaken at 80° C. for 18 h, then the reaction was cooled to room temperature. Water (1 ml) was added, the product was extracted with ethyl acetate (2×2 ml) and the organic layer loaded onto a Varian SCX ion exchange column. The column was washed with methanol (2 column volumes), then the product was eluted from the column using 10% ammonium hydroxide in methanol (2 column volumes). The solute was concentrated in vacuo, dissolved in acetone, dried ($K_2CO_3$) and concentrated in vacuo. The product was purified by column chromatography (0–12% ethyl acetate in heptanes+0.1% $Et_3N$) to yield the title compound 56. Yield 14 mg (38%). The hydrochloride salt was formed by addition of HCl (4M in dioxane) and recrystallised from methanol-diethyl ether to give a white solid that was filtered and dried. $^1$H NMR ($CD_3OD$): δ 0.91 (t, 3H), 1.28–1.45 (m, 8H), 1.55 (m, 1H), 1.96 (br. d, 2H), 2.17 (m, 2H), 2.22 (s, 3H), 2.89 (t, 2H), 2.94 (m, 2H), 3.14 (m, 2H), 3.54 (m, 2H), 7.20 (m, 2H), 7.34 (m, 1H), 7.45 (m, 1H).

Example 53

4-Butyl-1-[3-(5-fluoro-3-methyl-benzo[b]thiophen-2-yl)-propyl]-piperidine (57) (56NK05)

n-BuLi in heptanes (1.5 ml, 2.4 mmol, 1.6M) was added drop wise to 5-fluoro-3-methyl-benzo[b]thiophene (332 mg, 2.0 mmol) in THF (5 ml) at −20° C. under argon. The reaction mixture was stirred at −15° C. for 30 min, then 1-chloro-3-iodopropane (322 μl, 3.0 mmol) and copper (1) iodide (38 mg, 0.2 mmol) were added. The reaction was stirred at −15° C. for 1 h, then $NH_4Cl$ (sat'd aq., 5 ml) was added. The product was extracted with diethyl ether (2×30 ml) and the organic layer was washed with brine (10 ml), dried ($K_2CO_3$), filtered and concentrated in vacuo. The product was purified by column chromatography (0–1% diethyl ether in heptanes) to give 2-(3-chloro-propyl)-5-fluoro-3-methyl-benzo[b]thiophene (180 mg, 37%). $^1$H NMR ($CDCl_3$): δ 2.19 (tt, 2H), 2.22 (s, 3H), 2.94 (t, 2H), 3.57 (t, 2H), 7.04 (dt, 1H), 7.28 (dd, 1H), 7.66 (dd, 1H).

2-(3-Chloro-propyl)-5-fluoro-3-methyl-benzo[b]thiophene (180 mg, 0.74 mmol), 4-butylpiperidine (212 mg, 0.74 mmol), sodium iodide (225 mg, 1.48 mmol) and sodium carbonate (159 mg, 1.48 mmol) in acetonitrile (2 ml) were shaken at 80° C. for 18 h, then the reaction was cooled to room temperature. Water (1 ml) was added, the product was extracted with ethyl acetate (2×2 ml), and the organic layer loaded onto a Varian SCX ion exchange column. The column was washed with methanol (2 column volumes), then the product was eluted from the column using 10% ammonium hydroxide in methanol (2 column volumes). The solute was concentrated in vacuo, dissolved in acetone, dried ($K_2CO_3$) and concentrated in vacuo. The product was purified by column chromatography (0–12% ethyl acetate in heptanes+0.1% $Et_3N$) to yield the title compound 57. Yield 185 mg (72%). The hydrochloride salt was formed by addition of HCl (4M in dioxane) and recrystallised from methanol-diethyl ether to give white crystals that were filtered and dried. $^1$H NMR ($CD_3OD$): δ 0.90 (t, 3H), 1.31 (m, 6H), 1.37–1.62 (m, 3H), 1.94 (br. d, 2H), 2.15 (m, 2H), 2.31 (s, 3H), 2.92 (br. t, 2H), 3.01 (tm, 2H), 3.14 (m, 2H), 3.54 (br. d, 2H), 7.06 (dt, 2H), 7.34 (dd, 1H), 7.73 (dd, 1H).

Example 54

2-(3-Iodo-propyl)-benzo[b]thiophene (58)

A mixture of 2-(3-Chloro-propyl)-benzo[b]thiophene (902 mg, 4.28 mmol) and sodium iodide (1.29 g, 8.6 mmol) was heated to 50° C. in acetone (5 ml) for 72 h, then cooled to room temperature. Aqueous sodium thiosulphate (1 M, 10 ml) was added and the product was extracted with diethyl ether (2×20 ml). The organic layer was dried ($K_2CO_3$), filtered and concentrated in vacuo to give a white solid that was filtered through Celite and eluted with heptanes. The filtrate was concentrated in vacuo to give a white solid. Yield 1.038 g (80%). $^1$H NMR ($CDCl_3$): δ 2.24 (tt, 2H), 3.04 (dt, 2H), 3.27 (t, 2H), 7.07 (q, 1H), 7.28 (m, 2H), 7.68 (m, 1H), 7.77 (m, 1H).

General Procedure for the Alkylation of Amines.

2-(3-Iodo-propyl)-benzo[b]thiophene (33 mg, 0.11 mmol) in DCM (240 μl) was added to the amine (0.10 mmol) in DCM (200 μl) and the reaction was shaken at room temperature for 18 h. DCM (1 ml) was added followed by macroporous triethylammonium methylpolystyrene carbonate (50 mg, 3.06 mmol/g loading, Argonaut Technologies) and the reaction was shaken at room temperature for 1 h. Polystyrene methylisocyanate (60 mg, 1.25 mmol/g, Argonaut Technologies) was added and the reaction was shaken at room temperature for 2 h. The reaction was than loaded onto a Varian SCX ion exchange column. The column was washed with methanol (2 column volumes) and the product was eluted from the column using 10% ammonium hydrox-

Example 55

1-(3-Benzo[b]thiophen-2-yl-propyl)-4-methylpiperidine (59) (56NK38)

The reaction was carried out according to the general procedure using 4-methyl-piperidine (17 mg, 0.10 mmol) to yield 14 mg (53%) of 1-(3-benzo[b]thiophen-2-yl-propyl)-4-methylpiperidine. $^1$H NMR (CD$_3$OD): δ 0.92 (d, 3H), 1.27 (m, 2H), 1.34 (m, 1H), 1.63 (m, 2H), 1.94 (m, 4H), 2.40 (t, 2H), 2.91 (m, 4H), 7.00 (d, 1H), 7.28 (m, 2H), 7.66 (m, 1H), 7.76 (m, 1H).

Example 56

1-(3-Benzo[b]thiophen-2-yl-propyl)-4-benzylpiperidine (60) (56NK40)

The reaction was carried out according to the general procedure using 4-benzyl-piperidine (17 mg, 0.10 mmol) to yield 16 mg (45%) of 1-(3-benzo[b]thiophen-2-yl-propyl)-4-benzyl-piperidine. $^1$H NMR (CD$_3$OD): δ 1.29 (m, 2H), 1.47–1.67 (m, 4H), 1.92 (m, 4H), 2.38 (m, 2H), 2.52 (m, 3H), 2.88 (m, 4H), 7.03 (m, 1H), 7.10–7.15 (m, 3H), 7.18–7.28 (m, 4H), 7.63 (m, 1H), 7.72 (m, 1H).

Example 57

1-(3-Benzo[b]thiophen-2-yl-propyl)-4-(2-methoxyphenyl)-piperidine (61) (56NK42)

The reaction was carried out according to the general procedure using 4-(2-methoxy-phenyl)-piperidine (17 mg, 0.10 mmol) to yield 17 mg (47%) of 1-(3-benzo[b]thiophen-2-yl-propyl)-4-(2-methoxy-phenyl)-piperidine. $^1$H NMR (CD$_3$OD): δ 1.77 (m, 4H), 1.98 (m, 2H), 2.10 (m, 2H), 2.46 (m, 2H), 2.94 (m, 3H), 3.04 (m, 2H), 3.79 (s, 3H), 6.88 (m, 2H), 7.06 (br. s, 1H), 7.13 (m, 2H), 7.26 (m, 2H), 7.65 (m, 1H), 7.73 (m, 1H).

Example 58

2-(3-Bromopropyl)-2H-benzotriazole (35AKU-17-2) (62)

To a solution of 1,3-dibromopropane (510 μl, 5.0 mmol) in dimethylformamide (10 ml) was added benzotriazole (600 mg, 5.0 mmol) and KOH (430 mg, 7.7 mmol). After stirring for 20 h at room temp, water (10 ml) and ethyl acetate (10 ml) were added. The phases were separated and the aqueous phase was re-extracted with ethyl acetate (3×15 ml). The combined organic phases were dried over MgSO4 and concentrated in vacuo, giving 1.44 g of the crude material. The crude product was purified by flash chromatography (0–10% methanol in DCM), yielding 274 mg (23%) of the title compound 62. TLC (5% methanol in DCM): $R_f$=0.7. $^1$H-NMR (400 MHz, CDCl$_3$): δ=7.88–7.83 (2H, m); 7.41–7.36 (2H, m); 4.91 (2H, t); 3.44 (2H, t); 2.66 (2H, m).

Example 59

2-[3-(4-Butylpiperidin-1-yl)-propyl]-2H-benzotriazole (63) (35AKU-18)

To a solution of 2-(3-bromopropyl)-2H-benzotriazole (274 mg, 1.14 mmol) in dimethylformamide (5 ml) was added a solution of 4-butylpiperidine (142 mg, 1.0 mmol) and KOH (125 mg, 2.2 mmol) in dimethylformamide (5 ml). The mixture was stirred for 20 h at room temp., and ethyl acetate (10 ml) and water (10 ml) were then added. The phases were separated and the aqueous phase was re-extracted with ethyl acetate (3×20 ml). The combined organic phases were dried over MgSO4 and concentrated in vacuo to produce 383 mg of the crude material. The crude product was purified by flash chromatography (0–10% methanol in DCM) yielding 232 mg (77%) of the title compound 63. The oxalate-salt was prepared from oxalic acid (1.1 eq.) in diethyl ether. TLC (10% methanol in DCM): $R_f$=0.4. HPLC-MS (Method A): M$^+$=301.2 (UV/MS(%)=100/89). $^1$H-NMR (400 MHz, CDCl$_3$): δ=7.86 (2H, m); 7.37 (2H, m); 4.78 (2H, t); 2.93 (2H, d); 2.45 (2H, d); 2.34 (2H, m); 1.94 (2H, t); 1.61 (2H, d); 1.32–1.13 (9H, m); 0.88 (3H, t).

Example 60

1-(3-Bromopropyl)-1H-benzotriazole (35AKU-17-1) (64)

To a solution of 1,3-dibromopropane (510 μl, 5.0 mmol) in dimethylformamide (10 ml) was added benzotriazole (600 mg, 5.0 mmol) and KOH (430 mg, 7.7 mmol). After stirring for 20 h at room temp., water (15 ml) and ethyl acetate (15 ml) were added. The phases were separated and the aqueous phase was re-extracted with ethyl acetate (3×20 ml). The combined organic phases were dried over MgSO4 and concentrated, giving 1.44 g of the crude product. The crude product was purified by flash chromatography (0–10% methanol in DCM) yielding 705 mg (59%) of the title compound 64. TLC (5% methanol in DCM): $R_f$=0.4. HPLC-MS (Method A): M$^+$=239.9 (UV/MS(%)=52/58).

Example 61

1-[3-(4-Butylpiperidin-1-yl)-propyl]-1H-benzotriazole (65) (35AKU-19)

To a solution of 1-(3-bromopropyl)-1H-benzotriazole (705 mg, 1.6 mmol) in dimethylformamide (5 ml) was added a solution of 4-butylpiperidine (140 mg, 1.0 mmol) and KOH (240 mg, 4.3 mmol) dissolved in dimethylformamide (5 ml). The mixture was stirred for 20 h at room temp. Ethyl acetate (10 ml) and water (10 ml) were then added. The phases were separated and the aqueous phase was re-extracted with ethyl acetate (3×15 ml). The combined organic phases were washed with brine, dried over MgSO4 and evaporated to dryness, giving 776 mg of the crude material. The crude product was purified by flash chromatography (0–10% methanol in DCM) yielding 146 mg (49%) of the title compound 65. The oxalate-salt was prepared from oxalic acid (1.1 eq.) in diethyl ether. TLC (10% methanol in DCM): $R_f$=0.4. HPLC-MS (Method A): M$^+$=301.2 (UV/MS(%)=100/99). $^1$H-NMR (400 MHz, CDCl$_3$): δ=8.05 (1H, m); 7.62–7.33 (3H, m); 4.71 (2H, t); 2.85 (2H, d); 2.34 (2H, m); 2.22 (2H, m); 1.90 (2H, t); 1.67 (2H, d); 1.33–1.16 (9H, m); 0.89 (3H, t).

Example 62

1-[3-(4-Butylpiperidin-1-yl)-propyl]-1H-indole-3-carbaldehyde (66) (35AKU-24)

To a solution of 1,3-dibromopropane (410 μl, 4.0 mmol) in dimethylformamide (5 ml) was added a solution of 1H-indole-3-carboxaldehyde (582 mg, 4.0 mmol) and KOH (456 mg, 8.1 mmol) in dimethylformamide (5 ml). After stirring for 24 h, 4-butylpiperidine (359 mg, 2.0 mmol) and additional KOH (200 mg, 3.6 mmol) were added. After stirring for 20 h, water and ethyl acetate were added. The phases were separated and the aqueous phase was re-extracted with ethyl acetate (3×15 ml). The combined organic phases were washed with brine, dried over MgSO4 and evaporated to dryness, giving 1.04 g of the crude product. The crude product was purified by flash chromatography (0–10% methanol in DCM) yielding 252 mg (39%) of the title compound 66. TLC (10% methanol in DCM): $R_f$=0.5. HPLC-MS (Method A): $M^+$=327.2 (UV/MS(%)=99/96).

Example 63

{1-[3-(4-Butylpiperidin-1-yl)-propyl]-1H-indol-3-yl}-methanol (67) (35AKU-26)

To a solution of 1-[3-(4-butylpiperidin-1-yl)-propyl]-1H-indole-3-carbaldehyde (120 mg, 0.37 mmol) in methanol (2 ml) was slowly added a solution of $NaBH_4$ (9.2 mg, 0.24 mmol) in 20 μl of 2M NaOH/1 ml of water. The mixture was then stirred for 20 h at room temp. Additional $NaBH_4$ (12 mg, 0.32 mmol) was added and the mixture stirring for an additional 2 h. Another portion of $NaBH_4$ (14 mg, 0.37 mmol) was added and the mixture was stirred overnight. Methanol was partly removed using a Rotavap, and ethyl acetate (10 ml) and water (10 ml) were added. The phases were separated and the aqueous phase was re-extracted with ethyl acetate (3×15 ml). The combined organic phases were dried over MgSO4 and evaporated to dryness giving 93 mg (71%) of the title compound 67. TLC (10% methanol in DCM): $R_f$=0.4. HPLC-MS (Method A): $M^+$=329.2 (UV/MS (%)-98/79). $^1$H-NMR (400 MHz, CDCl$_3$): δ=7.72 (1H, d); 7.36 (1H, d); 7.25–7.10 (3H, m); 4.86 (1H, s); 4.15 (2H, t); 2.84 (2H, d); 2.26 (2H, t); 1.99 (2H, m); 1.86 (2H, t); 1.71–1.62 (4H, m); 1.34–1.16 (9H, m); 0.90 (3H, t).

Example 64

1-[3-(4-Butylpiperidin-1-yl)-propyl]-2-phenyl-1H-benzoimidazole (68) (35AKU-28)

To a solution of 1,3-dibromopropane (205 μl, 2.0 mmol) in dimethylformamide (5 ml) was added 2-phenylbenzimidazole (389 mg, 2.0 mmol) and KOH (266 mg, 4.7 mmol). After stirring for 16 h at room temp., 4-butylpiperidine hydrochloride (176 mg, 1.0 mmol) was added. After 24 h stirring, additional KOH (270 mg, 4.8 mmol) was added and the mixture heated at 90° C. for 3 h. After cooling, water (10 ml) and ethyl acetate (10 ml) were added. The phases were separated and the aqueous phase was re-extracted with ethyl acetate (3×15 ml). The combined organic phases were washed with brine, dried over MgSO4 and concentrated in vacuo to produce 643 mg of the crude material. The crude product was purified by flash chromatography (0–10% methanol in DCM) yielding 71 mg (19%) of the title compound 68. TLC (10% methanol in DCM): $R_f$=0.7. HPLC-MS (Method A): $M^+$=376.3 (UV/MS(%)=100/100). $^1$H-NMR (400 MHz, CDCl$_3$): δ=7.85–7.27 (9H, m); 4.32 (2H, t); 2.73 (2H, d); 2.25 (2H, t); 1.95 (2H, m); 1.81 (2H, t); 1.62 (2H, d); 1.33–1.08 (9H, m); 0.90 (3H, t).

Example 65

1-[3-(4-Butylpiperidin-1-yl)-propyl]-3-chloro-1H-indazole (69) (35AKU-34)

To a solution of 1,3-dibromopropane (205 μl, 2.0 mmol) in dimethylformamide (5 ml) was added 3-chloroindazole (306 mg, 2.0 mmol) and KOH (400 mg, 7.1 mmol). After stirring the suspension for 16 h, 4-butylpiperidine hydrochloride (180 mg, 1.0 mmol) and dimethylformamide (2 ml) were added. After 20 h stirring, water (10 ml) and ethyl acetate (10 ml) were added. The phases were separated and the aqueous phase was re-extracted with ethyl acetate (3×15 ml). The combined organic phases were washed with brine, dried over MgSO4 and concentrated in vacuo to give 500 mg of the crude product. The crude product was purified by flash chromatography (0–10% methanol in DCM) yielding 121 mg (36%) of the title compound 69. The oxalate-salt was prepared from oxalic acid (1.1 eq.) in diethyl ether. TLC (10% methanol in DCM): $R_f$=0.5. HPLC-MS (Method A): $M^+$=334.1 (UV/MS(%)=100/100). $^1$H-NMR (400 MHz, CDCl$_3$): δ 7.68–7.16 (4H, m); 4.43 (2H, t); 3.13 (2H, d); 2.62 (2H, t); 2.35 (2H, m); 2.22 (2H, t); 1.76 (2H, d); 1.61–1.46 (2H, m); 1.36–1.24 (7H, m); 0.89 (3H, t).

Example 66

1-[3-(4-Butylpiperidin-1-yl)-propyl]-6-nitro-1H-indazole (70) (35AKU40)

To a solution of 1,3-dibromopropane (205 μl, 2.0 mmol) in dimethylformamide (20 ml) was added 6-nitroindazole (325 mg, 2.0 mmol) and $K_2CO_3$ (590 mg, 4.3 mmol). After stirring the suspension for 20 h, 4-butylpiperidine hydrochloride (178 mg, 1.0 mmol) and dimethylformamide (5 ml) were added. After 20 h stirring, water (15 ml) and ethyl acetate (15 ml) were added. The phases were separated and the aqueous phase was re-extracted with ethyl acetate (3×20 ml). The combined organic phases were washed with brine, dried over MgSO4 and concentrated in vacuo to produce 511 mg of the crude product. The crude product was purified by ion exchange chromatography (washout with 10% aq. $NH_4OH$ (25%) in methanol) and flash chromatography (0–10% methanol in DCM) yielding 21 mg (6%) of the title compound 70. The oxalate-salt was prepared from oxalic acid (1.1 eq.) in diethyl ether. TLC (10% methanol in DCM): $R_f$=0.4. HPLC-MS (Method A): $M^+$=345.1 (UV/MS(%)=97/96). $^1$H-NMR (400 MHz, CDCl$_3$): δ=8.70 (1H, m); 8.07 (1H, m); 7.90 (1H, m); 7.75 (1H, m); 4.56 (2H, t); 2.86 (2H, d); 2.32 (2H, t); 2.24 (2H, m); 1.92 (2H, t); 1.68 (2H, m); 1.35–1.16 (9H, m); 0.89 (3H, t).

Example 67

Benzo[d]isoxazol-3-ol (35AKU-44) (71)

To a solution of salicylhydroxamic acid (1.53 g, 10 mmol) in THF (40 ml) was added a solution of carbonyldiimidazole (1.62 g, 20 mmol) in tetrahydrofuran (20 ml). The mixture was stirred at reflux for 4 hrs. before evaporation to dryness. Water (20 ml) and conc. HCl (aq.) (5 ml) were added and the solution was refrigerated (5° C.) for 30 min. The resulting precipitate was collected by filtration and washed with 2M HCl. The solid material was dissolved in methanol and concentrated in vacuo yielding 725 mg (54%) of the title compound 71. TLC (10% methanol in DCM): $R_f$=0.2. HPLC-MS (Method A): $M^+$=136.1 (UV/MS(%)=94/100). $^1$H-NMR (400 MHz, CDCl$_3$, MeOD): δ=7.73 (1H, m); 7.56 (1H, m); 7.38 (1H, m); 7.28 (1H, m); 3.87 (1H, s).

Example 68

3-(2-Chloroethoxy)-benzo[d]isoxazole (35AKU-45 (72))

To a solution of 1-bromo-2-chloroethane (250 μl, 3.0 mmol) in dimethylformamide (10 ml) was added benzo[d]

isoxazol-3-ol (400 mg, 3.0 mmol) and $K_2CO_3$ (440 mg, 3.2 mmol). The mixture was stirred for 20 h and then heated at 80° C. for 1 hr. Ethyl acetate (10 ml) and water (10 ml) were added. The phases were separated and the aqueous phase was re-extracted with ethyl acetate (3×15 ml). The combined organic phases were washed with brine, dried over MgSO4 and concentrated in vacuo to give 543 mg of the crude product. The crude product was purified by flash chromatography (0–10% methanol in DCM) yielding 378 mg (64%) of the title compound 72. TLC (10% methanol in DCM): $R_f$=0.8. $^1$H-NMR (400 MHz, $CDCl_3$): δ=7.68 (1H, d); 7.55 (1H, t); 7.44 (1H, d); 7.28 (1H, t); 4.72 (2H, t); 3.94 (2H, t).

Example 69

3-[2-(4-Butylpiperidin-1-yl)-ethoxy]-benzo[d]isoxazol (73) (35AKU-46)

A solution of 3-(2-chloroethoxy)-benzo[d]isoxazole (378 mg, 1.9 mmol), 4-butylpiperidine hydrochloride (270 mg, 1.5 mmol) and $K_2CO_3$ (537 mg, 3.9 mmol) dissolved in dimethylformamide (15 ml) was heated to 80° C. and stirred for 24 h. After cooling to room temp., water (15 ml) and ethyl acetate (15 ml) were added. The phases were separated and the aqueous phase was re-extracted with ethyl acetate (3×20 ml). The combined organic phases were washed with brine, dried over MgSO4 and concentrated in vacuo to give 586 mg of the crude material. The crude product was purified by flash chromatography (0–5% methanol in DCM) yielding 157 mg (35%) of the title compound 73. The oxalate-salt was prepared from oxalic acid (1.1 eq.) in diethyl ether. TLC (5% methanol in DCM): $R_f$=0.3. HPLC-MS (Method A): $M^+$=303.1 (UV/MS(%)=100/100). $^1$H-NMR (400 MHz, $CDCl_3$): δ=7.69–7.22 (4H, m); 4.57 (2H, t); 2.99 (2H, d); 2.88 (2H, t); 2.11 (2H, t); 1.68 (2H, m); 1.32–1.18 (9H, m); 0.89 (3H, t).

Example 70

3-(1H-Indol-3-yl)-propan-1-ol (74) (32HS28)

A suspension of lithiumaluminium hydride (4.68 g, 126 mmol) in anhydrous diethyl ether (230 ml) was stirred heavily. 3-Indolepropionic acid (10.0 g, 53 mmol) was dissolved in anhydrous diethyl ether and added drop wise while the reaction was at reflux. The reaction mixture was further refluxed for 2 h and then stirred at room temperature (rt) overnight. Water (25 ml) was added slowly, followed by an aqueous solution of $H_2SO_4$ (1:3 $H_2O$/conc. $H_2SO_4$) (20 ml). The resulting clear mixture was extracted with diethyl ether (3×110 ml), and the combined organic phases were washed with brine, dried ($Na_2SO_4$) filtered and concentrated in vacuo to give a crude oil of the title compound (74) (1.8 g). The crude material was used without further purification.

Example 71

3-[3-(4-Butyl-piperidin-1-yl)-propyl]-1H-indole hydrochloride (75) (32HS34)

The crude 3-(1H-indol-3-yl)-propan-1-ol (1.8 g) was dissolved in anhydrous THF and cooled to −40° C. Triethylamine (720 mg, 7.1 mmol) was added by syringe, followed by methanesulfonyl chloride (750 mg, 6.5 mmol). The mixture was allowed to warm to 20° C., and then filtered and concentrated in vacuo to yield a crude product that was redissolved in DCM and washed with water. The organic phase was dried over MgSO4, filtered and concentrated in vacuo to a brown oil. This material was used immediately without further purification.

4-n-Butylpiperidine hydrochloride (967 mg, 5.4 mmol) and $Na_2CO_3$ (1.28 g, 12 mmol) were suspended in DME, stirred at rt for 30 min, and then added to the crude material in DME. The resulting mixture was stirred at 82° C. overnight. The mixture was cooled prior to addition of ethyl acetate (15 ml) and water (15 ml), extracted with ethyl acetate (3×20 ml). The combined organic phases were washed with brine, dried ($Na_2SO_4$) and concentrated in vacuo. Purification by preparative HPLC followed by treatment with HCl in dioxane (4M, 2 ml) produced the title compound (75) as white crystals after washing with DCM. Yield: 130 mg, 0.3% (overall). HPLC-MS (Method A): $M^+$=298.3 (UV/MS(%)=100/100). $^1$H-NMR (400 MHz, $CD_3OD$): δ 7.55 (d, 1H), 7.34 (d, 1H), 7.09 (m, 2H), 7.01 (t, 1H9), 3.46 (m, 2H), 3.09 (m, 2H), 2.87 (m, 5H), 2.14 (m, 2H) 1.91 (2, 2H), 1.58–1.24 (m, 9H), 0.90 (t, 3H).

Example 72

4-(4-Butylpiperidine-1-yl)-butyric acid methyl ester (76) (40-LH-58)

To a solution of 4-bromo-butyric acid methyl ester (1.35 g, 7.5 mmol) in dry acetonitrile (10 ml) was added 4-butylpiperidine (1.00 g, 7.1 mmol) and $K_2CO_3$ (1.10 g, 7.8 mmol). After stirring at rt for 12 h, the reaction mixture was evaporated to dryness followed by addition of water (15 ml). The aqueous phase was extracted with ethyl acetate (3×20 ml) and the combined organic phases were dried ($Na_2SO_4$) and concentrated in vacuo to produce 1.71 g of the crude title compound 76. The crude product was purified by flash chromatography (MeOH:ethyl acetate; 2:8) to give the pure title compound. Yield 1.27 g (74%). $^1$H NMR ($CD_3OD$): δ 3.65 (s, 3H), 2.93 (d, 2H), 2.33 (q, 4H), 1.98 (t, 2H), 1.81 (qv, 2H), 1.69 (d, 2H), 1.35–1.18 (m, 9H), 0.90 (t, 3H).

Example 73

2-[3-(4-Butylpiperidin-1-yl)-propyl]-1-methyl-1H-benzimidazole (77) (40-LH-59B)

A mixture of N-methyl-benzene-1,2-diamine (68 mg, 0.56 mmol) and 4-(4-Butylpiperidin-1-yl)-butyric acid methyl ester (130 mg, 0.54 mmol) in polyphosphoric acid (1 ml) was heated and shaken in a sealed vial at 150° C. for 1.5 h. The reaction mixture was poured into an ice-cold bath (NaOH (4N): ice 1:1) with stirring, upon which a grey precipitate formed. The grey solid was filtered and washed with cold ether. The oxalate-salt was prepared from oxalic acid (1.1 eq.) in diethyl ether. Yield 141 mg (92%). $^1$H NMR ($CDCl_3$): δ 7.71 (m, 1H), 7.30–7.19 (m, 3H), 3.74 (s, 3H), 2.90 (q, 4H), 2.43 (t, 2H), 2.06 (qv, 2H), 1.89 (t, 2H), 1.65 (d, 2H), 1.31–1.14 (m, 9H), 0.89 (t, 3H).

Example 74

1H-Indazole-3-carboxylic acid (2-(4-butylpiperidin)-1-yl-ethyl)-amide (78)(40-LH-70-17B)

To a shaken solution of 1H-indazole-3-carboxylic acid (49 mg, 0.30 mmol) and N-hydroxysuccinimide (36 mg, 0.31 mmol) in dry DMF (2 ml) was added a solution of dicyclohexylcarbodiimide (62 mg, 0.30 mmol) in dry DMF (1 ml). The mixture was shaken for 16 h followed by addition of 2-(4-butylpiperidin-1-yl)-ethylamine (28 mg, 0.15 mmol). The reaction mixture was further shaken for another 24 h followed by filtration. The organic phase was loaded onto a Varian SCX ion exchange column. The column was washed sequentially with methanol (5 ml), isopropanol (5 ml), and methanol (5 ml). The product was eluted from the column using 5% ammonium in methanol (5 ml). The solute was concentrated in vacuo, dissolved in acetone, dried ($K_2CO_3$) and concentrated in vacuo to produce the title compound 78. Yield 47 mg (95%). $^1$H NMR ($CD_3OD$): δ 8.21 (d, 1H), 7.56 (d, 1H), 7.40 (dt, 1H), 7.24 (dt, 1H), 3.59 (t, 2H), 3.01 (bd, 2H), 2.63 (t, 2H), 2.08 (t, 2H), 1.71 (d, 2H), 1.34–1.21 (m, 9H), 0.90 (t, 3H).

Example 75

1-[3-(4-Butylpiperidin-1-yl)-propyl]-5-nitro-1H-indazole (79) (64LHY29-1); and Example 76. 2-[3-(4-butylpiperidin-1-yl)-propyl]-5-nitro-2H-indazole (80) (64LHY29-2)

To a cooled solution (−78° C.) of 5-nitroindazole (41.20 mg, 0.25 mmol) in THF (1 ml) was added a solution of n-buthyllithium in hexane (1.5 M, 0.17 ml, 0.25 mmol) followed by addition of 1-bromo-3-iodopropane (27 µl, 0.25 mmol). After 16 h at rt the mixture was concentrated in vacuo. Methyl ethylketone (1 ml) and 4-butylpiperidine (35.3 mg, 0.25 mmol) were added. The reaction mixture was shaken for 16 h at 60° C. followed by filtration, and the organic layer was then evaporated to dryness. The solid was dissolved in methanol (1 ml) prior to loading onto a Varian SCX ion exchange resin column. The column was washed with methanol (3×6 ml) and the product eluted with 10% $NH_3$ in methanol (5 ml). The solute was concentrated in vacuo. The two isomers were formed at a 1:1 ratio according to LC-MS analysis of the crude mixture. The two isomers were isolated after purification by preparative HPLC. 79 (64LHY29-1): $^1$H-NMR ($CDCl_3$): δ 0.88 (t, 3H), 1.18–1.33 (m, 9H), 1.73–1.64 (bd. d, 2H), 1.92 (bd. t, 2H), 2.21 (ddd, 2H), 2.30 (dd, 2H), 2.85 (bd. d, 2H), 4.55 (t, 2H), 7.75 (ddd, 1H), 8.10 (dd, 1H), 8.24 (d, 1H), 8.73 (dd, 1H); $^{13}$C-NMR ($CDCl_3$): δ 14.0, 22.8, 27.3, 28.9 (2C), 32.3, 35.6, 36.1, 52.1, 53.9 (2C), 54.7, 118.2, 119.2, 119.9, 120.1, 127.3, 143.0, 149.8; LC-MS: (M+H)$^+$ 445.2, $t_r$ 3.69 min. 80 (64LHY29-2): $^1$H-NMR ($CDCl_3$): δ 0.90 (t,3H), 1.14–1.38 (m, 9H), 1.62 (bd. d, 2H), 1.86 (bd. dd, 2H), 2.16 (ddd, 2H), 2.21 (dd, 2H), 2.75 (bd d, 2H), 4.50 (t, 2H), 7.59 (ddd, 1H), 8.21 (d, 1H), 8.25 (dd, 1H), 8.73 (dd, 1H); $^{13}$C-NMR ($CDCl_3$): δ 14.3, 23.1, 27.3, 29.2, 32.8 (2C), 36.0, 36.5, 47.2, 54.2 (2C), 55.2, 110.0, 119.1, 121.3, 123.0, 136.0, 141.8, 142.5; LC-MS: (M+H)$^+$ 445.2, $t_r$ 5.30 min.

General Procedure for the Preparation of Indole Derivatives.

Indole (1.20 mmol) was taken up in dry DMF (3 ml) prior to addition of sodium hydride (2.50 mmol) at rt., followed by addition of 3-chloro-1-iodo-propane (0.20 g, 1.0 mmol). The reaction mixture was shaken in a sealed vial at rt. for 16 h. 4-Butyl-piperidine (130 mg, 0.9 mmol) was added and the reaction mixture was further shaken at 50° C. for 72 h. The mixture was filtered and the filtrate was loaded onto a Varian SCX ion exchange column. The column was washed with methanol (10 ml, 2 column volumes) and the product was eluted from the column using 5% ammonium hydroxide in methanol (5 ml, 1 column volumes). The solute was concentrated in vacuo to produce the title compounds (79, 80).

Example 77

1-[3-(4-Butyl-piperidin-1-yl)-propyl]-2-methyl-1H-indole (81) (55-LH-1-1-(1402))

The reaction was carried out according to the general procedure using 2-methyl-1H-indole (157 mg, 1.20 mmol). The crude product was further purified by flash chromatography (MeOH: ethyl acetate; 1:4) to give the title compound 81. Yield 19 mg (21%). (UV/MS(%)=98/89); $^1$H NMR ($CDCl_3$): δ 7.50 (d, 1H), 7.31 (d, 1H), 7.12 (dt, 1H), 7.04 (dt, 1H), 6.23 (s, 1H), 4.12 (t, 2H), 2.87 (d, 2H), 2.44 (s, 3H), 2.31 (t, 2H), 1.98–1.83 (m, 4H), 1.67 (d, 2H), 1.32–1.19 (m, 9H), 0.89 (t, 3H).

Example 78

1-{1-[3-(4-Butyl-piperidin-1-yl)-propyl]-1H-indol-3-yl}-ethanone (82) (55-LH-1-2-(1403)

The reaction was carried out according to the general procedure using 1-(1H-indol-3-yl)-ethanone (191 mg, 1.20 mmol) to give the title compound 82. Yield 33 mg (32%). (UV/MS(%)=99/91); $^1$H NMR ($CDCl_3$): δ 8.39–8.34 (m, 1H), 7.80 (s, 1H), 7.41–7.36 (m, 1H), 7.30–7.25 (m, 2H), 4.24 (t, 2H), 2.80 (d, 2H), 2.21 (t, 2H), 2.01 (qv, 2H), 1.86 (t, 2H), 1.69 (d, 2H), 1.32–1.19 (m, 9H), 0.89 (t, 3H).

Example 79

{1-[3-(4-Butyl-piperidin-1-yl)-propyl]-1H-indol-3-yl}-acetonitrile (83) (55-LH-1-3-(1404)

The reaction was carried out according to the general procedure using (1H-indol-3-yl)-acetonitrile (187 mg, 1.20 mmol) to give the title compound 83. Yield 33 mg (11%). (UV/MS(%)=99192); $^1$H NMR ($CDCl_3$): δ 7.55 (d, 1H), 7.38 (d, 1H), 7.24 (t, 1H), 7.15 (t, 1H), 4.17 (t, 2H), 3.82 (s, 2H), 2.82 (d, 2H), 2.23 (t, 2H), 1.98 (qv, 2H), 1.85 (t, 2H), 1.67 (d, 2H), 1.33–1.17 (m, 9H), 0.89 (t, 3H).

Example 80

1-[3-(4-Butyl-piperidin-1-yl)-propyl]-1H-indole-3-carbonitrile (84) (55-LH-1-4-(1405))

The reaction was carried out according to the general procedure using 1H-indole-3-carbonitrile (170 mg, 1.20 mmol) to give the title compound 84. Yield 30 mg (31%). (UV/MS(%)=99/96); $^1$H NMR ($CDCl_3$): δ 7.75 (d, 1H), 7.63 (s, 1H), 7.45 (d, 1H), 7.35–7.25 (m, 2H), 4.25 (t, 2H), 2.79 (d, 2H), 2.20 (t, 2H), 1.99 (qv, 2H), 1.86 (t, 2H), 1.68 (d, 2H), 1.33–1.18 (m, 9H), 0.89 (t, 3H).

General Procedure for the Preparation of Benzimidazole Derivatives.

Benzimidazole (0.60 mmol) was taken up in dry THF (1 ml) prior to drop-wise addition of n-BuLi (1.6 M in Hexane) (413 µl, 0.66 mmol) at rt. The mixture was stirred for 15 min. followed by addition of 1,3-dibromo-propane (100 mg, 0.50 mmol) and then left at rt. for 16 h. 4-Butyl-piperidine (64 mg, 0.45 mmol) was added and the reaction mixture was shaken at 60° C. for 72 h. The mixture was filtered and the filtrate concentrated in vacuo prior to purification by preparative HPLC.

Example 81

1-[3-(4-Butyl-piperidin-1-yl)-propyl]-5,6-dimethyl-1H-benzoimidazole (85) (55-LH-8-2 (1387))

The reaction was carried out according to the general procedure using 5,6-dimethyl-benzoimidazole (88 mg, 0.60 mmol) to give the title compound 85. Yield 20 mg (14%). (MS(%)=100); $^1$H NMR ($CDCl_3$): δ 7.78 (s, 1H), 7.55 (s, 1H), 7.18 (d, 1H), 4.20 (t, 2H), 2.81 (d, 2H), 2.39 (s, 3H), 2.37 (s, 3H), 2.22 (t, 2H), 2.00 (qv, 2H), 1.85 (t, 2H), 1.68 (d, 2H), 1.33–1.18 (m, 9H), 0.90 (t, 3H).

Example 82

1-[3-(4-Butyl-piperidin-1-yl)-propyl]-5(6)-dimethyl-1H-benzoimidazole (86) (55-LH-8-3 (1388))

The reaction was carried out according to the general procedure using 5-methyl-benzoimidazole (79 mg, 0.60 mmol) to give the title compound (86) as a 50/50 mixture of the two regio isomers, according to $^1$H-NMR. Yield 42 mg (30%). (UV/MS(%)=100/100).

Example 83

1-[3-(4-Butyl-piperidin-1-yl)-propyl]-5-methoxy-1H-benzoimidazole (87) (55-LH-8-6 (1393))

The reaction was carried out according to the general procedure using 5-methoxy-benzoimidazole (89 mg, 0.60 mmol) to give the title compound (87) as a 50/50 mixture of the two regio isomers, according to $^1$H-NMR. Yield 62 mg (42%). (UV/MS(%)=100/100).

Example 84

{1-[3-(4-Butyl-piperidin-1-yl)-propyl]-1H-benzoimidazol-2-yl}-methanol (88) (55-LH-8-9 (1400))

The reaction was carried out according to the general procedure using (1H-benzoimidazol-2-yl)-methanol (89 mg, 0.60 mmol) to give the title compound 88. Yield 56 mg (38%). (UV/MS(%)=95/85); $^1$H NMR (CDCl$_3$): δ 7.69–7.65 (m, 1H), 7.32–7.28 (m, 1H), 7.21–7.18 (m, 2H), 4.88 (s, 2H), 4.38 (t, 2H), 2.70 (d, 2H), 2.18–2.06 (m, 4H), 1.74 (t, 2H), 1.58 (d, 2H), 1.24–1.14 (m, 9H), 0.81 (t, 3H).

Example 85

1-[3-(4-Butyl-piperidin-1-yl)-propyl]-2-trifuoromethyl-1H-benzoimidazole (89) (55-LH-8-10 (1401))

The reaction was carried out according to the general procedure using 2-trifuoromethyl-1H-benzoimidazole (112 mg, 0.60 mmol) to give the title compound 89. Yield 48 mg (29%). (UV/MS(%)=100/95); $^1$H NMR (CDCl$_3$): δ 7.78 (d, 1H), 7.74 (d, 1H), 7.49 (t, 1H), 7.41 (t, 1H), 4.48 (t, 2H), 2.86 (d, 2H), 2.41 (t, 2H), 2.08 (qv, 2H), 1.92 (t, 2H), 1.67 (d, 2H), 1.31–1.15 (m, 9H), 0.89 (t, 3H).

Example 86

(2-Trimethylstannanyl-phenyl)-carbamic acid tert-butyl ester (90) (53MF36)

To a solution of phenyl-carbamic acid tert-butyl ester (10.02 g, 52 mmol) in dry DMF (150 ml) was dropwise added tert-Buli (1.7 M in hexane) (80 ml, 0.14 mol) at −70° C. The reaction mixture was stirred for 30 min at −70° C. and 2 h at −20° C. before adding a solution of trimethyltinchloride in dry THF (1 M) (77.0 ml, 78 mmol). The reaction mixture was further stirred at −20° C. for 1 h followed by addition of an aqueous ammonium chloride solution (15%) (100 ml). The mixture was extracted with diethyl ether (3×300 ml) and the combined organic phases were dried over MgSO4 and evaporated in vacuo to give the crude title compound (90) (17.0 g), which was used in the next reaction without further purification.

Example 87

[2-(4-Chloro-butyryl)-phenyl]-carbamic acid tert-butyl ester (91) (53MF37)

To a mixture of (2-trimethylstannanyl-phenyl)-carbamic acid tert-butyl ester (17.0 g, 36 mmol) in dry toluene (300 ml) was added 4-chloro-butyryl chloride (5.3 g, 38 mmol) and dichlorobis(acetonitrile)palladium (II) (300 mg, 1.2 mmol). The reaction mixture was heated to reflux and left for 12 h., followed by evaporation to dryness and column chromatography (heptane:ethyl acetate; 10:1) to produce the title compound 91. Yield 7.2 g (47% from the phenyl-carbamic acid tert-butyl ester).

Example 88

{2-[4-(4-Butyl-piperidine-1-yl)-butyryl]-phenyl}-carbamic acid tert-butyl ester (92) (53MF38)

A flash was charged with [2-(4-chloro-butyryl)-phenyl]-carbamic acid tert-butyl ester (2.1 g, 7.1 mmol) and 4-butyl-piperidine (1.2 g, 8.5 mmol) before addition of pyridine (5 ml). To the reaction mixture was added potassium carbonate (1.17 g, 8.5 mmol) and the mixture was stirred at 100° C. for 12 h. Water (50 ml) was added followed by extraction with ethyl acetate (3×150 ml). The combined organic phases were dried over MgSO4, filtered and evaporated to dryness. The crude material was subjected to column chromatography (DCM:methanol; 20:1) which produced the pure title compound (92) (1.48 g, 52%).

Example 89

3-[3-(4-Butyl-piperidine-1-yl)-propyl]-1H-indazole, HCl (93) (53MF39)

A solution of {2-[4-(4-butyl-piperidine-1-yl)-butyryl]-phenyl}-carbamic acid tert-butyl ester (1.48 g, 3.7 mmol) in a solution of HCl in dioxane (4 N) (20 ml) was stirred at rt for 1 h before evaporation to dryness. The residue was dissolved in HCl (conc.) (15 ml) prior to addition of a solution of sodium nitrite (255 mg, 3.7 mmol) dissolved in water (3 ml). The mixture was stirred at 0° C. for 1 h before addition of stannyl chloride (1.7 g, 7.4 mmol) and then further stirred at rt for 3 h. The pH of the reaction mixture was adjusted with NaOH (2 N) until basic, followed by extraction with ethyl acetate (3×400 ml). The combined organic phases were dried over MgSO4, filtered and evaporated in vacuo. The crude material was subjected to column chromatography (DCM:methanol; 20:1), which produced the crude title compound 93. The crude compound was dissolved in diethyl ether followed by addition of HCl in ether (1.0 M) and stirred for 0.5 h. The solution was evaporated to dryness and the solid material was recrystalised twice from DCM:diethyl ether to produce the pure title compound. Yield 0.44 g (32%). (UV/MS(%)=100/100); mp: 160.5–164.0° C.; $^1$H NMR (CD$_3$OD): δ 7.96 (d, 1H), 7.62 (d, 2H), 7.33 (d, 1H), 3.58 (dt, 2H), 3.24–3.19 (m, 4H), 2.95 (t, 2H), 2.33 (qv, 2H), 1.97 (d, 2H), 1.65–1.28 (m, 9H), 0.91 (t, 3H). $^{13}$C NMR (CD$_3$OD): 143.9, 141.0, 130.3, 122.5, 120.8, 120.5, 110.9, 56.4, 53.2, 35.4, 33.6, 29.7, 28.5, 23.1, 22.7, 22.6, 13.1.

Example 90

3-[3-(4-Butyl-piperidine-1-yl)-propyl]-5-nitro-1H-indazole (94) (39MF43NO2); and Example 91
3-[3-(4-Butyl-piperidine-1-yl)-propyl]-5,7-dinitro-1H-indazole (95) (39MF43DiNO$_2$)

A solution of 3-[3-(4-butyl-piperidine-1-yl)-propyl]-1H-indazole (120 mg, 0.4 mmol) in a 1:1 mixture of nitric acid (fuming) and sulfuric acid (conc.) (2 ml) was stirred at 0° C. for 1.5 h. The pH of the mixture was adjusted with NaOH (8 N) whereupon a yellow oily material precipitated. The material was filtered and subjected to preparative TLC (DCM:methanol; 10:1) which produced the two pure title compounds. Yield: 25 mg (18%) (3-[3-(4-Butyl-piperidine-1-yl)-propyl]-5-nitro-1H-indazole) (94). $^1$H NMR (CDCl$_3$): δ 8.45 (s, 1H), 8.01 (d, 2H), 7.48 (d, 1H), 3.48 (d, 2H), 3.18–2.95 (m, 4H), 2.62 (t, 2H), 2.27 (qv, 2H), 1.82 (d, 2H), 1.58 (qv, 2H), 1.44–1.38 (m, 1H), 1.30–1.19 (m, 6H), 0.91 (t, 3H). $^{13}$C NMR(CDCl$_3$): 147.4, 143.4, 141.9, 121.6, 121.1, 117.7, 111.3, 57.4, 53.6, 35.4, 34.4, 30.0, 28.9, 24.2, 23.5, 22.9, 14.2. Yield: 10 mg (6%) (3-[3-(4-Butyl-piperidine-1-yl)-propyl]-5,7-dinitro-1H-indazole) (95). $^1$H NMR (CDCl$_3$): δ 9.18 (d, 1H), 9.05 (d, 1H), 3.18–3.10 (m, 4H), 2.68 (t, 2H), 2.25–2.14 (m, 4H), 1.74 (d, 2H), 1.45–1.22 (m, 7H), 0.91 (t, 3H).

Example 92

4-(4-Butyl-piperidin-1-yl)-1-(2-metylsulfanyl-phenyl)-butan-1-one (96) (65MF07)

To a stirred solution of 2-bromothioanisole (12.85 g, 63.3 mmol) in dry THF (60 ml) at −78° C. was added n-BuLi (1.6 N in hexane) (41 ml, 65.3 mmol) via a syringe over 30 min. The reaction mixture was further stirred at −78° C. for 30 min. prior to the addition of a solution of 4-(4-butyl-cyclohexyl)-N-methoxy-N-methyl-butyramide (11.41 g, 42.2 mmol) dissolved in dry THF (10 ml). The mixture was held at −78° C. for 0.5 h and at rt for 0.5 h before addition of water (100 ml) and by extraction with ethyl acetate (3×150 ml). The combined organic phases were dried over MgSO4, filtered and evaporated in vacuo to produce the crude title compound 96 (11.9 g). Purity according LC-MS analysis: (UV/MS(%)=90/91).

Example 93

3-[3-(4-Butyl-piperidin-1-yl)-propyl]-benzo[d]isothiazole (97) (65MF08)

A mixture of crude 4-(4-butyl-piperidin-1-yl)-1-(2-metylsulfanyl-phenyl)-butan-1-one (11.9 g, 36 mmol) and hydroxylamine-O-sulfonic acid (6.11 g, 54 mmol) in acetic acid (500 ml) was stirred at rt for 72 h followed by heating at 100° C. for 24 h. The reaction mixture was cooled to rt and the pH adjusted with 2 N NaOH to a basic condition (pH=9), before extraction with ethyl acetate (3×400 ml). The combined organic phases were dried over MgSO4, filtered and evaporated in vacuo to produce 12.1 g of the crude product. The crude product was purified by column chromatography (DCM:MeOH; 20:1) to yield the title compound 97. Yield 3.67 g (18.3%) from 2-bromothioanisole. The oxalate salt was formed by addition of oxalic acid and recrystallised from methanol-diethyl ether to give white crystals, which were filtered and dried. (UV/MS(%)=90/91), mp=193.4–194.0° C. $^1$H NMR (CDCl$_3$): δ 7.98 (d, 1H), 7.91 (d, 1H), 7.50 (t, 1H), 7.41 (t, 1H), 3.14 (t, 2H), 2.92 (d, 2H), 2.46 (t, 2H), 2.18 (qv, 2H), 1.92 (t, 2H), 1.66 (d, 2H), 1.35–1.18 (m, 9H), 0.88 (t, 3H). $^{13}$C NMR (CDCl$_3$): 166.6, 152.5, 134.9, 127.6, 124.5, 123.6, 120.0, 58.5, 54.2, 36.4, 35.9, 32.5, 29.7, 25.5, 23.1, 14.2.

Example 94

3-[3-(4-Butyl-piperidin-1-yl)-propyl]-5-methoxy-1H-indazole (98) (53MF35)

A small flask was charged with 1-(2-amino-5-methoxy-phenyl)-4-(4-butyl-piperidin-1-yl)-butan-1-one (1.58 g, 47 mmol) in conc. HCl (15 ml). The mixture was cooled to 0° C. followed by addition of sodium nitrite (0.61 g, 88 mmol) and water (3 ml) and stirring at 0° C. for 2 h. Addition of tin(II) chloride dihydrate (2.68 g, 11.9 mmol) produced a precipitated that was filtered, washed twice with ice-cold water and dried. The filtrate was dissolved in ethyl acetate (100 ml) and 1N NaOH (150 ml), followed by extraction with ethyl acetate (3×150 ml). The combined organic phases were dried over MgSO4, filtered and evaporated in vacuo to produce 1.30 g of the crude product. The crude product was purified by column chromatography (DCM:MeOH; 20:1) to yield the title compound 98. The oxalate salt was formed by addition of oxalic acid and recrystallised from methanol-diethyl ether to give white crystals that were filtered and dried. Yield 0.97 g (49%). $^1$H NMR (CDCl$_3$): δ 7.32 (dd, 1H), 7.03 (dd, 1H), 6.98 (d, 1H), 3.85 (s, 3H), 3.10 (d, 2H), 2.96 (t, 2H), 2.61 (t, 2H), 2.15–2.05 (m, 4H), 1.68 (d, 2H), 1.40–1.20 (m, 9H), 0.87 (t, 3H). $^{13}$C NMR(CDCl$_3$): 177.2, 154.5, 145.6, 137.4, 122.4, 119.0, 111.2, 99.6, 58.0, 55.9, 53.5, 36.1, 35.5, 31.5, 29.1, 25.2, 24.9, 23.4, 23.0, 14.2.

Example 95

3-[3-(4-Butyl-piperidin-1-yl)-propyl]-4-methoxy-1H-indazole (99) (53MF470)

To a solution of 3-(3-chloro-propyl)-4-methoxy-1H-indazole (0.99 g, 4.41 mmol) in acetonitrile (25 ml) was added 4-butylpiperidine (0.61 g, 4.41 mmol) at rt. The reaction mixture was stirred at rt. for 3 days before addition of water (50 ml). The aqueous phase was extracted with ethyl acetate (3×50 ml) and the combined organic phases were dried over MgSO4, filtered and evaporated in vacuo to produce 1.40 g of the crude product. The crude product was purified by column chromatography (ethyl acetate:MeOH:Et$_3$N; 10:5:3) to yield the title compound 99. Yield 0.65 g (45%). $^1$H NMR (CDCl$_3$): δ 7.24 (d, 1H), 7.00 (d, 1H), 6.41 (t, 1H), 3.91 (s, 3H), 3.58 (d, 2H), 3.20–2.99 (m, 4H), 2.55 (t, 2H), 2.22 (qv, 2H), 1.81 (d, 2H), 1.61 (q, 2H), 1.41–1.08 (m, 7H), 0.87 (t, 3H). $^{13}$C NMR (CDCl$_3$): 154.9, 144.3, 143.3, 129.2, 113.1, 103.1, 99.8, 57.1, 55.4, 53.3, 35.3, 34.3, 29.5, 28.8, 25.6, 23.1, 22.8, 14.1.

Example 96

3-[3-(4-Butyl-piperidin-1-yl)-propyl]-6-methoxy-1H-indazole (100) (53MF47P)

To a solution of 3-(3-chloro-propyl)-6-methoxy-1H-indazole (0.99 g, 4.41 mmol) in acetonitrile (25 ml) was added 4-butylpiperidine (0.61 g, 4.41 mmol) at rt. The reaction mixture was stirred at rt. for 3 days before addition of water (50 ml). The aqueous phase was extracted with ethyl acetate (3×50 ml) and the combined organic phases were dried over MgSO4, filtered and evaporated in vacuo to produce 0.85 g of the crude product. The crude product was purified by column chromatography (ethyl acetate:MeOH:Et$_3$N; 10:5:3) to yield the title compound 100. Yield 0.55 g (38%). $^1$H NMR (CDCl$_3$): δ 7.42 (d, 1H), 6.80–6.72 (3, 2H), 3.80 (s, 3H), 3.60 (d, 2H), 3.11–2.92 (m, 4H), 2.55 (t, 2H), 2.23 (qv, 2H), 1.79 (d, 2H), 1.58 (q, 2H), 1.40–1.08 (m, 7H), 0.83 (t, 3H). $^{13}$C NMR (CDCl$_3$): 160.8, 143.8, 142.6, 120.7, 116.2, 114.0, 91.2, 57.1, 55.6, 53.4, 35.3, 34.3, 29.5, 28.8, 23.7, 22.8, 22.7, 14.1.

Example 97

3-[3-(4-Butyl-piperidin-1-yl)-propyl]-1H-indazole-4-ol(101) (53MF51)

3-[3-(4-Butyl-piperidin-1-yl)-propyl]-4-methoxy-1H-indazole (28 mg, 0.09 mmol) was dissolved in dry DCM (1.0 ml) and cooled to 0° C. before addition of 1M bromotribromide solution in DCM (0.50 ml, 0.50 mmol). The mixture was left at rt for 12 h, followed by addition of water (5 ml) and 2N NaOH (10 ml). The aqueous phase was extracted with DCM (3×25 ml) and the combined organic phases were dried over MgSO4, filtered and evaporated in vacuo to produce 13 mg of the crude product. Purification by preparative HPLC followed by treatment with HCl in dioxane (4M, 2 ml) yielded the title compound (101) as white crystals after washing with DCM. Yield: 6.0 mg, 17% $^1$H NMR (CDCl$_3$): δ 7.18 (t, 1H), 6.81 (d, 1H), 6.50 (t, 1H), 2.85 (d, 2H), 2.23 (t, 2H), 1.98 (qv, 2H), 1.83 (t, 2H), 1.62 (d, 2H), 1.41 (d, 2H), 1.21–1.01 (m, 9H), 0.78 (t, 3H).

Example 98

3-[3-(4-Butyl-piperidin-1-yl)-propyl]-1H-indazole-6-ol (102) (53MF52)

3-[3-(4-Butyl-piperidin-1-yl)-propyl]-6-methoxy-1H-indazole (28 mg, 0.09 mmol) was dissolved in dry DCM (1.0 ml) and cooled to 0° C. before addition of 1M bromotribromide solution in DCM (0.50 ml, 0.50 mmol). The mixture was held at rt for 12 h, followed by addition of water (5 ml) and 2N NaOH (10 ml). The aqueous phase was extracted with DCM (3×25 ml) and the combined organic phases were dried over MgSO4, filtered and evaporated in vacuo to produce 17 mg of the crude product. Purification by preparative HPLC followed by treatment with HCl in dioxane (4M, 2 ml) yielded the title compound (102) as white crystals after washing with DCM. Yield: 10 mg, 17%. $^1$H NMR (CD$_3$OD): δ 7.54 (d, 1H), 6.77 (s, 1H), 6.71 (d, 1H), 3.55 (d, 2H), 3.15 (t, 2H), 3.04 (t, 2H), 2.90 (dt, 2H), 2.22 (qv, 2H), 1.97 (d, 2H), 1.58–1.28 (m, 9H), 0.92 (t, 3H). $^{13}$C NMR (CD$_3$OD): 159.0, 145.5, 144.4, 121.7, 117.2, 113.7, 94.4, 58.2, 54.3, 36.5, 34.8, 31.0, 29.7, 24.7, 24.3, 23.7, 14.3.

Example 99

3-[3-(4-Butyl-piperidin-1-yl)-propyl]-1H-indazole-5-ol (103) (53MF50)

3-[3-(4-Butyl-piperidin-1-yl)-propyl]-5-methoxy-1H-indazole (28 mg, 0.09 mmol) was dissolved in dry DCM (1.0 ml) and cooled to 0° C. before addition of 1M bromotribromide solution in DCM (0.50 ml, 0.50 mmol). The mixture was held at rt for 12 h, followed by addition of water (5 ml) and 2N NaOH (10 ml). The aqueous phase was extracted with DCM (3×25 ml) and the combined organic phases were dried over MgSO4, filtered and evaporated in vacuo to produce 14 mg of the crude product. Purification by preparative HPLC followed by treatment with HCl in dioxane (4M, 2 ml) yielded the title compound (103) as white crystals after washing with DCM. Yield: 16 mg, 60%. $^1$H NMR (CD$_3$OD): δ 7.54 (d, 1H), 6.77 (s, 1H), 6.71 (d, 1H), 3.55 (d, 2H), 3.15 (t, 2H), 3.04 (t, 2H), 2.90 (dt, 2H), 2.22 (qv, 2H), 1.97 (d, 2H), 1.58–1.28 (m, 9H), 0.92 (t, 3H). $^{13}$C NMR (CD$_3$OD): 159.0, 145.5, 144.4, 121.7, 117.2, 113.7, 94.4, 58.2, 54.3, 36.5, 34.8, 31.0, 29.7, 24.7, 24.3, 23.7, 14.3.

Example 100

Screening Of Test Compounds In An Assay Using Muscarinic Receptor Subtypes m1, m2, m3, m4 and m5.

The m1, m2, m3, m4 and m5 muscarinic receptor subtypes were cloned substantially as described by Bonner et al., *Science* 273:527(1987) and Bonner et al., *Neuron* 1:403 (1988). R-SAT assays were carried out substantially as described in U.S. Pat. Nos. 5,707,798, 5,912,132, and 5,955,281, and by Braüner-Osborne & Brann, *Eur. J. Pharmacol.* 295:93 (1995). NIH-3T3 cells (available from the American Type Culture Collection as ATCC CRL 1658) were transfected with plasmid DNA encoding the m1, m2, m3, m4 or m5 receptors and plasmid DNA encoding β-galactosidase. Transfected cells were grown in the presence of between 1 nM and 40 μM of the test compound for 5 days. On day 5, the cells were lysed using 0.5% Nonidet-P and β-galactosidase expression was quantified using the chromogenic substrate o-nitrophenyl-β-D-galactoside (ONGP).

Data were normalized relative to the maximum response of the cells to the muscarinic agonist carbachol, and the following equation was fitted to the data:

response=minimum+(maximum−minimum)/(1+(*EC*50/[ligand]))

Where [ligand]=ligand concentration.

% Efficacy was defined as:

(maximum−minimum)/(maximum response of cells to carbachol).

pEC50=−log (EC50).

Where data gave a bell-shaped curve, "maximum" was defined as the highest observed response.

The results, which demonstrate the selective agonist activity of several compounds of the invention, are below presented in Table 1.

TABLE 1

Selectivity of Muscarinic Agonists

| | m1 | | m2 | | m3 | | m4 | | m5 | |
|---|---|---|---|---|---|---|---|---|---|---|
| Example | % Eff | pEC50 | % Eff | pEC50 | % Eff | pEC50 | % Eff | pEC50 | % Eff | pEC50 |
| 12 | 59 | 5.9 | no response | | no response | | | | no response | |
| 19 | 86 | 7.3 | no response | | no response | | 70 | 6.5 | no response | |
| 24 | 75 | 6.9 | no response | | no response | | 41 | 6.3 | no response | |

TABLE 1-continued

Selectivity of Muscarinic Agonists

| | m1 | | m2 | | m3 | | m4 | | m5 | |
|---|---|---|---|---|---|---|---|---|---|---|
| Example | % Eff | pEC50 | % Eff | pEC50 | % Eff | pEC50 | % Eff | pEC50 | % Eff | pEC50 |
| 28 | 38 | 6.5 | | | no response | | no response | | no response | |
| 32 | 52 | 6.4 | no response | | no response | | no response | | no response | |
| 41 | 81 | 6.9 | no response | | no response | | 69 | 6.2 | 31 | <5.5 |
| 42 | 51 | 7.1 | | | | | | | | |
| 43 | 66 | 6.3 | | | | | 30 | 6.0 | no response | |
| 44 | 72 | 6.1 | | | | | | | | |
| 61 | 59 | 6.3 | no response | | no response | | 39 | 6.0 | no response | |
| 65 | 45 | 6.0 | no response | | | | 34 | <5.5 | | |
| 73 | 37 | 6.2 | | | | | no response | | | |
| 77 | 71 | 7.0 | | | | | 96 | 6.3 | | |
| 81 | 72 | 6.4 | | | | | 77 | <5.5 | | |
| 89 | 85 | 7.3 | no response | | no response | | 53 | 6.8 | no response | |
| 93 | 83 | 7.1 | no response | | no response | | 58 | 6.4 | no response | |

% Eff: % Efficacy
pEC50: −log EC50
No response: Efficacy < 25% maximum response of carbachol. This level of activity is not considered significantly different to no response.

Example 101

Effects of Compound 35AKU-21 on Intaocular Pressure in Primates.

All studies were conducted in fully conscious female cynomolgus monkeys (Macacca fascicularis) weighing 3–4 kg. Unilateral ocular hypertension was produced by argon laser photocoagulation to the mid-trabecular meshwork (Sawyer & McGuigan, *Invest. Ophthalmol. Vis. Sci.* 29:81 (1988)).

Animals were trained to allow measuring intraocular pressure (IOP) with a model 30 Classic pneumatonometer (Mentor O&O Co.). Throughout each study, monkeys sat in specially designed chairs (Primate Products, San Francisco) and fed fruits and juices as needed.

The drug was administered topically. The drug was formulated in an aqueous solution such as distilled water, saline or citrate buffer at a pH 5–7 and applied unilaterally as a 35 μL drop; the contralateral eye received an equal volume of saline (or vehicle). Two baseline measurements were made prior to administration of the drug, followed by periodic measurements up to 6 hours post drug administration. The results of this study are shown below in Table 2.

TABLE 2

Ocular Hypotensive Effect of 35AKU-21 in Glaucomatous Monkeys

| | TIME (HR) | | | |
|---|---|---|---|---|
| | 1 | 2 | 4 | 6 |
| % IOP Change | −9.3 | −21.3 | −25.9 | −29.2 |
| SEM | 2.2 | 5.0 | 6.5 | 6.2 |
| N | 6 | 6 | 6 | 6 |
| p value | .008 | .009 | .016 | .012 | p value is for comparison to vehicle control in contralateral eye.

We claim:

1. A compound of formula (I):

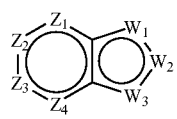

(I)

wherein:

$Z_1$ is $CR_1$, $Z_2$ is $CR_2$, $Z_3$ is $CR_3$, and $Z_4$ is $CR_4$;
$W_1$ is S, $W_2$ is N or $CR_6$, and $W_3$ is CG;
G is of formula (II):

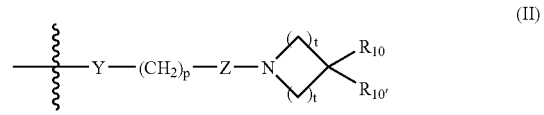

(II)

Y is O, S, CHOH, —NHC(O)—, —C(O)NH—, —C(O)—, —OC(O)—, —(O)CO—, —NR$_7$—, —CH=N—, or absent;

p is 1, 2, 3, 4 or 5;

Z is $CR_8R_9$ or absent;

each t is 1, 2, or 3;

each $R_1$, $R_2$, $R_3$, and $R_4$, independently, is H, amino, hydroxyl, halo, or straight- or branched-chain $C_{1-6}$ alkyl, $C_{2-6}$ alkenyl, $C_{2-6}$ alkynyl, methoxymethyl, ethoxymethyl, proproxymethyl, $C_{1-6}$ haloalkyl, —CN, —CF$_3$, —OR$_{11}$, —COR$_{11}$, —NO$_2$, —SR$_{11}$, —NHC(O)R$_{11}$, —C(O)NR$_{12}$R$_{13}$, —NR$_{12}$R$_{13}$, —NR$_{11}$C(O)NR$_{12}$R$_{13}$, —SO$_2$NR$_{12}$R$_{13}$, —OC(O)R$_{11}$, —O(CH$_2$)$_q$NR$_{12}$R$_{13}$, or —(CH$_2$)$_q$NR$_{12}$R$_{13}$, where q is an integer from 2 to 6, or $R_1$ and $R_2$ together form —NH—N=N— or $R_3$ and $R_4$ together form —NH—N=N—;

each $R_5$, $R_6$, and $R_7$, independently, is H, $C_{1-6}$ alkyl; formyl; $C_{3-6}$ cycloalkyl; $C_{5-6}$ aryl, optionally substituted with halo or $C_{1-6}$ alkyl; or $C_{5-6}$ heteroaryl, optionally substituted with halo or $C_{1-6}$ alkyl;

each $R_8$ and $R_9$, independently, is H or straight- or branched-chain $C_{1-8}$ alkyl;

$R_{10}$ is straight- or branched-chain $C_{1-8}$ alkyl, $C_{2-8}$ alkenyl, $C_{2-8}$ alkynyl, $C_{1-8}$ alkylidene, $C_{1-8}$ alkoxy, or methoxymethyl, ethoxymethyl, proproxymethyl;

$R_{10}'$ is H, straight- or branched-chain $C_{1-8}$ alkyl, $C_{2-8}$ alkenyl, $C_{2-8}$ alkynyl, $C_{1-8}$ alkylidene, $C_{1-8}$ alkoxy, methoxymethyl, ethoxymethyl, proproxymethyl, $C_{1-8}$ aminoalkyl, $C_{1-8}$ haloalkyl, $C_{1-8}$ alkoxycarbonyl, $C_{1-8}$ hydroxyalkoxy, $C_{1-8}$ hydroxyalkyl, or $C_{1-8}$ alkylthio;

each $R_{11}$, independently, is H, straight- or branched-chain $C_{1-8}$ alkyl, $C_{2-8}$ alkenyl, $C_{2-8}$ alkynyl, methoxymethyl, ethoxymethyl, proproxymethyl, $C_{2-8}$ aminoalkyl, $C_{2-8}$ haloalkyl, $C_{1-8}$ alkoxycarbonyl, $C_{2-8}$ hydroxyalkyl, —C(O)—$C_{5-6}$ aryl substituted with $C_{1-3}$ alkyl or halo, $C_{5-6}$ aryl, $C_{5-6}$ heteroaryl, $C_{5-6}$ cycloalkyl, $C_{5-6}$ heterocycloalkyl, —C(O)NR$_{12}$R$_{13}$, —CR$_5$R$_{12}$R$_{13}$, —(CH$_2$)$_t$NR$_{12}$R$_{13}$, t is an integer from 2 to 8; and each $R_{12}$ and $R_{13}$, independently, is H, $C_{1-6}$ alkyl; $C_{3-6}$ cycloalkyl; $C_{5-6}$ aryl, optionally substituted with halo or $C_{1-6}$ alkyl; or $C_{5-6}$ heteroaryl, optionally substituted with halo or $C_{1-6}$ alkyl;

or a pharmaceutically acceptable salt, ester or prodrug thereof.

2. The compound of claim 1, wherein each t is 2.

3. The compound of claim 2, wherein $R_{10}$ is n-butyl.

4. The compound of claim 2, wherein each $R_1$, $R_2$, $R_3$, and $R_4$, independently, is H, hydroxyl, halo, methoxymethyl, ethoxymethyl, proproxymethyl, $CF_3$, —NO$_2$, or straight- or branched-chain $C_{1-6}$ alkyl, or $R_1$ and $R_2$ together form —NH—N═N— or $R_3$ and $R_4$ together form —NH—N═N—.

5. The compound of claim 2, wherein Y is absent or O, p is 0, 1, 2 or 3, and $R_8$ and $R_9$ are H.

6. The compound of claim 5, wherein Z is absent, Y is absent and p is 3.

7. The compound of claim 6, wherein $R_{10}$ is n-butyl.

8. The compound of claim 1, wherein the compound is:
1-benzo[b]thiophen-2-yl-4-(4-butylpiperidin-1-yl)-butan-1-one
4-(4-butylpiperidin-1-yl)-1-(5-fluoro-3-methyl-benzo[b]thiophen-2-yl)-butan-1-one;
1-(3-bromo-benzo[b]thiophen-2-yl)-4-(4-butylpiperidin-1-yl)-butan-1-one
1-(3-benzo[b]thiophen-2-yl-propyl)-4-butylpiperidine;
4-butyl-1-[3-(5-fluoro-3-methyl-benzo[b]thiophen-2-yl)-propyl]-piperidine;
1-(3-benzo[b]thiophen-2-yl-propyl)-4-methylpiperidine
1-(3-benzo[b]thiophen-2-yl-propyl)-4-benzylpiperidine; or
3-[3-(4-butyl-piperidin-1-yl)-propyl]-benzo[d]isothiazole.

9. A pharmaceutical composition comprising an effective amount of a compound of formula (I):

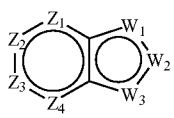
(I)

wherein:
$Z_1$ is $CR_1$, $Z_2$ is $CR_2$, $Z_3$ is $CR_3$, and $Z_4$ is $CR_4$;
$W_1$ is S, $W_2$ is N or $CR_6$, and $W_3$ is CG;
G is of formula (II):

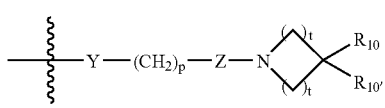
(II)

Y is O, S, CHOH, —NHC(O)—, —C(O)NH—, —C(O)—, —OC(O)—, —(O)CO—, —NR$_7$—, —CH═N—, or absent;
p is 1, 2, 3, 4 or 5;
Z is $CR_8R_9$ or absent;
each t is 1, 2, or 3;
each $R_1$, $R_2$, $R_3$, and $R_4$, independently, is H, amino, hydroxyl, halo, or straight- or branched-chain $C_{1-6}$ alkyl, $C_{2-6}$ alkenyl, $C_{2-6}$ alkynyl, methoxymethyl, ethoxymethyl, proproxymethyl, $C_{1-6}$ haloalkyl, —CN, —CF$_3$, —OR$_{11}$, —COR$_{11}$, —NO$_2$, —SR$_{11}$, —NHC(O)R$_{11}$, —C(O)NR$_{12}$R$_{13}$, —NR$_{12}$R$_{13}$, —NR$_{11}$C(O)NR$_{12}$R$_{13}$, —SO$_2$NR$_{12}$R$_{13}$, —OC(O)R$_{11}$, —O(CH$_2$)$_q$NR$_{12}$R$_{13}$, or —(CH$_2$)$_q$NR$_{12}$R$_{13}$, where q is an integer from 2 to 6, or $R_1$ and $R_2$ together form —NH—N═N— or $R_3$ and $R_4$ together form —NH—N═N—;

each $R_5$, $R_6$, and $R_7$, independently, is H, $C_{1-6}$ alkyl; formyl; $C_{3-6}$ cycloalkyl; $C_{5-6}$ aryl, optionally substituted with halo or $C_{1-6}$ alkyl; or $C_{5-6}$ heteroaryl, optionally substituted with halo or $C_{1-6}$ alkyl;

each $R_8$ and $R_9$, independently, is H or straight- or branched-chain $C_{1-8}$ alkyl;

$R_{10}$ is straight- or branched-chain $C_{1-8}$ alkyl, $C_{2-8}$ alkenyl, $C_{2-8}$ alkynyl, $C_{1-8}$ alkylidene, $C_{1-8}$ alkoxy, or methoxymethyl, ethoxymethyl, proproxymethyl;

$R_{10}'$ is H, straight- or branched-chain $C_{1-8}$ alkyl, $C_{2-8}$ alkenyl, $C_{2-8}$ alkynyl, $C_{1-8}$ alkylidene, $C_{1-8}$ alkoxy, methoxymethyl, ethoxymethyl, proproxymethyl, $C_{1-8}$ aminoalkyl, $C_{1-8}$ haloalkyl, $C_{1-8}$ alkoxycarbonyl, $C_{1-8}$ hydroxyalkoxy, $C_{1-8}$ hydroxyalkyl, or $C_{1-8}$ alkylthio;

each $R_{11}$, independently, is H, straight- or branched-chain $C_{1-8}$ alkyl, $C_{2-8}$ alkenyl, $C_{2-8}$ alkynyl, methoxymethyl, ethoxymethyl, proproxymethyl, $C_{2-8}$ aminoalkyl, $C_{2-8}$ haloalkyl, $C_{1-8}$ alkoxycarbonyl, $C_{2-8}$ hydroxyalkyl, —C(O)—$C_{5-6}$ aryl substituted with $C_{1-3}$ alkyl or halo, $C_{5-6}$ aryl, $C_{5-6}$ heteroaryl, $C_{5-6}$ cycloalkyl, $C_{5-6}$ heterocycloalkyl, —C(O)NR$_{12}$R$_{13}$, —CR$_5$R$_{12}$R$_{13}$, —(CH$_2$)$_t$NR$_{12}$R$_{13}$, t is an integer from 2 to 8; and each $R_{12}$ and $R_{13}$, independently, is H, $C_{1-6}$ alkyl; $C_{3-6}$ cycloalkyl; $C_{5-6}$ aryl, optionally substituted with halo or $C_{1-6}$ alkyl; or $C_{5-6}$ heteroaryl, optionally substituted with halo or $C_{1-6}$ alkyl;

or a pharmaceutically acceptable salt, ester or prodrug thereof.

10. A pharmaceutical composition of claim 9, wherein each t is 2.

11. A pharmaceutical composition of claim 10, wherein $R_{10}$ is n-butyl.

12. A pharmaceutical composition of claim 10, wherein each $R_1$, $R_2$, $R_3$, and $R_4$, independently, is H, hydroxyl, halo, methoxymethyl, ethoxymethyl, proproxymethyl, $CF_3$, —NO$_2$, or straight- or branched-chain $C_{1-6}$ alkyl, or $R_1$ and $R_2$ together form —NH—N═N— or $R_3$ and $R_4$ together form —NH—N═N—.

13. A pharmaceutical composition of claim 10, wherein Y is absent or O, p is 0, 1, 2 or 3, and $R_8$ and $R_9$ are H.

14. A pharmaceutical composition of claim 13, wherein Z is absent, Y is absent and p is 3.

15. A pharmaceutical composition of claim 14, wherein $R_{10}$ is n-butyl.

16. A pharmaceutical composition of claim 10, wherein the compound is:
1-benzo[b]thiophen-2-yl-4-(4-butylpiperidin-1-yl)-butan-1-one 4-(4-butylpiperidin-1-yl)-1-(5-fluoro-3-methyl-benzo[b]
thiophen-2-yl)-butan-1-one;
1-(3-bromo-benzo[b]thiophen-2-yl)-4-(4-butylpiperidin-
1-yl)-butan-1-one
1-(3-benzo[b]thiophen-2-yl-propyl)-4-butylpiperidine;
4-butyl-1-[3-(5-fluoro-3-methyl-benzo[b]thiophen-2-yl)-
propyl]-piperidine;

1-(3-benzo[b]thiophen-2-yl-propyl)-4-methylpiperidine
1-(3-benzo[b]thiophen-2-yl-propyl)-4-benzylpiperidine;
or
3-[3-(4-butyl-piperidin-1-yl)-propyl]-benzo[d]isothiaz-
ole.

\* \* \* \* \*